US009745624B2

(12) United States Patent
Wangh et al.

(10) Patent No.: US 9,745,624 B2
(45) Date of Patent: Aug. 29, 2017

(54) METHODS FOR SEQUENTIAL DNA AMPLIFICATION AND SEQUENCING

(75) Inventors: Lawrence J. Wangh, Auburndale, MA (US); John E. Rice, Quincy, MA (US); J. Aquiles Sanchez, Framingham, MA (US); Kenneth E. Pierce, Natick, MA (US); Jesse Salk, Seattle, WA (US); Arthur H. Reis, Arlington, MA (US); Cristina Hartshorn, West Roxbury, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 13/564,528

(22) Filed: Aug. 1, 2012

(65) Prior Publication Data

US 2013/0095479 A1 Apr. 18, 2013

Related U.S. Application Data

(62) Division of application No. 12/292,038, filed on Nov. 10, 2008, now abandoned, which is a division of application No. 11/252,433, filed on Oct. 17, 2005, now Pat. No. 7,632,642.

(60) Provisional application No. 60/619,654, filed on Oct. 18, 2004.

(51) Int. Cl.
  *C12Q 1/68* (2006.01)
(52) U.S. Cl.
  CPC ......... *C12Q 1/6869* (2013.01); *C12Q 1/6844* (2013.01); *C12Q 1/6851* (2013.01); *C12Q 1/6876* (2013.01); *C12Q 2600/156* (2013.01); *C12Q 2600/16* (2013.01)
(58) Field of Classification Search
  None
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,066,584 A | 11/1991 | Gyllensten et al. | |
| 5,210,015 A | 5/1993 | Gelfand et al. | |
| 5,487,972 A | 1/1996 | Gelfand et al. | |
| 5,538,848 A | 7/1996 | Livak et al. | |
| 5,756,285 A * | 5/1998 | Fuller | 435/6.11 |
| 5,925,517 A | 7/1999 | Tyagi et al. | |
| 5,994,056 A | 11/1999 | Higuchi | |
| 6,103,476 A | 8/2000 | Tyagi et al. | |
| 6,140,054 A | 10/2000 | Wittwer et al. | |
| 6,150,097 A | 11/2000 | Tyagi et al. | |
| 6,174,670 B1 | 1/2001 | Wittwer et al. | |
| 6,365,729 B1 | 4/2002 | Tyagi et al. | |
| 6,472,156 B1 | 10/2002 | Wittwer et al. | |
| 2002/0119450 A1 | 8/2002 | Lee et al. | |
| 2002/0137047 A1 * | 9/2002 | Baskin | C12Q 1/6851 435/6.1 |
| 2003/0022231 A1 | 1/2003 | Wangh et al. | |
| 2003/0082550 A1 * | 5/2003 | Thomann | C12N 9/0083 435/6.14 |
| 2003/0108906 A1 * | 6/2003 | Brooksbank | C07K 14/47 435/6.16 |
| 2004/0053254 A1 | 3/2004 | Wangh et al. | |
| 2004/0175704 A1 | 9/2004 | Sorge et al. | |
| 2006/0147959 A1 * | 7/2006 | Bell | C12Q 1/485 435/6.16 |
| 2006/0263775 A1 * | 11/2006 | Kaplan | C07K 14/47 435/6.16 |

FOREIGN PATENT DOCUMENTS

| | | |
|---|---|---|
| EP | 1 375 674 B1 | 1/2004 |
| WO | 00/18965 | 4/2000 |
| WO | WO 01/31062 A1 | 5/2001 |
| WO | WO 02/097132 A2 | 12/2002 |
| WO | WO 02101004 A2 * | 12/2002 |
| WO | WO 03/040397 A2 | 5/2003 |
| WO | WO 03/054233 A1 | 7/2003 |
| WO | WO 2006/044994 A2 | 4/2006 |

OTHER PUBLICATIONS

Laue et al. Human Molecular Genetics (1995) 4(8): 1429-1433.*
Nordstrom et al. Journal of Biochemical and Biophysical Methods (2002) 52: 71-82.*
Brow et al. PCR Protocols: A Guide to Methods and Applications (1990) pp. 189-196.*
Notice of Allowance mailed Jul. 31, 2009 in U.S. Appl. No. 11/252,433.
Afonina, I. A., et al., "Minor Groove Binder-Conjugated DNA Probes for Quantitative DNA Detection by Hybridization-Triggered Fluorescence", BioTechniques, vol. 32, No. 4, pp. 940-949 (2002).
Allwai, H. T., et al., "Thermodynamics and NMR of Internal G•T Mismatches in DNA", Biochem., vol. 36, pp. 10581-10-594 (1997).
Crockett, A. O., et al., "Fluorescein-Labeled Oligonucleotides for Real-Time PCR: Using the Inherent Quenching of Deoxyguanosine Nucleotides", Anal. Biochem., vol. 290, pp. 89-97 (2001).
Gyllensten, U. B., et al., "Generation of single-stranded DNA by the polymerase chain reaction and its application to direct sequencing of the HLA-DQA locus", Proc. Natl. Acad. Sci., vol. 85 pp. 7652-7656 (1998).
Lee, M A., et al., "ResonSense®: simple linear fluorescent probes for quantitative homogeneous rapid polymerase chain reaction", Anal. Chim. Acta, vol. 457, pp. 61-70 (2002).

(Continued)

*Primary Examiner* — Angela M Bertagna
(74) *Attorney, Agent, or Firm* — Foley Hoag LLP

(57) ABSTRACT

Homogenous detection during or following PCR amplification, preferably LATE-PCR, utilizing fluorescent DNA dye and indirectly excitable labeled primers and probes, improves reproducibility and quantification. Low-temperature homogeneous detection during or following non-symmetric PCR amplification, preferably LATE-PCR, utilizing fluorescent DNA dye and indirectly excitable labeled mismatch-tolerant probes permits analysis of complex targets. Sequencing sample preparation methods following LATE-PCR amplifications reduce complexity and permit "single-tube" processing.

5 Claims, 24 Drawing Sheets

(56) References Cited

OTHER PUBLICATIONS

Li, Q., et al., "A new class of homogeneous nucleic acid probes based on specific displacement hybridization", Nucleic Acids Res., vol. 30, No. 2 e5, pp. 1-9 (2002).
Nazarenko, I. A., et al., "A closed tube format for amplification and detection of DNA based on energy transfer", Nucleic Acids Res., vol. 25, No. 12, pp. 2516-2521 (1997).
Nordström, T., et al., "Method Enabling Pyrosequencing on Double-Stranded DNA", Anal. Biochem., vol. 282, pp. 186-193 (2000).
Pierce, K. E., et al., "Detection of cystic fibrosis alleles from single cells using molecular beacons and a novel method of asymmetric real-time PCR", Molecular Human Reproduction (2003) vol. 9, Issue 12, pp. 815-820.
Pierce, K. E., et al., "Linear-After-The-Exponential (LATE)-PCR: Primer design criteria for high yields of specific single-stranded DNA and improved real-time detection", PNAS, vol. 102, No. 24, pp. 8609-8614 (2005).
Pierce, K. E., et al., "QuantiLyse™: Reliable DNA Amplification from Single Cells", BioTechniques, vol. 32, pp. 1106-1111 (2002).
Sanchez, J. A., et al., "Linear-After-The-Exponential (LATE)-PCR: An advanced method of asymmetric PCR and its uses in quantitative real-time analysis", PNAS, vol. 101, No. 7, pp. 1933-1938 (2004).
Santalucia, Jr., J., "A unified view of polymer, dumbbell, and oligonucleotide DNA nearest-neighbor thermodynamics", Proc. Natl. Acad. Sci., vol. 95, pp. 1460-1465 (1998).
Tyagi, S., et al., "Wavelength-shifting molecular beacons", Nature Biotechnology, vol. 18, pp. 1191-1196 (2000).
Wetmur, J. G., "DNA Probes: Applications of the Principles of Nucleic Acid Hybridization", Critical Rev. in Biochem. & Mole. Biol., vol. 26, No. 3/4, pp. 227-259 (1991).
Whitcombe, D., "Detection of PCR products using self-probing amplicons and fluorescence", Nature Biotechnology, vol. 17, pp. 804-807 (1999).
Wittwer, C. T., et al., "High-Resolution Genotyping by Amplicon Melting Analysis Using LCGreen", Clin. Chem., vol. 49, No. 6, pp. 853-860 (2003).
Wittwer, C. T., et al., "Real-Time Multiplex PCR Assays", Methods, vol. 25, pp. 430-442 (2001).
Zuker, M., "Mfold web server for nucleic acid folding and hybridization prediction", Nucleic Acids Res., vol. 31, No. 13, pp. 3406-3415 (2003).
Cane, Patricia A. et al., "Use of Real-Time PCR and Fluorimetry to Detect Lamivudine Resistance-Associated Mutations in Hepatitis B Virus", Antimicrobial Agents and Chemotherapy, Jul. 1999, vol. 43, No. 7, pp. 1600-1608.
Wittwer, Carl. T. et al., "Continuous Fluorescence Monitoring of Rapid Cycle DNA Amplification", Bio Techniques, Jan. 1997, vol. 22, No. 1, pp. 130-138.
Supplementary Partial European Search Report dated Jun. 12, 2008 from counterpart European Application No. 05810422.5 (12 pgs.).
Howell et al., "iFRET: An improved fluorescence system for DNA-melting analysis," Genome Research (2002) 12: 1401-1407.
Oliver et al., "Use of Single Nucleotide Polymorphisms (SNP) and Real-Time Polymerase Chain Reaction for Bone Marrow Engraftment Analysis," Journal of Molecular Diagnostics (2000) 2(4): 202-208.

\* cited by examiner

SEQ ID NO: 40

SEQ ID NO: 40

SEQ ID NO: 40

SEQ ID NO:43

ACACT CCTG G CCAC T T TG TC C TGGGG A C CAGGT A AGAA TGTGAT TGTCTG

SEQ ID NO:44

TG TGGCCAGG AG TG TCAAAC TG TG C A AG CACACG G ATACGGGG G AG C C G T

SEQ ID NO:45

ACACT GGTG G GGAGAGT T T G T GGT GGG GG AGCAGG T A AG AAT G AT GT GT G

SEQ ID NO:46

TGT GGC CAG G AG TGT CA A ACT CTG C A AG CACACG G AT AC C CG G AG GCGT

A SEQ ID NO:47
C T TG TA A G CA T GG GG A G GG G G T T T T GA T G T G GA T C G

B SEQ ID NO:48
TA AN NAG ACA GA G NAGA N C GAG G NA GA GA A G GG G GN GN G NN GATATA AGAGA T AA T N N AAT ATA

C SEQ ID NO:49
C T TG TA A G CA T GGG GA G GG GG T T TCT GA T G TGGA TT G C

D SEQ ID NO:50
A A A TC T C CA C C A A A C C C CC C C C NAC C C CC CG C T TG CN NAG G C C A

SEQUENCE LISTING

<160> NUMBER OF SEQ ID NOS: 51

<210> SEQ ID NO 1
<211> LENGTH: 22
<212> TYPE: DNA
<213> ORGANISM: Artificial sequence
<220> FEATURE:
<223> OTHER INFORMATION: Synthetic

<400> SEQUENCE: 1

-continued aatactggat aggaccacga gg　　　　　　　　　　　　　　　　　　　　　　22

<210> SEQ ID NO 2
<211> LENGTH: 22
<212> TYPE: DNA
<213> ORGANISM: Artificial sequence
<220> FEATURE:
<223> OTHER INFORMATION: Synthetic

<400> SEQUENCE: 2
ctggatagga ccacgaggcc ag　　　　　　　　　　　　　　　　　　　　　　22

<210> SEQ ID NO 3
<211> LENGTH: 16
<212> TYPE: DNA
<213> ORGANISM: Artificial sequence
<220> FEATURE:
<223> OTHER INFORMATION: Synthetic

<400> SEQUENCE: 3
gcatgtcttg tggtgg　　　　　　　　　　　　　　　　　　　　　　　　　16

<210> SEQ ID NO 4
<211> LENGTH: 22
<212> TYPE: DNA
<213> ORGANISM: Artificial sequence
<220> FEATURE:
<223> OTHER INFORMATION: Synthetic

<400> SEQUENCE: 4
taacaagcag agtccctctg gt　　　　　　　　　　　　　　　　　　　　　　22

<210> SEQ ID NO 5
<211> LENGTH: 15
<212> TYPE: DNA
<213> ORGANISM: Artificial sequence
<220> FEATURE:
<223> OTHER INFORMATION: Synthetic

<400> SEQUENCE: 5
gggaccaggt aagaa　　　　　　　　　　　　　　　　　　　　　　　　　15

<210> SEQ ID NO 6
<211> LENGTH: 24
<212> TYPE: DNA
<213> ORGANISM: Artificial sequence
<220> FEATURE:
<223> OTHER INFORMATION: Synthetic

<400> SEQUENCE: 6
ccgcccttct ctctgcccccc tggt　　　　　　　　　　　　　　　　　　　　24

<210> SEQ ID NO 7
<211> LENGTH: 22
<212> TYPE: DNA
<213> ORGANISM: Artificial sequence
<220> FEATURE:
<223> OTHER INFORMATION: Synthetic

<400> SEQUENCE: 7
gccaggggtt ccactacgta ga　　　　　　　　　　　　　　　　　　　　　　22

<210> SEQ ID NO 8
<211> LENGTH: 18
<212> TYPE: DNA

```
<213> ORGANISM: Artificial sequence
<220> FEATURE:
<223> OTHER INFORMATION: Synthetic

<400> SEQUENCE: 8
ctggtacctg aaccgtat                                                      18

<210> SEQ ID NO 9
<211> LENGTH: 12
<212> TYPE: DNA
<213> ORGANISM: Homo sapiens

<400> SEQUENCE: 9
atcctatggc cc                                                            12

<210> SEQ ID NO 10
<211> LENGTH: 26
<212> TYPE: DNA
<213> ORGANISM: Artificial sequence
<220> FEATURE:
<223> OTHER INFORMATION: Synthetic

<400> SEQUENCE: 10
ggccatcact aaaggcaccg agcact                                             26

<210> SEQ ID NO 11
<211> LENGTH: 27
<212> TYPE: DNA
<213> ORGANISM: Artificial sequence
<220> FEATURE:
<223> OTHER INFORMATION: Synthetic

<400> SEQUENCE: 11
gggtttctga tacgcactga ctctctc                                            27

<210> SEQ ID NO 12
<211> LENGTH: 18
<212> TYPE: DNA
<213> ORGANISM: Artificial sequence
<220> FEATURE:
<223> OTHER INFORMATION: Synthetic

<400> SEQUENCE: 12
gaccaccagc agcctaag                                                      18

<210> SEQ ID NO 13
<211> LENGTH: 14
<212> TYPE: DNA
<213> ORGANISM: Artificial sequence
<220> FEATURE:
<223> OTHER INFORMATION: Synthetic

<400> SEQUENCE: 13
ggtgggaaaa taga                                                          14

<210> SEQ ID NO 14
<211> LENGTH: 40
<212> TYPE: DNA
<213> ORGANISM: Artificial sequence
<220> FEATURE:
<223> OTHER INFORMATION: Synthetic

<400> SEQUENCE: 14
cgcggcgtca ggcatatagg ataccgggac agacgccgcg                              40
```

```
<210> SEQ ID NO 15
<211> LENGTH: 26
<212> TYPE: DNA
<213> ORGANISM: Artificial sequence
<220> FEATURE:
<223> OTHER INFORMATION: Synthetic

<400> SEQUENCE: 15
ggtcagcgcc gggctgcaag tgtaga                                        26

<210> SEQ ID NO 16
<211> LENGTH: 23
<212> TYPE: DNA
<213> ORGANISM: Artificial sequence
<220> FEATURE:
<223> OTHER INFORMATION: Synthetic

<400> SEQUENCE: 16
gatgggtgga gcttgtcttg agg                                           23

<210> SEQ ID NO 17
<211> LENGTH: 26
<212> TYPE: DNA
<213> ORGANISM: Artificial sequence
<220> FEATURE:
<223> OTHER INFORMATION: Synthetic

<400> SEQUENCE: 17
cgaggtcatt gaatacgcac ggctcc                                        26

<210> SEQ ID NO 18
<211> LENGTH: 22
<212> TYPE: DNA
<213> ORGANISM: Artificial sequence
<220> FEATURE:
<223> OTHER INFORMATION: Synthetic

<400> SEQUENCE: 18
taacaagcag agtccctctg gt                                            22

<210> SEQ ID NO 19
<211> LENGTH: 15
<212> TYPE: DNA
<213> ORGANISM: Artificial sequence
<220> FEATURE:
<223> OTHER INFORMATION: Synthetic

<400> SEQUENCE: 19
gggaccaggt aagaa                                                    15

<210> SEQ ID NO 20
<211> LENGTH: 14
<212> TYPE: DNA
<213> ORGANISM: Artificial sequence
<220> FEATURE:
<223> OTHER INFORMATION: Synthetic

<400> SEQUENCE: 20
tgctaatggt ggag                                                     14

<210> SEQ ID NO 21
<211> LENGTH: 28
<212> TYPE: DNA
<213> ORGANISM: Artificial sequence
<220> FEATURE:
<223> OTHER INFORMATION: Synthetic
```

<400> SEQUENCE: 21
gcccggagcg aggagagtag cactcttg                                    28

<210> SEQ ID NO 22
<211> LENGTH: 26
<212> TYPE: DNA
<213> ORGANISM: Artificial sequence
<220> FEATURE:
<223> OTHER INFORMATION: Synthetic

<400> SEQUENCE: 22
caccagtctt gtaaaccgga gatgaa                                      26

<210> SEQ ID NO 23
<211> LENGTH: 33
<212> TYPE: DNA
<213> ORGANISM: Artificial sequence
<220> FEATURE:
<223> OTHER INFORMATION: Synthetic

<400> SEQUENCE: 23
gtatgggagt gggaggggaa ataatgtgt tag                               33

<210> SEQ ID NO 24
<211> LENGTH: 26
<212> TYPE: DNA
<213> ORGANISM: Artificial sequence
<220> FEATURE:
<223> OTHER INFORMATION: Synthetic

<400> SEQUENCE: 24
aggtctatca ccctattaac cactca                                      26

<210> SEQ ID NO 25
<211> LENGTH: 30
<212> TYPE: DNA
<213> ORGANISM: Artificial sequence
<220> FEATURE:
<223> OTHER INFORMATION: Synthetic

<400> SEQUENCE: 25
caccagtctt gtaaaccgga gatgaaaacc                                  30

<210> SEQ ID NO 26
<211> LENGTH: 19
<212> TYPE: DNA
<213> ORGANISM: Artificial sequence
<220> FEATURE:
<223> OTHER INFORMATION: Synthetic

<400> SEQUENCE: 26
cgaggagagt agcactctt                                              19

<210> SEQ ID NO 27
<211> LENGTH: 30
<212> TYPE: DNA
<213> ORGANISM: Artificial sequence
<220> FEATURE:
<223> OTHER INFORMATION: Synthetic

<400> SEQUENCE: 27
aggtctatca ccctattaac cactcacggg                                  30

<210> SEQ ID NO 28
<211> LENGTH: 23

<212> TYPE: DNA
<213> ORGANISM: Artificial sequence
<220> FEATURE:
<223> OTHER INFORMATION: Synthetic

<400> SEQUENCE: 28 ggagggaaa ataatgtgtt agt         23

<210> SEQ ID NO 29
<211> LENGTH: 27
<212> TYPE: DNA
<213> ORGANISM: Artificial sequence
<220> FEATURE:
<223> OTHER INFORMATION: Synthetic

<400> SEQUENCE: 29
caatcccttg acctgttgtg gagagaa         27

<210> SEQ ID NO 30
<211> LENGTH: 28
<212> TYPE: DNA
<213> ORGANISM: Artificial sequence
<220> FEATURE:
<223> OTHER INFORMATION: Synthetic

<400> SEQUENCE: 30
tccccagagc ccagccggtg tcattttc         28

<210> SEQ ID NO 31
<211> LENGTH: 17
<212> TYPE: DNA
<213> ORGANISM: Artificial sequence
<220> FEATURE:
<223> OTHER INFORMATION: Synthetic

<400> SEQUENCE: 31
cttcagctca aacaata         17

<210> SEQ ID NO 32
<211> LENGTH: 21
<212> TYPE: DNA
<213> ORGANISM: Artificial sequence
<220> FEATURE:
<223> OTHER INFORMATION: Synthetic

<400> SEQUENCE: 32
cgctataatg aaattatagc g         21

<210> SEQ ID NO 33
<211> LENGTH: 24
<212> TYPE: DNA
<213> ORGANISM: Artificial sequence
<220> FEATURE:
<223> OTHER INFORMATION: Synthetic

<400> SEQUENCE: 33
tggctggaca cctggcttca gact         24

<210> SEQ ID NO 34
<211> LENGTH: 18
<212> TYPE: DNA
<213> ORGANISM: Artificial sequence
<220> FEATURE:
<223> OTHER INFORMATION: Synthetic

<400> SEQUENCE: 34
caacttgggg gactaggc    18

<210> SEQ ID NO 35
<211> LENGTH: 28
<212> TYPE: DNA
<213> ORGANISM: Artificial sequence
<220> FEATURE:
<223> OTHER INFORMATION: Synthetic

<400> SEQUENCE: 35
ggtcgtacag gaaaagatgg cggctcaa    28

<210> SEQ ID NO 36
<211> LENGTH: 22
<212> TYPE: DNA
<213> ORGANISM: Artificial sequence
<220> FEATURE:
<223> OTHER INFORMATION: Synthetic

<400> SEQUENCE: 36
tgaaagaaac cactagaggg ca    22

<210> SEQ ID NO 37
<211> LENGTH: 30
<212> TYPE: DNA
<213> ORGANISM: Artificial sequence
<220> FEATURE:
<223> OTHER INFORMATION: Synthetic

<400> SEQUENCE: 37
ccgcctggga tggcatactg tggaaggcgg    30

<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38
cgttataatg aaattataac g    21

<210> SEQ ID NO 39
<211> LENGTH: 11
<212> TYPE: DNA
<213> ORGANISM: Artificial sequence
<220> FEATURE:
<223> OTHER INFORMATION: Synthetic

<400> SEQUENCE: 39
gatctatctg c    11

<210> SEQ ID NO 40
<211> LENGTH: 22
<212> TYPE: DNA
<213> ORGANISM: Homo sapiens

<400> SEQUENCE: 40
cgtgtataga ctatactagc ag    22

<210> SEQ ID NO 41
<211> LENGTH: 51
<212> TYPE: DNA
<213> ORGANISM: Artificial sequence
<220> FEATURE:
<223> OTHER INFORMATION: Synthetic

<400> SEQUENCE: 41
agcaggtggt aggagcattg ctcgggctgc ctcaagacaa gctccaccca t    51

<210> SEQ ID NO 42
<211> LENGTH: 48
<212> TYPE: DNA
<213> ORGANISM: Artificial sequence
<220> FEATURE:
<223> OTHER INFORMATION: Synthetic

<400> SEQUENCE: 42
gcagcagctg tagatgcatg ctcgcgtgct cagagagcag ctcacact    48

<210> SEQ ID NO 43
<211> LENGTH: 50
<212> TYPE: DNA
<213> ORGANISM: Homo sapiens

<400> SEQUENCE: 43
acactgctgg ccacactttg tccygggggac caggtaagaa tgattgyctg    50

<210> SEQ ID NO 44
<211> LENGTH: 50
<212> TYPE: DNA
<213> ORGANISM: Homo sapiens

<400> SEQUENCE: 44
tgtggccagg agtgtcaaac tctgcaagca cacggatacc cgggagccgt    50

<210> SEQ ID NO 45
<211> LENGTH: 49
<212> TYPE: DNA
<213> ORGANISM: Homo sapiens

<400> SEQUENCE: 45
acactcctgg ccagactttg tcctggggac caggtaagaa tgatgtctg    49

<210> SEQ ID NO 46
<211> LENGTH: 50
<212> TYPE: DNA
<213> ORGANISM: Homo sapiens

<400> SEQUENCE: 46
tgtggccagg agtgtcaaac tctgcaagca cacggatacc ccggagccgt    50

<210> SEQ ID NO 47
<211> LENGTH: 36
<212> TYPE: DNA
<213> ORGANISM: Artificial sequence
<220> FEATURE:
<223> OTHER INFORMATION: Synthetic

<400> SEQUENCE: 47
cttgtaagca tggggagggg gttttgatgt ggatcg    36

<210> SEQ ID NO 48
<211> LENGTH: 64
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(64)

```
<223> OTHER INFORMATION: n = A, T, C or G

<400> SEQUENCE: 48
taannagaca gagnagancg aggnagagaa gggggngngn ngatataaga gataatnnaa      60
tata                                                                  64

<210> SEQ ID NO 49
<211> LENGTH: 38
<212> TYPE: DNA
<213> ORGANISM: Artificial sequence
<220> FEATURE:
<223> OTHER INFORMATION: Synthetic

<400> SEQUENCE: 49
cttgtaagca tggggagggg gtttctgatg tggattgc                             38

<210> SEQ ID NO 50
<211> LENGTH: 44
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(44)
<223> OTHER INFORMATION: n = A, T, C or G

<400> SEQUENCE: 50
aaatctccac caaacccccc ccnacccccc gcttgcnnag gcca                      44

<210> SEQ ID NO 51
<211> LENGTH: 10
<212> TYPE: DNA
<213> ORGANISM: Artificial sequence
<220> FEATURE:
<223> OTHER INFORMATION: Synthetic

<400> SEQUENCE: 51 aatgrcttta                                                            10
```

METHODS FOR SEQUENTIAL DNA AMPLIFICATION AND SEQUENCING

CROSS-REFERENCE TO RELATED APPLICATIONS

This application is a division of U.S. patent application Ser. No. 12/292,038 filed Nov. 10, 2008, now abandoned, which is a division of U.S. patent application Ser. No. 11/252,433 filed Oct. 17, 2005, now U.S. Pat. No. 7,632,642, which claims priority to U.S. Provisional Application 60/619,654 filed Oct. 18, 2004, each of which are herein incorporated by reference in their entireties.

TECHNICAL FIELD

This invention relates to nucleic acid amplification reactions, including amplifications utilizing the polymerase chain reaction, and assays utilizing such reactions in combination with sequencing and hybridization probe detection methods.

BACKGROUND

Nucleic acid amplification techniques and assays are well known. Some amplification reactions are isothermal, such as nucleic acid sequence based amplification (NASBA). Others employ thermal cycling, such as the polymerase chain reaction (PCR). Preferred amplification assays employing fluorescence detection of amplified product are homogeneous, that is, they do not require the physical separation of reagents to permit detection (for example, separation of bound probes from unbound probes) and can be performed in a single closed vessel. Such assays may be end-point, wherein product is detected after amplification, or they may be real-time, wherein product is detected as amplification proceeds.

Nucleic acid amplification and assays employing PCR are described, for example, in U.S. Pat. Nos. 4,683,202, 4,683,195 and 4,965,188, and, generally, PCR PROTOCOLS, a guide to Methods and Applications, Innis et al. eds., Academic Press (San Diego, Calif. (USA) 1990). Homogeneous PCR assays, including real-time assays, in which amplified product is detected during some or all of the PCR cycles as the reaction proceeds are described, for example, in U.S. Pat. Nos. 5,994,056, 5,487,972, 5,925,517 and 6,150,097.

PCR amplification reactions generally are designed to be symmetric, that is, to make double-stranded amplicons exponentially by utilizing forward primer and reverse primer in equimolar concentrations and equal melting temperatures ($T_m$'s). A technique that has found limited use for making single-stranded DNA directly in a PCR reaction is "asymmetric PCR." Gyllensten and Erlich, "Generation of Single-Stranded DNA by the Polymerase Chain Reaction and Its Application to Direct Sequencing of the HLA-DQA Locus," Proc. Natl. Acad. Sci. (USA) 85: 7652-7656 (1988); and U.S. Pat. No. 5,066,584. Asymmetric PCR is a non-symmetric PCR amplification method that differs from symmetric PCR in that one of the primers is diluted fivefold to one hundredfold so as to be present in limiting amount of 1-20 percent of the concentration of the other primer. As a consequence, the amplification consists of an exponential phase in which both primers are extended, generating double-stranded product, or amplicon, followed by a linear amplification in which only one primer remains, generating single-stranded amplicon.

More recently we have developed a non-symmetric PCR amplification method known as "Linear-After-The-Exponential" PCR or, for short, "LATE-PCR." LATE-PCR is a non-symmetric PCR amplification consisting of an exponential phase in which both primers are annealed and extended followed by a linear phase after exhaustion of the Limiting Primer, when only the Excess Primer is annealed and extended. See Sanchez et al. (2004) Proc. Natl. Acad. Sci. (USA) 101: 1933-1938, published international patent application WO 03/054233 (3 Jul. 2003), and Pierce et al. (2005) Proc. Natl. Acad. Sci (USA) 102: 8609-8614, all of which are incorporated herein by reference in their entirety.

A convenient and inexpensive method for monitoring double-stranded amplicon production in a PCR amplification is to use a dye that fluoresces upon intercalating into or otherwise interacting with double-stranded DNA, such as SYBR Green I or SYBR Gold. See, for example, U.S. Pat. No. 5,994,056. Melting temperature analysis of amplicons performed either in real time during a PCR amplification or performed after amplification is used for product identification. One problem with utilizing such melting temperature analysis is that dye fluorescence is a function of amplicon size. Another problem is that dyes redistribute from amplification products, or amplicons, having low melting temperatures to amplicons having higher melting temperatures during analysis, thereby distorting results. Two approaches to solve these problems have been advanced. One approach, G quenching, imposes severe restrictions on primer design and causes large background fluorescence (Crockett A O, Wittwer C T. "Fluorescein-Labeled Oligonucleotides for Real-Time PCR: Using the Inherent Quenching of Deoxyguanosine Nucleotides" Anal. Biochem. 290:89-97 (2001)). The other, replacing SYBR dyes with LC Green dye, yields very small percentage of signal for sequences not present in abundance and requires highly specialized software and hardware (Wittwer et al. High-Resolution Genotyping by Amplicon Melting Analysis Using LCGreen," Clin. Chem. 49:853-860 (2003).

Fluorescent-labeled probes are used in homogeneous nucleic acid amplification assays, including PCR assays, to measure the accumulation of desired amplicon, either in real time or by end-point analysis. Several available types of probes are significantly allele-discriminating as compared to linear single-stranded probes. Real-time probes include dual-labeled linear probes that are cleaved by 5'-to-3' exonuclease activity of DNA polymerase during the extension step of a PCR cycle (see U.S. Pat. Nos. 5,210,015, 5,487,972 and 5,538,848); molecular beacon probes (see U.S. Pat. Nos. 5,925,517, 6,103,476 and 6,365,729); minor groove binding probes (see Afonina et al. "Minor Groove Binder-Conjugated DNA Probes for Quantitative DNA Detection by Hybridization-Triggered Fluorescence," Biotechniques 32: 946-949 (2002)); linear probe pairs that FRET when hybridized adjacently on a target strand; quenched double-stranded linear probes for which a target competes to hybridize to the labeled probe strand (see Li, Q. et al. (2002), Nucl. Acid. Res. 30: e5); and so-called "light-up" probes, which are peptide nucleic acid (PNA) oligomers linked to an asymmetric cyanine dye that fluoresces when the probe binds to target to form a double-stranded region. For LATE-PCR we have utilized low-temperature allele-discriminating probes, such as low temperature molecular beacon probes (See WO 03/045233). Labeled oligonucleotide probes may be attached to primers by linkers such that during amplification the probes are not copied but are free to hybridize to a target sequence resulting from extension of the primer. Examples are Scorpions®, primers to which are attached molecular beacon probes, and Anglers®, primers to which are attached fluorophore-labeled linear probes. Lee, M. A. et al. (2002), Analytica Clinica Acta 457: 61:70; Whitcombe, D. et al. (1999), Nature Biotechnology 17: 804-807. The probe portion of such composite structures, which carries the fluorescent label, hybridizes separately from the primer portion. They are, thus, labeled probes and not labeled primers, as those terms are used herein. Target-specific probes lack the capacity to monitor total production of double-stranded products, however.

Certain probes are mismatch-tolerant. Mismatch-tolerant probes hybridize with and generate detectable signal for more than one target sequence at a detection temperature in an assay, and various hybrids so formed will have different melting points. Linear, or random coil, single-stranded probes are generally mismatch tolerant. Examples of such probes are linear probes with an internal fluorescent moiety whose level of fluorescence increases upon hybridization to one or another target strand; fluorescently labeled linear probes used in combination with SYBR Gold and SYBR Green I dyes, such that fluorescence of the label occurs by FRET from the dye when the probe hybridizes to one or another target (see U.S. patent publication US 2002/0119450, 28 Aug. 2002), so-called "sloppy beacons", and variations of linear probe pairs that FRET (see U.S. Pat. No. 6,472,156).

Utilizing multiple probes that each bind only to one possible target amplicon generated in an amplification reaction creates a problem for analyzing complicated reaction mixtures or for detecting one or a few targets from among numerous possible targets. Available fluorescence detection permits resolution of a limited number of fluorophores, generally no more than eight. Limited multiplexing is possible, for example, by designing a different allele-discriminating molecular beacon probe for each target and labeling each probe differentially. (See, for example, Tyagi et al. (2000) Nature Biotechnology 18: 1191-1196). Mixtures of allele-discriminating probes, each comprising aliquots of multiple colors, extends the number of probe signatures and works well if only one of many (at least up to 56) targets is actually present, but it encounters ambiguous results if more than one target is present.

There are many situations that involve complex targets or one among many possible targets. Several schemes have been developed or proposed for such situations, but all have serious drawbacks and limitations. Tyagi et al. published international patent application WO 01/31062, have described a technique sometimes referred to as "sloppy beacons," which are molecular beacon probes that have long loop sequences, rendering them mismatch tolerant and able to bind to some extent to multiple targets at the annealing temperature of a PCR amplification reaction. Such probes suffer from poor reaction kinetics against mismatched targets and are likely to remain hybridized to perfectly matched targets at the extension temperature of a PCR amplification and be cleaved by Taq DNA polymerase. Further, only an indirect indication of melting temperatures of probe-target hybrids under the assay conditions is obtained, and that assumes equilibrium has been achieved. Real-time multiplexing in symmetric PCR amplifications with FRET probes has been described. In order not to interfere with amplification, the melting temperatures of all probe-target hybrids are constrained to be in the narrow temperature range between the primer annealing temperature and the primer extension temperature. Also, that scheme is not quantitative. Post-amplification multiprobe assays employing FRET probes of different colors have been disclosed Wittwer et al., "Real-Time Multiplex PCR Assays, Methods" 25:430-442 (2001). The reaction mixture following a symmetric PCR amplification is rapidly chilled, then slowly heated to determine melting curves for the various fluorophores present. This approach is not quantitative. In addition, because of large scatter among replicate symmetric PCR amplifications, end-point assays in general tend to be only qualitative.

Sequencing reaction products provides an alternative to probing. Traditional dideoxy sequencing may utilize products of amplification reactions, such as symmetric PCR or LATE-PCR, as starting materials for cycle sequencing. Amplified product is purified utilizing ethanol precipitation or an affinity column to remove leftover dNTPs and primers, subjected to a cycle sequencing reaction utilizing one sequencing primer and fluorescently labeled dideoxy nucleotides, and subjected to capillary gel electrophoresis. "Pyrosequencing" is a real-time, isothermal, sequence-by-synthesis method known in the art. If exponential amplification methods, for example PCR, are used in the preparation of starting material for Pyrosequencing, amplified product must be cleaned up by isolation of single-stranded product as well as removal of dNTPs, pyrophosphate and unincorporated primers from the amplification reaction. LATE-PCR simplifies sample preparation, because it generates primarily single-stranded product, but it does not in and of itself eliminate the need to clean-up the product.

An aspect of this invention is methods for homogeneous detection of reaction products of amplification reactions, temperature cycling or isothermal, utilizing the detection of fluorescence from fluorophore-labeled linear oligonucleotide primers excited indirectly by exciting a DNA fluorescent dye such as SYBR Green I or, preferably, SYBR Gold. Such dyes become fluorescent when they associate with double-stranded DNA, into which they are reported to intercalate. The foregoing methods may be performed in real time or following the amplification reaction, either by reading fluorescence at a detection temperature (end-point detection) or by ascertaining changes in fluorescence as a function of temperature by post-amplification melting analysis. As a reaction mixture is heated through the melting temperatures of various reaction products, fluorescence decreases progressively as various amplicons containing a particular fluorophore-containing primer reach their melting temperatures and become single-stranded. Preferred methods include calculating the ratio of primer signal to dye signal.

Another aspect of this invention is reagent kits that include both DNA fluorescents dye and at least one such labeled primer, preferably as part of a primer pair, and optionally amplification reagents.

Yet other aspects of this invention are homogeneous methods for detecting reaction products of LATE-PCR reactions employing a low-temperature detection step. Certain embodiments comprise including in the reaction mixture at least one allele-discriminating probe according to this invention, namely, a quenched double-stranded probe generally of the type described by Li, Q. et al. (2002) Nucl. Acids Res. 30: e5 except that it is a low temperature (Low-$T_m$, or Super-Low $T_m$) target-specific probe and that it is excited indirectly by exciting a DNA fluorescent dye intercalated into the probe-target hybrid such as, preferably, SYBR Gold. Other embodiments comprise including in the reaction mixture at least one indirectly excitable mismatch-tolerant probe according to this invention, namely, a quenched single-stranded probe generally of the type described by Lee and Furst United States published patent application Pub. No. US 2002/0119450 except that is a quenched low-temperature probe. These various methods include exciting the dye during the low-temperature detection steps of a LATE-PCR amplification and detecting fluorescence from the probes under these conditions to provide a measure of the target single-stranded sequence. Particular embodiments may further include measuring the total amount of double-stranded product(s) in the reaction mixture by detecting dye fluorescence, preferably during or at the end of the extension step of PCR cycles while the temperature of the reaction mixture is above the melting temperature(s) of the probes. Certain preferred methods include calculating the ratio of probe signal to dye signal. In the case of replicate samples, such ratio corrects for differences among replicate samples in amplification yields known to occur in PCR amplifications.

Other aspects of this invention are such low-temperature allele-discriminating and quenched mismatch-tolerant probes, LATE-PCR kits that include at least one such low-temperature target-specific probe together with amplification reagents and preferably the fluorescent DNA dye; and oligonucleotide sets comprising LATE-PCR primers and at least one such probe.

Other aspects of this invention are homogeneous detection methods for use when multiple amplicons are present or may be present, such method comprising including in a LATE-PCR amplification reaction mixture one or more low-temperature mismatch-tolerant detection probes that, because of their low $T_m$, do not interfere with amplification and are not hydrolysed (cut) by a DNA polymerase having 5'-3' exonuclease activity, and that emit a fluorescent signal when hybridized and excited, either directly by a suitable excitation source or indirectly by a fluorescent DNA dye that is excited by a suitable excitation source. Such methods include single-probe assays and multiple-probe assays for applications such as genotyping. More than one probe may be labeled with the same fluorophore, in which event discrimination relies on change in fluorescence with temperature, just as when a single probe is used. Probes may be labeled with different fluorophores, in which event color difference is also used for discrimination. Discrimination among targets for purposes of identification and quantification may include fluorescence ratios between fluorophores at the same or different temperatures, as well as fluorophore-to-dye ratios. Detection is preferably performed during the amplification (real time) and more preferably during a low-temperature detection step included in a LATE-PCR amplification protocol, and the detection step may include detection at multiple temperatures. Yet another aspect of this invention is a single-stranded linear probe useful in such detection methods, such probe being of the type described in U.S. patent application publication U.S. 2002/0119450 (29 Aug. 2002), that is, a probe excited by the fluorescence emission from a fluorescent DNA dye, except that it is a low-temperature (Low-$T_m$ or Super-Low-$T_m$) probe, is mismatch-tolerant, and includes a quenching moiety that quenches the fluorescence, which otherwise would result from secondary structure of at low temperature.

Another aspect of this invention is an amplification-through-sequencing method that permits the product of a LATE-PCR amplification to be prepared for pyrosequencing in the amplification reaction chamber, vessel, well, slide or container, a "single-tube" operation, which may be utilized with LATE-PCR amplifications performed in small volumes, preferably 17 ul or less.

Another aspect of this invention is a method for preparing LATE-PCR products for dideoxy sequencing utilizing only post-amplification aqueous dilution of amplification reaction mixtures, which may be performed as a "single-tube" operation.

SUMMARY

In this application references are made to melting temperatures, $T_m$, of nucleic acid primers, probes and amplicons. $T_m$, means the temperature at which half of the subject material exists in double-stranded form and the remainder is single stranded. Generally, except for LATE-PCR, the $T_m$, of a primer is a calculated value using either the "% GC" method (Wetmar, J. G. (1991) "DNA Probes: Applications of the Principles of Nucleic Acid Hybridization," Crit. Rev. Biochem. Mol. Biol. 26: 227-259) or the "2(A+T) plus 4(G+C)" method, both of which are well known, at a standard condition of primer and salt concentration. LATE-PCR, however, takes into account the actual primer melting temperatures in a particular reaction, taking into account primer concentrations at the start of amplification. See Sanchez et al. (2004) PNAS (USA) 101: 1933-1938, and Pierce et al. (2005) Proc. Natl. Acad. Sci (USA) 102: 8609-8614.

In this application we refer to such a concentration-adjusted melting temperature at the start of amplification as $T_{m[0]}$, which can be determined empirically, as is necessary when non-natural nucleotides are used, or calculated according to the "nearest neighbor" method (Santa Lucia, J. (1998), PNAS (USA) 95: 1460-1465; and Allawi, H. T. and Santa Lucia, J. (1997), Biochem. 36: 10581-10594) using a salt concentration adjustment, which in the examples below was 0.07 M monovalent cation concentration. LATE-PCR may also take into account the melting temperature of the amplicon, which is calculated utilizing the formula: $T_m=81.5+0.41(\% G+\% C)-500/L+16.6 \log [M]/(1+0.7 [M])$, where L is the length in nucleotides and [M] is the molar concentration of monovalent cations. Melting temperatures of linear, or random-coil, probes are calculated as for primers. Melting temperatures of structured probes, for example molecular beacon probes, can be determined empirically.

As used in this application, "LATE-PCR" means a non-symmetric DNA amplification employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon, wherein the concentration-adjusted melting temperature of the Limiting Primer at the start of amplification, $T_{m[0]}^L$, is not more than 5° C. below the concentration-adjusted melting temperature of the Excess Primer at the start of amplification, $T_{m[0]}^X$, preferably at least as high and more preferably 3-10° C. higher; and wherein thermal cycling is continued for multiple cycles after exhaustion of the Limiting Primer to produce single-stranded product, namely, the extension product of the Excess Primer, sometimes referred to as the "Excess Primer Strand".

Primers and probes of this invention or useful in methods and kits of this invention are oligonucleotides in the broad sense, by which is meant that they may be DNA, RNA, mixtures of DNA and RNA, and they may include non-natural nucleotides (for example, 2' o-methyl ribonucleotides) and non-natural internucleotide linkages (for example, phosphorothioate linkages). Both primers and probes function in part by hybridizing to a sequence of interest in a reaction mixture. A primer is a single-stranded oligonucleotide that can hybridize to its complementary sequence at the primer annealing temperature of an amplification reaction and be extended at its 3' end by a DNA polymerase. A primer of this invention is a primer that signals hybridization of its priming sequence by means of a fluorophore that is indirectly excitable. A probe of this invention or useful in methods and kits of this invention is or includes a single-stranded oligonucleotide that can hybridize to its intended target sequence (or sequences) at the detection temperature (or temperatures) in or following an amplification reaction and fluorescently signal that hybridization event by means of a fluorophore that is indirectly excitable. As used herein a "probe" is not extended in the amplification reaction by a DNA polymerase. Probes that are very specific for a perfectly complementary target sequence and strongly reject closely related sequences having one or a few mismatched bases are "allele discriminating." Probes that hybridize under at least one applicable detection condition not only to perfectly complementary sequences but also to partially complementary sequences having one or more mismatched bases are "mismatch tolerant" probes.

"Fluorescent DNA dye" as used herein means a composition, for example SYBR Green I or SYBR Gold, that becomes fluorescently excitable when it associates with double-stranded DNA. It has been reported that fluorescent DNA dyes intercalate into double-stranded DNA, but we do not wish to be bound by any theory of operation.

Primers of this invention are used in conjunction with a fluorescent DNA dye and are linear single-stranded oligonucleotides labeled with a fluorophore that is indirectly excitable, that is, when the primer hybridizes to a template strand in the reaction mixture to form a region of double-stranded DNA, and light (usually but not necessarily visible light) of a wavelength that excites, or is absorbed by, the DNA fluorescent dye but not the fluorophore is shone on the sample, the fluorophore emits. It has been reported that energy transfers from a fluorescent DNA dye to a nearby fluorophore by fluorescence resonance energy transfer (FRET), but we do not wish to be bound by any theory of operation. We refer to a fluorophore that emits in this circumstance as a fluorophore that is "indirectly excited." Probes of this invention are likewise used in conjunction with a fluorescent dye that binds to double-stranded DNA (a "fluorescent DNA dye") and labeled with such an indirectly excitable fluorophore such that when the probe hybridizes to a target strand in the reaction mixture and the dye is excited, the fluorophore emits.

As used herein "kit" means a collection of reagents for performing an amplification or assay. A kit may be "complete", that is, include all reagents needed for all steps of an amplification or amplification-detection. Alternatively a kit may be "partial", omitting certain reagents needed for those operations. Both complete and partial kits of this invention may additionally include reagents for sample preparation, such as nucleic acid isolation and reverse transcription. Sequencing may involve two kits, for example, a complete LATE-PCR amplification kit and a complete cycle sequencing kit, or the two may be combined into a single kit.

As used herein an "oligonucleotide set" means a collection of primers or primers and probes for performing an amplification or assay. For sequencing an oligonucleotide set may include, for example, Limiting Primer and Excess Primer for a LATE-PCR amplification and one or more additional sequencing primers for cycle sequencing. For a hybridization probe assay an oligonucleotide set may include, for example, Limiting Primer and Excess Primer for a LATE-PCR amplification and at least one fluorophore-labeled hybridization probe.

As used herein a "single-tube" method means a series of at least two operations, for example, sample preparation, amplification or sequencing, that can be performed without transferring the sample from one container, be it a test tube, a reaction well, a chamber in a microfluidics device, a glass slide, or any other apparatus capable of holding a reaction mixture, to another container.

Probes that have low melting temperatures (that is, probes that form probe-target hybrids having low melting temperatures) can be added to amplification reaction mixtures prior to the start of amplification and utilized only when desired. By keeping temperatures above the melting temperature of a probe during all or portions of an amplification reaction, the probe is kept from hybridizing to its target and possibly reducing the efficiency of the reaction. Certain embodiments of LATE-PCR assays utilize low temperature probes. As used herein, "Low-$T_m$ probe" means a hybridization probe that has a concentration-adjusted melting temperature at the start of amplification, $T_{m[0]}$, at least 5° C. below the $T_{m[0]}$ of the Limiting Primer in a LATE-PCR assay; and a "Super-Low-$T_m$ probe" means a hybridization probe that has a $T_{m[0]}$ that is at least 5° C. below the mean primer annealing temperature of the exponential phase of a LATE-PCR reaction. We frequently add probes to LATE-PCR reactions at 1 micromolar (µM) concentration. Therefore, when designing probes, we sometimes utilize a nominal $T_{m[0]}$ calculated as described earlier but utilizing a nominal concentration of 1 µM. Most Low-$T_m$ and Super-Low-$T_m$ probes have a $T_{m[0]}$ calculated at 1 TM concentration in the range of 30-55° C.

Detection utilizing low temperature probes requires low temperature detection, wherein the temperature of the probe-target mixture is lowered sufficiently for fluorescently labeled probes to hybridize and signal. This can be done at the conclusion of amplification (end point) or in a post-amplification melting analysis. Alternatively a low-temperature detection step may be included in some or all cycles of the linear phase of a LATE-PCR amplification for a real-time assay. Preferably such a step occurs after primer extension and before high-temperature strand melting (or "denaturation"), although it could be included in the primer annealing step. A low-temperature detection step in a LATE-PCR assay signifies a reduction in temperature at least 5° C. below the primer annealing temperature.

Certain methods according to this invention utilize fluorophore-labeled primers or hybridization probes in combination with fluorescent dyes that bind to double-stranded DNA and include stimulating a dye at a wavelength that excites the dye but not the fluorophore(s) and detecting fluorescence emitted by a fluorophore stimulated indirectly by this procedure. Some embodiments of methods according to this invention include detecting fluorescence emission from the dye as well. Certain preferred methods further include calculating the ratio of fluorophore emission to dye emission.

One embodiment of this invention includes adding to a nucleic acid amplification mixture a fluorescent DNA dye, such as SYBR Green I, or preferably SYBR Gold, and at least one amplification primer according to this invention, that is, a linear single-stranded oligonucleotide that is extendable by a DNA polymerase and that is labeled with a fluorophore that is indirectly excitable to signal priming as described above; performing an amplification reaction, preferably a PCR reaction (including LATE-PCR), that includes annealing and extending that labeled primer; and either during the amplification (real-time detection) or following completion of amplification (either an end-point detection at the conclusion of the amplification reaction or during a subsequent thermal analysis (melting curve)) exciting the dye and detecting fluorescence emission from the fluorophore, either alone or in combination with detecting fluorescence emission from the dye. By appropriate amplification protocol design, melting analysis of double-stranded products can be included at desired points in an amplification reaction. In this embodiment only primers that are incorporated into double-stranded DNA will fluoresce. Unincorporated primers will not fluoresce, so there is no need to separate unbound primers physically. The method is homogeneous. Also, fluorophore emission comes only from double-stranded regions of products that include a labeled primer, not from all double-stranded products. Example 1 below demonstrates these improvements. It shows that in a single-extension cycle designed to produce mixed extension products of various lengths, a melting curve based on detection of emissions from the primer's fluorophore showed all products, whereas a melting curve based on detection of emissions from the dye did not. Example 1 demonstrates also the use of the method of this embodiment in isothermal reactions.

As will be appreciated by a person versed in the art, it is generally important to correct for fluorescence overlap when a fluorescent DNA dye, for example SYBR Green I, is used in conjunction with a fluorescently labeled primer or probe that is excited by FRET from the intercalated dye. This is the case because fluorescent DNA dyes typically emit light over a broad spectral range which may include the wavelength of light used to measure the fluorescence emitted by the primer or probe. The desired correction can be achieved by: 1) establishing the emission spectrum of the dye alone; 2) measuring the intensity of the dye emission in each sample at a wavelength that is shorter than the emission wavelength of the primer or probe; 3) calculating the intensity of the dye emission at the emission wavelength of the primer or probe on the knowledge of steps 1 and 2; and 4) subtracting that calculated dye intensity from the total intensity measured at the emission wavelength of the primer or probe. Many commercially machines, such as the ABI 7700 and the Cepheid Smart Cycler provide software for carrying out this correction. Alternatively the measurements of dye spectrum, dye emission alone, and total dye/probe emission can be made and a satisfactory formula for correction can be manually applied. For instance, Lee and Fuerst, United States Published Patent Application Pub. No. US 2002/0119450 describes such a formula for measurement and manual correction of SYBR Green I fluorescence overlap on the Light Cycler.

All of the Examples described in this application were carried out on the ABI 7700 and machine software was used to correct for fluorescence overlap in all cases in which a fluorescent DNA dye was used in conjunction with an indirectly excited fluorescent primer or probe, regardless of whether the fluorescence of the dye alone was recorded.

For PCR amplifications utilizing a single primer pair, wherein at least one primer is fluorophore-labeled for indirect excitation as described above, a melt-curve analysis according to this embodiment can distinguish between the intended product(s) and non-specific products. For multiplex PCR amplifications utilizing multiple primer pairs, wherein at least one member of each pair is fluorophore-labeled and a different fluorophore is utilized for each pair, different intended products can be distinguished by color and by the melting temperatures associated with the different fluorophores. For PCR amplifications generally, fluorophore emission(s) and dye emissions can be monitored during the reaction to track the build-up of specific products(s) and to track the build-up of all double-stranded products, respectively.

Analyses of amplification reactions may utilize the ratio of fluorophore emissions, a signal specific to hybridized primers or probes, to the dye-emission signal, which is not so specific. Such a ratio, for example, corrects for variations among replicate reactions. Also, analyses may utilize the primer-template melting peak, which decreases in magnitude as labeled primer is incorporated into extension product or products.

This invention includes amplification kits and partial kits that include a fluorescent DNA dye, at least one primer pair that includes a primer labeled with a fluorophore that is excited indirectly when the dye is excited, and reagents to amplify the region defined by the primers, preferably by LATE-PCR.

Another embodiment of a method according to this invention includes adding to a nucleic acid amplification mixture a fluorescent DNA dye, such as SYBR Green I or, preferably, SYBR Gold, and at least one indirectly excitable, quenched, allele-discriminating Low-$T_m$ or Super-Low-$T_m$ hybridization probe, which may be a probe of this invention. Allele-discriminating probes of this invention are the type of double-stranded probes described by Li, Q. et al. (2002), "A New Class of Homogeneous Nucleic Acid Probes Based on Specific Displacement Hybridization," Nucl. Acid Res. 30: (2)e5 (a fluorophore-labeled linear oligonucleotide probe strand complementary to the target, and a quencher-labeled complementary strand that is shorter than the probe strand, generally by 2-10 nucleotides), except that they are labeled with a fluorophore that is excited indirectly by exciting the dye, and that they have a low melting temperature suitable for use in LATE-PCR amplifications as Low-$T_m$ or Super-Low-$T_m$ probes. Allele-discriminating capacity of double-stranded probes can be adjusted as has been described by Li et al., as can the level of background fluorescence. In addition, background fluorescence can be reduced by including guanidine residues adjacent to the fluorescent moiety, so-called "G-quenching."

Methods of this embodiment include amplification utilizing such a mixture and detection at a temperature at which the probe hybridizes in an allele-discriminating fashion. Preferred embodiments include using a low-temperature detection step during the linear amplification phase of a LATE-PCR reaction wherein the foregoing probes hybridize to the single-stranded amplicon being synthesized, exciting the fluorescent DNA dye at a wavelength that does not excite the fluorophore or fluorophores directly, and reading fluorescence from the probe's fluorophore or probes' fluorophores, which is or are excited indirectly in this fashion. Other embodiments include amplification followed by a low-temperature detection as an end-point determination. Some embodiments further include detecting emission from the dye, and certain preferred embodiments include calculating a ratio of probe(s) emission to dye emission. Detection of dye emission is most preferably performed at the very start of the detection step, while the temperature of the reaction mixture is above the melting temperatures of all probes that are present. Data from accumulating or accumulated double-stranded molecules (the dye signal) and from accumulating or accumulated single-stranded molecules (the signal from each probe) can be used to construct ratios in the manner described. Methods of this embodiment also include use of low-temperature molecular beacon probes, as described in published application WO 03/054233, if the fluorophore label is stimulated by emission from the dye but not by the wavelength used to excite the dye.

This invention also includes LATE-PCR assay kits and partial kits that include reagents for performing a non-symmetric amplification, preferably a LATE-PCR amplification, with a low temperature detection step (end point or real time) and that include a fluorescent DNA dye, at least one primer pair, preferably a LATE-PCR primer pair including an Excess Primer and Limiting Primer, and at least one fluorophore-labeled Low-$T_m$ or Super-Low-$T_m$ hybridization probe for a single-stranded product of the amplification reaction (extension product of the primer present in excess), wherein the probe is not mismatch tolerant but rather is allele-discriminating at the intended detection temperature, and wherein the probe's fluorophore is indirectly excited by excitation of the dye. In preferred kits and partial kits, at least one probe is an allele-discriminating probe of this invention. This invention also includes oligonucleotide sets that include at least one pair of primers for non-symmetric amplification, preferably LATE-PCR amplification, and at least one Low-$T_m$ or Super-Low-$T_m$ quenched allele-discriminating double-stranded probe labeled with a fluorophore so as to be indirectly excitable as described above, preferably by a SYBR dye, as well as such double-stranded probes themselves.

Yet another embodiment of a method according to this invention includes adding to a non-symmetric amplification reaction mixture, preferably a LATE-PCR reaction mixture, detection reagents comprising a fluorescent DNA dye such as SYBR Gold and at least one mismatch-tolerant single-stranded linear hybridization probe that is perfectly complementary to one possible single-stranded amplicon target sequence that may or may not be present for amplification in the reaction and is less than perfectly complementary to at least one other possible single-stranded amplicon target sequence that may be present. Probes useful in this embodiment are single strands labeled with a fluorophore that is indirectly excitable by fluorescence emission from the dye. They are Low-$T_m$ or, preferably, Super-Low-$T_m$ probes with respect to their most complementary possible targets that may be present, generally meaning perfectly matched target. It is preferred that they have a $T_{m[0]}$ against perfectly complementary target that is not more than a few degrees higher, and preferably below, more preferably at least 5° C. below, the primer annealing temperature during the exponential amplification phase of the amplification reaction. The probes may be linear (or random-coil) probes, or random-coil probes according to this invention, that is, quenched to eliminate signal due to formation of secondary structure at low temperatures. Quenched linear probes according to this invention preferably have a fluorophore on one end and a non-fluorescent quenching moiety on the other end, the one on the 3' end of the probe replacing the phosphate cap otherwise added to prevent the probe from being extended, that is, functioning as a primer.

This embodiment comprises subjecting the foregoing mixture to non-symmetric, preferably LATE-PCR, amplification to generate single-stranded amplicon molecules and subjecting the amplification reaction mixture to a thermal analysis utilizing at least one mismatch tolerant probe that signals upon hybridization. Thermal analysis can be performed not only after the amplification reaction is completed but also during a LATE-PCR low-temperature detection step during thermal cycles in which single-stranded product is being produced, that is, after exhaustion of the Limiting Primer. Thermal analysis reveals targets of each probe according to the melting temperatures of the probe-target hybrids that form or destabilize as the temperature is lowered or raised, respectively. As the temperature is lowered, a probe will first hybridize to its perfectly matched target (if present) and emit a fluorescent signal. As the temperature is lowered further, the probe will hybridize successively to progressively "more mismatched" targets and emit increased fluorescent signal on each occasion. As explained in connection with previous embodiments, emission from the fluorescent DNA dye can also be detected, preferably when probes are not hybridized, that is, at a temperature above the $T_m$ of the probe(s), to permit monitoring of the accumulation of double-stranded molecules in the reaction and to permit the use of ratios to reduce scatter among replicate samples.

This invention includes kits containing reagents for non-symmetric amplification, preferably a LATE-PCR amplification, that include a fluorescent DNA dye, at least one primer pair, preferably a LATE-PCR primer pair including an Excess Primer and a Limiting Primer, and at least one mismatch-tolerant Low-$T_m$ or Super-Low-$T_m$ random coil probe, quenched if necessary, for a single-stranded amplification product(s), as well as partial kits and oligonucleotide sets containing such primers and probes, and such probes themselves.

Methods according to this invention that utilize a low-temperature detection step of LATE-PCR assays, preferably a low-temperature detection step following primer extension and before strand melting, include multiplex probe assays which contain more than one pair of primers and generate one or more single-stranded amplicons (one probe for each target) as well as multiprobe assays that contain at least one probe for multiple targets. Certain preferred methods with a low-temperature detection step include a low-temperature detection step following primer extension and before strand melting. During the detection step in such assays the temperature may be dropped as much as 30° C. or even 40° C. below the primer annealing temperature, providing a large temperature window for detection. Allele-discriminating probes, in addition to being differentiable by color (fluorophore emission wavelength) can be differentiated by differences in melting temperature. For example, four different FAM-labeled allele-discriminating probes with $T_m$'s of 30, 35, 40 and 45° C., respectively, against their targets can be distinguished in real time or following amplification as an end-point determination, as the reaction temperature is lowered or raised, not just by post-amplification melt analysis. This added degree of freedom multiplies significantly the number of different probes that can be used in the same reaction. Mismatch-tolerant probes will have lower $T_m$'s against mismatched targets than against perfectly matched targets. Combinations of differently colored low-temperature mismatch-tolerant probes that signal upon hybridization produce patterns of temperature-dependent fluorescence emission curves during low-temperature detection. Methods according to this invention include use of such emission curves, derivative curves, and ratios of either of them at one temperature or different temperatures to identify the constituents of mixed targets with post amplification melt analysis and also in real time by monitoring fluorescence at several temperatures within the window of LATE-PCR low-temperature detection step. Ratios may include same probe/probe, different probe/probe ratios, probe/dye ratios, and combinations thereof.

LATE-PCR kits, partial kits and oligonucleotide sets may include at least two allele-discriminating probes of the same color that can be distinguished by $T_m$ or at least two mismatch-tolerant probes whose hybridization to different targets can be distinguished by $T_m$, preferably quenched random-coil probes that are indirectly excited by exciting a fluorescent DNA dye.

This invention includes improved methods for preparing the amplification products of LATE-PCR amplifications for sequencing reactions, either dideoxy sequencing or sequencing-by-synthesis methods such as pyrosequencing. In particular, we have demonstrated the generation and preparation of such starting materials in a single reaction container, for example, a microcentrifuge tube. Preferred embodiments include in the LATE-PCR reaction mixture a reagent for inhibiting mispriming, most preferably a reagent disclosed in our U.S. Provisional patent application No. 60/619,620, titled "Reagents and Methods for Improving Reproducibility and Reducing Mispriming in PCR Amplification," which is incorporated by reference herein in its entirety. For dideoxy sequencing we have demonstrated preparing LATE-PCR amplification products for sequencing by the single step of sample dilution, a method we refer to as "dilute and go." For pyrosequencing, we have demonstrated methods that require only addition of pyrosequencing enzyme/substrate reagents to the LATE-PCR product mixture prior to primer annealing. In some embodiments, the amplification product of a LATE PCR process is cleaned up by diluting the amplification product by a factor of at least five (e.g., at least 8-fold).

Methods according to this invention also include LATE-PCR amplification and sample preparation for Pyrosequencing in the same container, such as the same reaction tube or the same chamber of a microfluidics device, all of which we refer to for short as "single-tube" methods. In traditional Pyrosequencing, DNA is amplified by symmetric PCR where one primer is 5' labeled with a biotin molecule. After amplification, streptavidin coated beads are used in conjunction with vacuum or magnetic equipment to isolate single-stranded DNA (ssDNA) and wash away residual components of the PCR reaction that interfere with Pyrosequencing including pyrophosphate (PPi), dNTPs and PCR primers. By virtue of its ability to generate ssDNA, LATE-PCR eliminates the need for strand separation and simplifies sample preparation when combined with a same-container method for eliminating the four interfering components left over from PCR. In one such method, the need to remove dNTPs remaining at the end of amplification is minimized by using limiting amounts of dNTPs in the LATE-PCR amplification reaction mixture, care being taken to utilize a sufficient amount to produce enough ssDNA for Pyrosequencing. An enzyme with pyrophosphatase activity, for example a pyrophosphatase such as yeast pyrophosphatase, is added to the amplification product to remove PPi and the mixture is heated to denature that enzyme before proceeding to Pyrosequencing. Because Limiting Primer does not remain after LATE-PCR amplification and the residual Excess Primer cannot prime the strand extended from the Excess Primer during amplification (Excess Primer strand), leftover primers need not be removed in many cases. However, potential mispriming can be avoided by including in the LATE-PCR reaction mixture an oligonucleotide that hybridizes to the Excess Primer at temperatures below the $T_m$ of the Excess Primer, including the temperature used for Pyrosequencing. Alternatively, an oligonucleotide blocked for extension at the 3' end and fully complementary to the Excess Primer can be added after LATE-PCR amplification but before Pyrosequencing to avoid potential mispriming by the Excess Primer at temperatures used for Pyrosequencing. A third strategy to avoid mispriming by the Excess Primer at the 3' end of the strand extended from the Limiting Primer during amplification (Limiting Primer strand) involves using a sufficient concentration of a 3' blocked oligonucleotide containing the same sequence as the Excess Primer to out-compete the Excess Primer for binding sites.

Our more preferred method of "single-tube" sample preparation avoids the need to determine appropriate limiting dNTP concentrations for particular amplifications. In this method we first add Pyrosequencing enzyme/substrate reagents to the LATE-PCR product, which removes dNTPs and PPi. We follow this with primer annealing using an added sequencing primer and then add individual dNTPs for Pyrosequencing. Alternatively, one may eliminate dNTPs by addition of a purified enzyme with a dNTPase activity, such as potato apyrase, followed by heating to inactivate the enzyme and one may eliminate pyrophosphate by addition of a purified enzyme with pyrophosphatase activity, such as yeast pyrophosphatase, followed by heating to inactivate the enzyme. If both enzymes are employed they can be added at the same time.

Assays according to this invention particularly LATE-PCR assays, preferably include means to avoid mispriming, which can cause a decrease in probe signal in the late stages of the reaction. We have successfully avoided this "hook effect" by including in the reaction mixture a mispriming-suppressing reagent disclosed in our United States Provisional patent application described above. We have also avoided that effect by adjusting the concentration of polymerase added to the reaction. Decreasing mispriming by adjusting polymerase can be observed in terms of the kinetics of the LATE-PCR reaction using a probe of the ssDNA, as well as by the composition of the final product revealed by various means known in the art.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
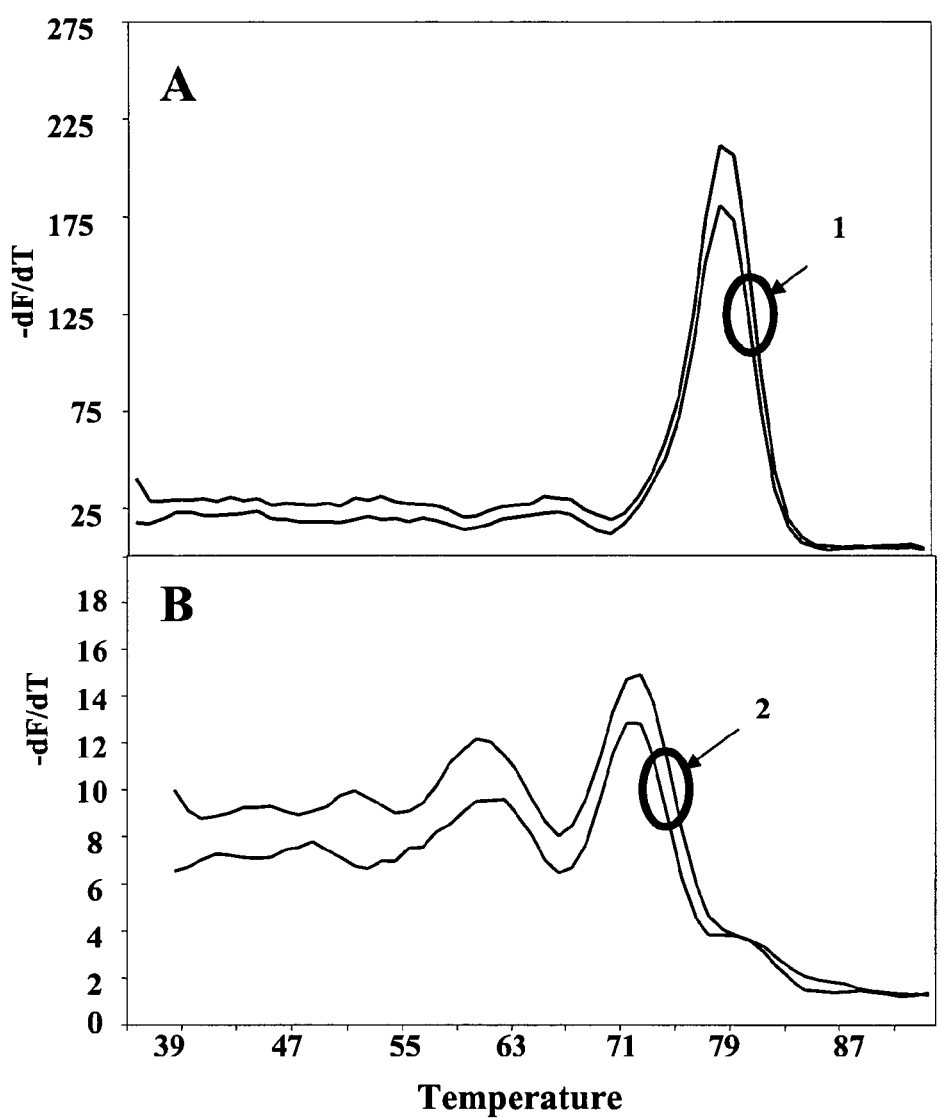
FIGS. 1A and 1B show the use of fluorescently labeled primers according to the methods of the invention for melting curve analysis.

This invention includes nucleic acid amplification assays, for example PCR assays, that include detection of fluorescence emission from at least one fluorophore-labeled primer that is excited, not directly by applying light (visible or not) of a wavelength strongly absorbed by the fluorophore, but indirectly by applying light of a wavelength that excites a nearby fluorescent DNA dye such as SYBR Green or, preferably, SYBR Gold, as well as complete and partial kits containing all or some amplification reagents and oligonucleotide sets containing such labeled primers, and also the primers themselves.

Amplification primers are well known. Primers according to this invention are short oligonucleotides, generally under fifty bases in length that hybridize to a target strand and are extended by an appropriate polymerase. A primer may be composed of naturally occurring nucleotides, or it may include non-natural nucleotides and non-natural internucleotide linkages. Although primers are generally linear oligonucleotides, they may include secondary structure. (See, for example, Nazarenko I A, Bhatnagar S K, Hohman R J (1997), "A Closed Tube Format for Amplification and Detection of DNA Based on Energy Transfer," Nucleic Acids Res. 25:2516-2521). Amplifications often include use of one or more primer pairs each consisting of a forward primer and a reverse primer. In methods, kits and oligonucleotide sets according to this invention, either one primer of a pair or both primers of the pair may be labeled with a covalently bound fluorophore that fluoresces when nearby fluorescent DNA dye is stimulated. When the labeled primer hybridizes (or anneals) to its complementary sequence in a template strand, a double-stranded region is formed. Fluorescent DNA dye associates with that region, by intercalating therein or otherwise, and becomes fluorescent in that region, which is nearby to the primer's fluorophore such that when the dye is stimulated at a wavelength that does not directly excite the fluorophore, the fluorophore emits at its characteristic wavelength. These primers may be used to monitor synthesis of products resulting by extension of a DNA polymerase such as those resulting from PCR and primer extension assays in real-time or by end-point detection and/or to assess product specificity by melting curve analysis.

Primers according to this invention, used as a substrate for extension by a DNA polymerase, including primers for PCR amplification (symmetric or non-symmetric, including particularly LATE-PCR), are labeled at any nucleotide position with a covalently bound fluorophore such that the 3' end of the oligonucleotide primer remains available for extension. The primers can have the design of double-stranded probes described by Li, Q. et al. (2002) ("A New Class of Homogeneous Nucleic Acid Probes Based on Specific Displacement Hybridization," Nucl. Acid Res. 30: (2)e5). The only sequence constraint on the oligonucleotide of the primer is that the oligonucleotide must not have any secondary structure that itself leads to indirect fluorophore excitation, meaning that generally there is not secondary structure greater than 2 base pairs. The fluorophore moiety should not be appreciably excited directly by, but the dye must be directly excited by, the excitation source wavelength used; the fluorophore must emit when the fluorescent DNA dye is excited in its immediate presence, generally not greater than a distance at which the fluorophore undergoes fluorescence resonance energy transfer (FRET) occurs; and the emission spectrum of the chosen fluorophore must be distinguishable from the emission spectrum of the fluorescent DNA dye either by the use of filters or spectral deconvolution. Under these conditions, the fluorophore fluoresces upon incorporation into double stranded product following primer annealing, including extension by a DNA polymerase. Loss of fluorescence takes place during heating when at the melting temperature ($T_m$) of the particular stretch of double-stranded DNA containing the fluorophore is reached.

Conditions for the use of primers according to this invention in conjunction with fluorescent DNA dyes (primer and DNA dye concentration, DNA dye excitation wavelength) are the same as those known in the art for monitoring the synthesis of products of primer extension reactions (including PCR) in the course of the reaction and for assessing extension product specificity by melting curve analysis using only fluorescent DNA dyes with the exception that fluorescence is collected at the emission wavelength corresponding to the primer fluorophore instead of or in addition to the emission wavelength of the dye. Under these conditions, the fluorescence signals originate from double-stranded sequences containing the primers, rather than all double-stranded sequences in the reaction.

Comparison of the performance of DNA dye to methods and systems according to this invention was performed by the experiment reported below in Example 1 and in FIG. 1. A fluorophore-labeled primer was extended by DNA polymerase in the presence of SYBR Green dye and in the presence of a relatively long non-extendable oligonucleotide hybridized to the template strand near to the region of primer extension. This resulted in a product mixture having template strand-unextended primer hybrids, short primer-extension products, and the non-extendable oligonucleotide, such that hybrids with the template had $T_m$'s ranging from 60° C. (the fluorophore (Cy5)-labeled primer) to 79° C. (the non-extendable oligonucleotide), with primer-extension products falling between those two $T_m$'s.

Standard melt-curve analysis was performed on the final reaction mixture (duplicate samples) using both fluorescence readings from the dye and fluorescence readings from the fluorophore. Melting curves are presented in FIG. 1. Panel A is the melt curves 1 obtained utilizing dye emissions. The sole peak is 79° C., the melting temperature of the nonextendable oligonucleotide. No other peak is seen, not even that of the unextended primer. Panel A demonstrates the migration of SYBR Green dye to the higher $T_m$ hybrid during generation of a melt curve, which masks the presence of lower $T_m$ hybrids. Panel B is the melt curves 2 obtained utilizing fluorophore emissions. It shows a peak at 60° C., the $T_m$ of unextended primer-template hybrid, and an additional peak at a temperature between 69° C. and 79° C., that is, a peak indicative of primer extension product. The lower $T_m$'s are seen despite the tendency of the dye to migrate, as shown by melt curves 1. Monitoring fluorophore emission according to this invention reveals every hybrid species labeled with the fluorophore in the mixture at its correct concentration.

In the case of PCR amplifications utilizing a single pair of primers, wherein at least one member of the pair is a primer according to this invention, melt curve analysis can distinguish between specific and non-specific products using a single fluor because the specific product has an expected melting temperature and the non-specific product has an unexpected, melting temperature. In the case of multiplex PCR amplifications, utilizing more than one pair of primers, wherein at least one member of each pair of primers is a primer according to this invention, two different specific products can be distinguished from each other either because they have different, but expected, $T_m$ values and or because the two different primers employed are labeled with different fluorophores. Moreover, melting curve analysis using primers according to this invention can be carried out during an ongoing amplification reaction or at the end of a reaction.

Incorporation of one or more primers according to this invention during the course of a reaction can also be used to measure quantitatively the extent of amplification of one or more targets during the course of a PCR, or the synthesis of one or more stretches of double-stranded DNA during the course of an isothermal extension reaction. In either case, the amount of the full-length double-stranded product molecule or molecules can be followed over time by repeated detection of increasing fluorescence, or can be measured at the end of a reaction. In addition, incorporation of one or more primers according to this invention during the course of either isothermal reactions or thermal cycled reactions can be used to measure existence and/or accumulation of partial products, i.e. those that have begun extension along a template strand but have not reached their maximum possible length. In such cases the melting temperatures of the partial products are lower than the melting temperature of the full-length product, but are higher than the melting temperature of the labeled primer from which they are derived. In addition, concomitant with incorporation of the labeled primer into a partial or full-length product strand, the magnitude of the melting temperature peak generated from the primer/template DNA-DNA hybrid decreases, and can be used as an additional measure of DNA synthesis.

As stated above, each stretch of double-stranded DNA or amplicon synthesized by incorporation of a primer according to this invention generates a fluorescent signal at the emission wavelength of the covalently bound fluorophore of the primer, when indirectly stimulated by FRET or other mechanism from the bound SYBR dye, a "primer-specific-signal". The same double-stranded DNA also generates a fluorescent signal at the emission wavelength of the SYBR dye, the "total-SYBR-signal", the sum of all double-stranded sequences present in the reaction, since all double-stranded sequences fluoresce, regardless of whether they have an incorporated labeled primer. Thus, primers according to this invention can be used to analyze the fluorescent signals in terms of the following ratio: (primer-specific-signal/total-SYBR-signal), hereafter the (PSS/TSS) value. Data analysis in terms of the (PSS/TSS) value corrects for variations in fluorescent DNA dye signal (TSS) among replicate reactions. This is particularly useful in the case of LATE-PCR amplifications because the rate of single-stranded amplicon synthesis is proportional to the amount of double-stranded amplicon accumulated at the end of the exponential phase of the reaction. Thus, small differences in the level of double-stranded DNA among replicate reactions alter the rate of single-stranded amplicon accumulation.

It is also possible to utilize more than one primer labeled with the same fluorophore, as long as the amplicons are differentiable by a post-amplification melting-curve analysis. See FIG. 1, Panel B, for exemplification of this principle. Signal from the common fluorophore at the end of an extension step, which may be the final extension step (end point) or intermediate extension steps, gives an indication of total amplicons incorporating the fluorophore. Melt-curve analysis distinguishes among products and provides a quantitative measure of their concentrations.

LATE-PCR is a non-symmetric PCR amplification that, among other advantages, provides a large "temperature space" in which actions may be taken. See WO 03/054233 and Sanchez et al. (2004), cited above. LATE-PCR permits the use of "Low-$T_m$" and "Super-Low $T_m$" hybridization probes to detect amplification products ("amplicons") that are single-stranded. Various types of probes that are single-target-specific in a particular assay, including allele-discriminating probes capable of discriminating against a single base-pair mismatch, such as allele-discriminating molecular beacon probes, can be utilized with LATE-PCR as Low-$T_m$ and Super-Low $T_m$ probes, as can mismatch-tolerant probes such as mismatch-tolerant molecular beacon probes or linear (random-coil) probes having a fluorophore excitable indirectly by emission from a SYBR dye. We have devised a new class of allele-discriminating probes useful as Low-$T_m$ and Super-Low $T_m$ probes in LATE-PCR assays that permit the determination of single-stranded/double-stranded ratios within a reaction, as can allele-discriminating molecular beacon probes labeled with such a fluorophore.

Allele-discriminating probes according to this invention are modified double-stranded, allele-discriminating, quenched probes according to Li, Q. et al. (2002), Nucl. Acid Res. 30: (2)e5. They have the following modifications: they are labeled with a fluorophore that is indirectly excitable by exciting a double-stranded DNA fluorescent dye such as SYBR Green or SBYR Gold but not directly excitable by wavelength utilized to stimulate the dye (in this regard similar to the primers discussed above), and they are constructed to be Low-$T_m$ or Super-Low $T_m$ probes. When not bound to its target sequence, such a probe binds to a shorter complementary oligonucleotide. We prefer that the complementary oligonucleotide include a quencher such as Dabcyl or a Black Hole™ quencher to reduce background fluorescence from the probe. Alternatively or in addition, background fluorescence can be reduced by including guanidine residues adjacent to the fluorophore (G-quenching). In the presence of fully complementary target strand, the shorter complementary strand is displaced, the longer fluorophore-labeled strand hybridizes to the target, and the fluorophore is unquenched and rendered capable of receiving energy from the dye so as to fluoresce at its characteristic wavelength. Several of these probes for different targets, labeled with different fluorophores, can be used for multiplex assays.

Such allele-discriminating probes are designed to have a concentration-adjusted melting temperature, $T_{m[O]}$, in the assay that makes it a Low-$T_m$ or Super-Low $T_m$. The $T_{m[O]}$ of the probe-target hybrid is conveniently determined and adjusted empirically, although a calculated value may be employed at least as a good starting point to minimize adjustment. The length and concentration of the complementary probe strand relative to the fluorophore-labeled strand are adjusted empirically for maximal allele discrimination. We start with a length 1-3 nucleotides shorter than the fluorophore-labeled strand and a concentration of 1-1.2 times the concentration of the fluorophore-labeled strand.

In a LATE-PCR assay, these allele-discriminating probes are utilized in a low-temperature detection step, preferably following the primer extension step in cycles following exhaustion of the Limiting Primer. For real-time readings over multiple cycles, the SYBR dye is excited and fluorescence is read both from both the dye and from the fluorophore (or fluorophores). We prefer to read the dye signal during or at the conclusion of the PCR extension step when the temperature is above the $T_m$ of the probe (or probes), and to read the fluorophore emission during the low detection-step temperature when the probes (either an allele-discriminating probe according to this invention or an appropriately labeled molecular beacon probe) are hybridized. We then determine the ratio of fluorescence of each probe to total-SYBR-signal. This ratio minimizes differences among replicate assays due to differences in product accumulation. Because differences are minimized, such ratios can be used for end-point analysis as well.

Figure 2:
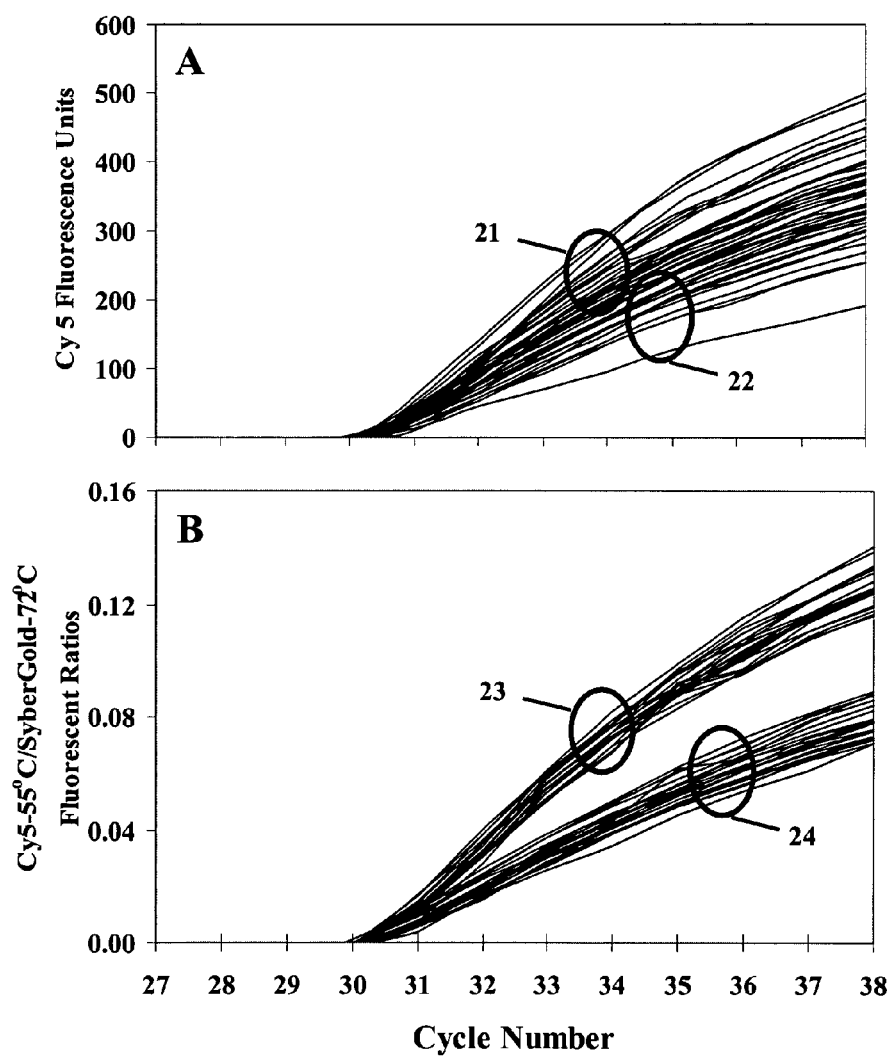
FIGS. 2A and 2B show reduction of signal scatter through the use of ratios of single-stranded product to double-stranded product according to the methods of the invention.

The use of ratios of single-stranded product to double-stranded product permitted by primers and probes according to this invention is a technique for reducing scatter among replicate assays, as has been stated. This is particularly important for end-point assays, which do not reveal reaction kinetics. An example is a LATE-PCR assay to distinguish homozygous samples from heterozygous samples utilizing one primer pair for both alleles and an allele-discriminating probe according to this invention. FIG. 2 illustrates the reduction in scatter achieved when applied to a LATE-PCR amplification with a low-temperature detection step performed with a SYBR dye (in this case SYBR Gold), an allele-discriminating probe for one allele labeled with Cy5, excitation of the dye and readings of signals from the dye (at 72° C., the extension temperature) and the fluorophore (at 55° C., a low-temperature detection following primer extension). Panel A presents the real-time readings from the fluorophore for replicate homozygous samples (circle 21) and replicate heterozygous samples (circle 22). As is apparent, scatter among replicates blurs the difference. Panel B, however, plots the ratio of Cy5 signals to SYBR signals for the homozygous samples (circle 23) and heterozygous samples (circle 24). The scatter reduction is sufficient to permit an end-point assay.

This invention also includes mismatch tolerant Low-$T_m$ or Super-Low-$T_m$ linear single-stranded probes that are labeled, preferably terminally labeled, with a fluorophore excitable by emission from a fluorescent DNA dye (for example, SYBR Green I or SYBR Gold) and that are quenched to reduce background fluorescence. These probes carry a quenching moiety that suppresses fluorescence in the absence of target. Mismatch-tolerant linear probes have a tendency to fold and form short double-stranded regions as the temperature is lowered. Use of a low-temperature LATE-PCR detection step exacerbates this tendency. This does not occur when the probe sequence is hybridized to the target sequence. If the probe includes a fluorophore that is excited by emission from a SBYR dye that is present in the reaction mixture, the dye intercalates into or otherwise associates with the unintended double-stranded region of the unbound probe molecules and thus excites the fluorophore of the probe by FRET. The result is an increase in background fluorescence at low temperature.

Quenching of mismatch-tolerant probes according to this invention is obtained by addition of a quenching moiety, for example, a DABCYL or a Black Hole™ quencher (BHQ), to the probe at a location at which it quenches fluorophore fluorescence resulting from unintended secondary structure within the unbound probe. We prefer to add the quencher at the end opposite to the fluorophore whenever possible. Example 2 below exemplifies two possible techniques, simply adding a quencher or constructing a quenched hairpin, that is, a specifically designed secondary structure that brings the quencher in close proximity to the fluorophore, to the secondary structure, or both. Preferably the $T_m$ of the constructed secondary structure is at least 5° C. higher than the $T_m$ of any alternative secondary structure so that in the absence of target most probe molecules are in the hairpin configuration and background fluorescence is low. The $T_m$ of the constructed stem is below the $T_m$ of the probe hybridized to perfectly matched target and similar to the $T_m$ of the probe hybridized to its mismatched targets, such that hybridization to targets of sequence within the stem is not prevented by formation of the stem.

Detection and identification of nucleic acid targets can be accomplished by utilizing one or multiple low-temperature mismatch tolerant probes that signal when hybridized, including mismatch-tolerant molecular beacon probes, linear single-stranded probes that are indirectly excited by exciting a fluorescent DNA dye, and quenched linear probes according to this invention. A probe mixture may, for certain embodiments, include as well at least one allele-specific probe according to this invention. A useful technique is to utilize the ratio of fluorescence of two probes as a function of temperature to distinguish among targets having a similar with $T_m$ respect to at least one of the probes. We sometimes refer to curves of such a ratio as a "fluorescence signature" of a target.

With LATE-PCR that includes a low-temperature detection step it is possible to combine the effect of detection temperature with the effect of fluorescence signature. An assay we have used with multiple mismatch-tolerant probes, including but not limited to quenched, single-stranded, indirectly excitable probes according to this invention, is a LATE-PCR amplification consisting of a high-temperature step to denature double-stranded DNA (95° C. for 2 min), followed by exponential phase amplification utilizing both Limiting Primer and Excess Primer (30 cycles of 95° C. for 10 sec, 60° C. for 15 sec, and 78° C. for 40 sec), followed by the completion of the exponential phase and the subsequent linear phase during which probe detection steps are included (40 cycles of 95° C. for 10 sec, 60° C. for 15 sec, 78° C. for 40 sec, 55° C. for 20 sec, 50° C. for 20 sec, 45° C. for 20 sec, and 40° C. for 20 sec). This provides four detection temperatures below the primer annealing temperature, 60° C. Double-stranded production can be monitored by emission from SYBR dye at the primer-extension temperature, 78° C., which is above the $T_m$ of any probe. Fluorophore emission can be monitored at each low-temperature from 55° C. to 40° C. Following the last cycle, the temperature can be dropped to a low value, for example 30° C. and slowly increased for melting analysis. In addition to detected fluorescence levels, ratios of fluorophore fluorescence to dye fluorescence and ratios of fluorophore fluorescence can be used to generate amplicon-differentiating information.

Figure 4:
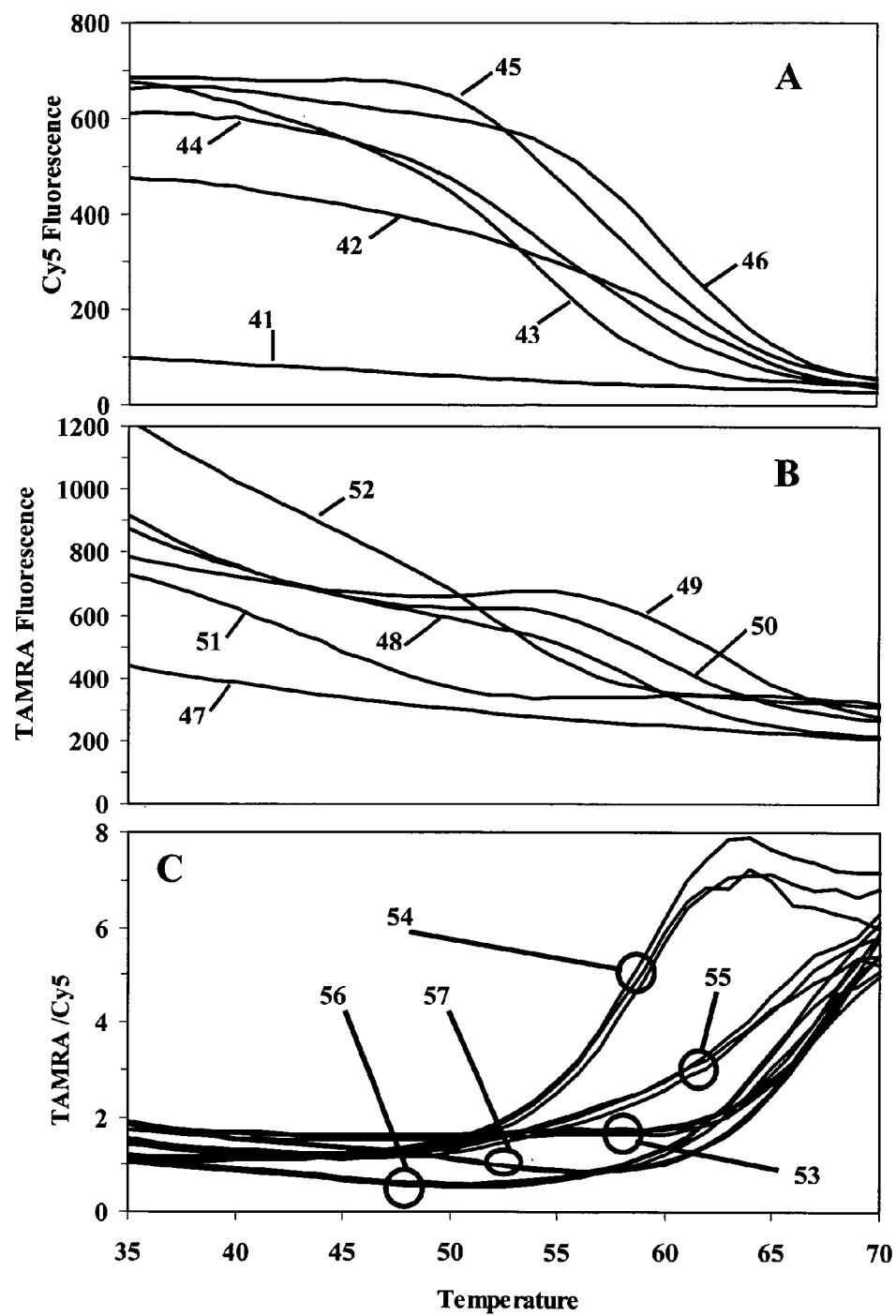
FIGS. 4A, 4B, and 4C show shows identification of five species of Mycobacteria using only two mismatch-tolerant probes against the 16S ribosomal RNA gene according to the methods of the invention.

Certain of the Figures are illustrative of techniques that take advantage of the foregoing possibilities. FIG. 4 shows the melting behavior of two mismatch-tolerant probes against the 16s ribosomal RNA gene of several species of Mycobacteria. Two probes were used: the hairpin-forming, quenched probe described in Example 2, having the sequence 5'-Cy5-CTG GAT AGG ACC ACG AGG CCA G-BHQ II-3' (SEQ. ID No. 2) and a TAMRA-labeled probe having the sequence 5'-G CAT GTC TTG TGG TGG-TAMRA-3' (SEQ. ID No. 3). It was found that the latter probe, which was unquenched, gave discernable signals above background for several species. Panel A of FIG. 4 presents melting curves for the hairpin probe with no target (line 41), M. asiaticum (line 42), M. gordonae (line 43), M. heidelburgense (line 44), M. malmoense (line 45) and M. marinum (line 46). Panel B presents melting curves for the TAMRA-labeled probe with no target (line 47), M. asiaticum (line 48), M. gordonae (line 49), M. heidelburgense (line 50) M. malmoense (line 51), and M. marinum (line 52). Panel C of FIG. 4 plots the ratio of TAMRA fluorescence to Cy 5 fluorescence), M. asiaticum (line 53), M. gordonae (line 54), M. heidelburgense (line 55), M. malmoense (line 56) and M. marinum (line 57).

Figure 5:
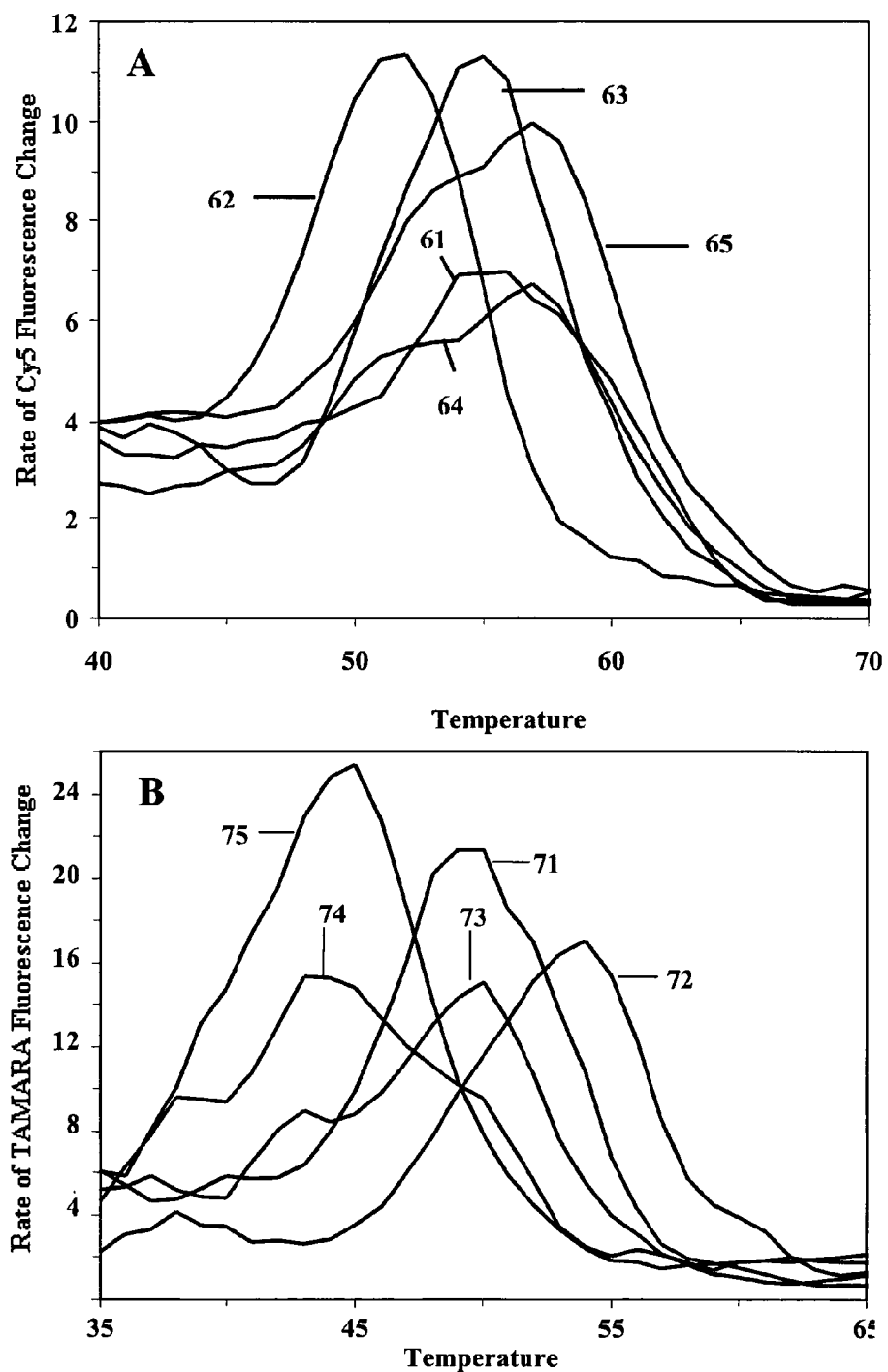
FIGS. 5A and 5B shows identification of five species of Mycobacteria via first derivative analysis of melting curves shown in using two mismatch-tolerant probes against the 16S ribosomal RNA gene designed according to FIGS. 3A and 3B the methods of the invention.

Another analytical technique is to plot the rate of fluorescence change from fluorophores as a function of temperature. FIG. 5 presents such plots for the foregoing Cy5-labeled quenched hairpin probe according to this invention and the TAMRA-labeled unquenched probe, both described above. Panel A is the quenched hairpin probe, and Panel B is the TAMRA-labeled probe. The plots show melting peaks for M. asiaticum (lines 61, 71), M. gordonae (lines 62, 72), M. heidelburgense (lines 63, 73), M. malmoense (lines 64, 74), and M. marinum (lines 65, 75). Using both probes, it is possible to distinguish the five targets by melting peaks. The Cy5-labeled probe by itself was able to distinguish M. gordonae (line 62) from the others. The TAMRA-labeled probe by itself could distinguish each of M. asiaticum (line 71), M. gordonae (line 72) and M. marinum (line 75) from one another. Taken together, the probes could distinguish M. heidelburgense from M. asiaticum, because M. heidelburgense yielded a high peak with the Cy5 probe and a low peak with the TAMRA probe, whereas M. asiaticum yielded the opposite. With a single probe per amplicon, relative peak heights may reflect differences in product concentration. Here, however, both probes detect the same amplicon, so relative peak heights reflect differences in probe-target melting characteristics.

Figure 6:
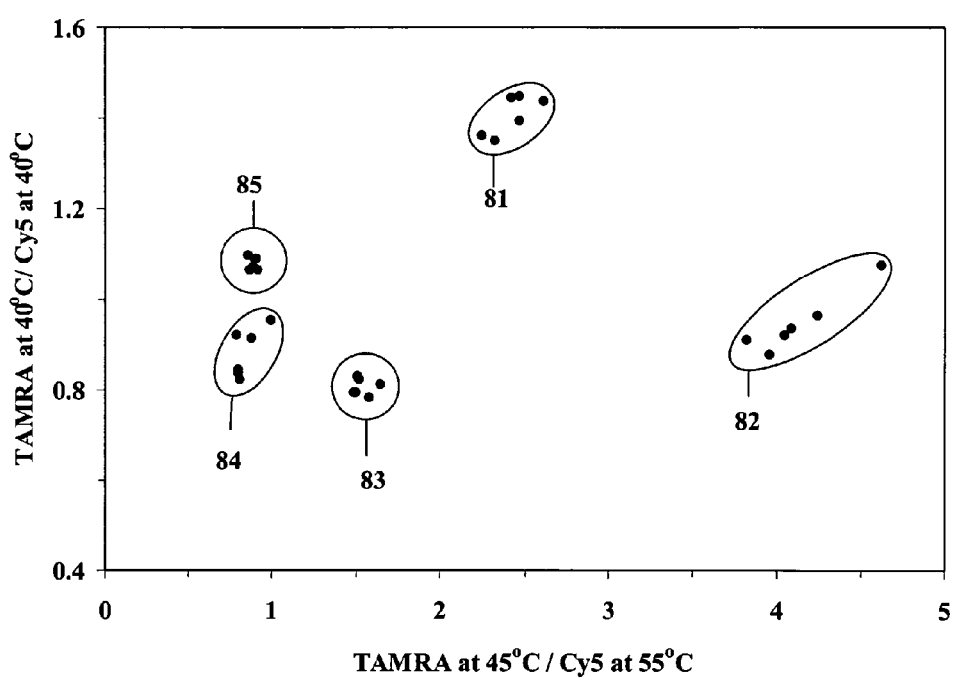
FIG. 6 shows identification of five species of Mycobacteria using ratios of fluorescent signals collected at different temperatures from two mismatch-tolerant probes against the 16S ribosomal RNA gene according to the methods of the invention.

Another analytical tool, described above, is to use one or more fluorescence ratios, such as, in the particular embodiment discussed here, the ratio of TAMRA fluorescence to Cy5 fluorescence at the same temperature or at different temperatures during the PCR. A useful strategy for probe design include designing one probe to bind to a conserved region common to multiple species to serve as a reference, or including, where needed, utilizing a portion of the Limiting Primer sequence as a conserved region. This is an option for LATE-PCR, because probe $T_m$'s are well below the $T_m$ of the Limiting Primer and the annealing temperature, so a probe with a common sequence does not interfere with amplification. FIG. 6 shows the results using a combination of fluorescence ratios. In this embodiment we utilized as one ratio the TAMRA/Cy5 fluorescence values each collected at the 40° C. detection temperature and as the other ratio the ratio of TAMRA/Cy5 fluorescent signals collected at 45° C. and 55° C., respectively, detection temperature. FIG. 6 plots both ratios at a particular cycle, in this instance cycle 50. Six replicates yielded non-overlapping data for the various species M. asiaticum (circle 81), M. gordonae (circle 82), M. heidelburgense (circle 83), M. malmoense (circle 84), and M. marinum (circle 85).

Measuring probe fluorescence at different temperatures during PCR has advantages over limiting the analysis to post-PCR melts. One advantage is the ability to compare fluorescence values at a specific number of cycles after the threshold cycle, $C_T$ value, is reached. This enables the use of ratios with SYBR dyes (or other intercalating dyes) as described above. Another advantage is that each sample has background fluorescence measured at each temperature during cycles prior to amplicon detection. Thus, accurate adjustments can be made for sample-to-sample variations in background fluorescence. It is possible to measure fluorescence at many temperatures during the PCR, providing nearly complete melting analysis over the temperature range at which a probe shows differences in hybridization to different targets. The number and duration of these steps depends in part on the capabilities of the detection equipment. Continuous fluorescence detection during increases or decreases in temperature is possible with some thermal cyclers. Detection at multiple temperatures need not begin until some point shortly before an initial rise in fluorescence is expected. Detection at multiple temperatures can be done every cycle, or at some other interval, for example every fifth cycle. Eliminating multiple detection steps during the initial cycles and reducing the frequency of those steps reduces the overall time required to complete the amplification reaction. When utilizing the ratio of probe fluorescence to dye fluorescence, preferably probe fluorescence is measured over the temperatures at which the probe hybridizes to its targets, and SYBR fluorescence is measured at temperatures at which probes are unbound. Most preferably, SYBR fluorescence is measured at the extension temperature. Since the probe fluorescence increases at cycles well beyond the threshold cycle ($C_T$) value while the SYBR fluorescence plateaus, these ratios will change during the amplification reaction. Therefore, it is important to compare ratios of individual samples at a specific number of cycles past the $C_T$ value of each sample.

Figure 11:
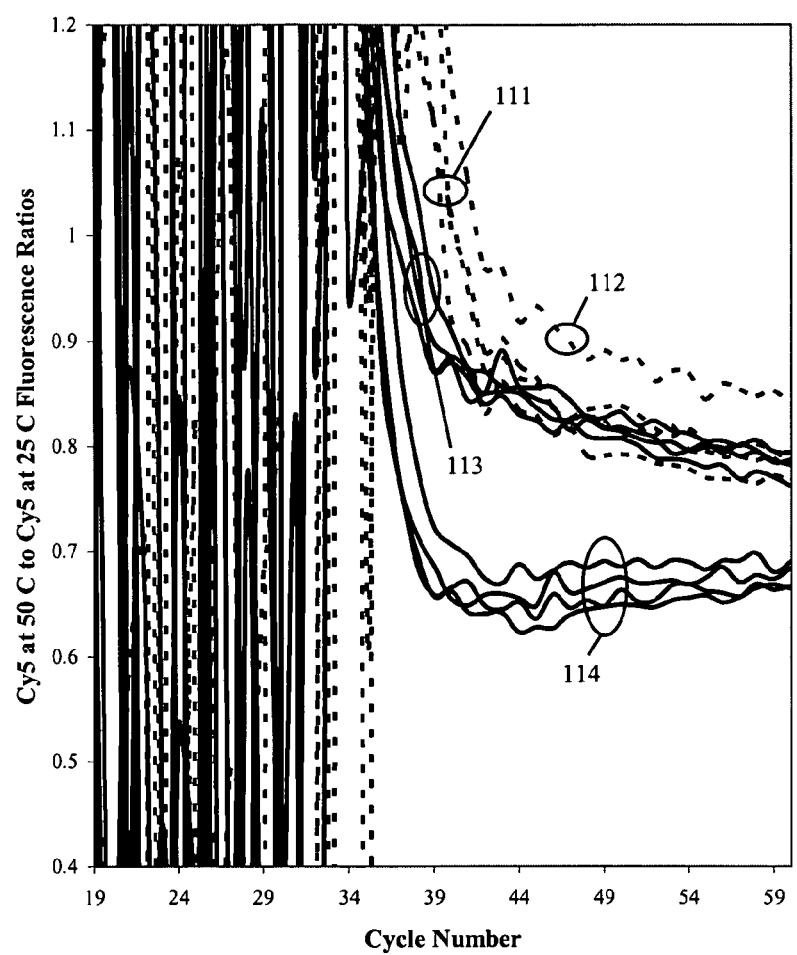
FIG. 11 shows Two Temperature Normalization assays (with background correction)

Analysis of single-stranded DNA products can also be accomplished using a single mismatch-tolerant probe whose signal is measured at more than one, for instance two or three, different temperatures. The resulting data can then be processed as ratios using the fluorescence values at two or more temperatures. The ratio significantly reduces signal differences among replicate samples and provides quantitative measure of the interrogated allele. FIG. 11 shows probe fluorescence levels at two temperatures. As illustrated in FIG. 11, probe signals arising from hybridization of the probe to the Excess Primer strand are collected at a high temperature where the probe is allele discriminating and binds only to the fully complementary allele, as well as at lower temperatures where the probe is fully mismatch-tolerant and binds to all possible allelic variants of the target sequence. Measurement of fluorescence at the high and low temperature and calculation of the resulting ratios can also be carried out as an end-point assay. We refer to these assays as "Two Temperature Normalization Assays (without background correction)." They readily distinguish homozygous and heterozygous genotypes as illustrated in FIG. 11. This type of assay can be carried out as end-point homogenous LATE-PCR assays, QE-LATE-PCR assays.

Figure 12:
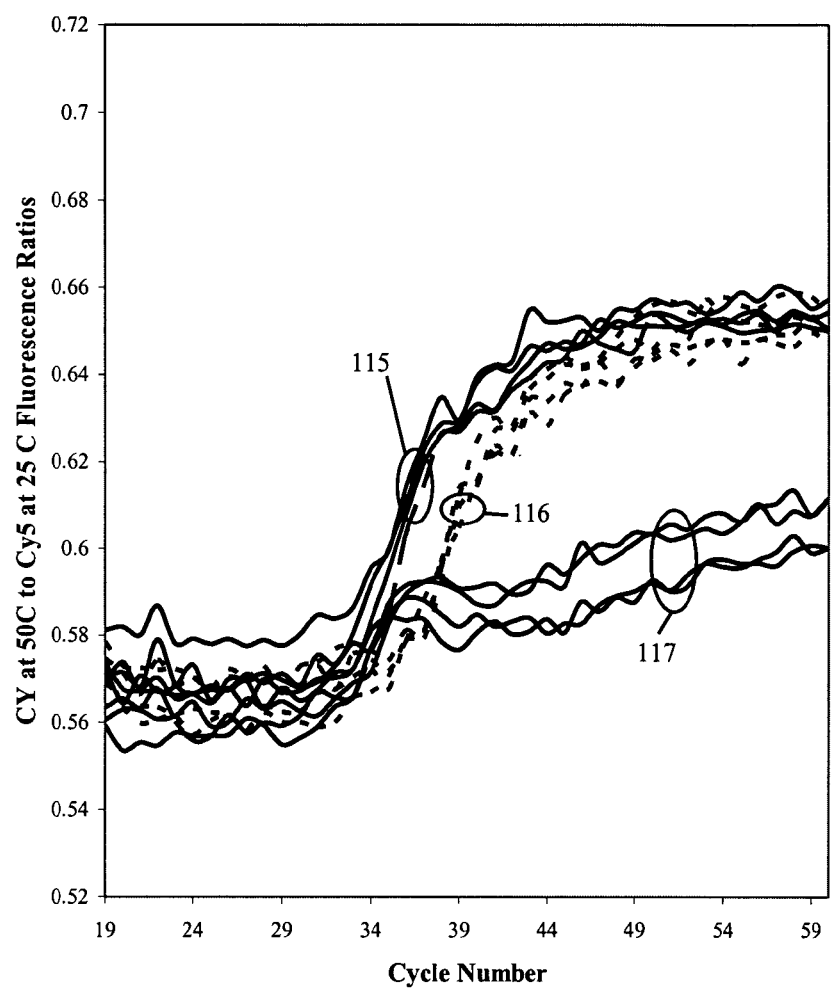
FIG. 12 shows Two Temperature Normalization assays (without background correction)

FIG. 11 reports baseline-corrected fluorescence signals. As discussed in Example 5, we prefer to use raw rather than baseline-corrected fluorescence signals from the ABI 7700, as shown in FIG. 12. Baseline correction potentially introduces artifacts into the normalized fluorescent ratios of individual samples, because the correction factor is sensitive to spurious fluctuations in the background fluorescence signals use to define baseline. Raw fluorescence readings are not subject to this artifact. Reliance on raw fluorescent signals makes the assay applicable to any PCR thermocycler with fluorimeter capabilities or to regular thermocyclers used in combination with a temperature-regulated fluorimeter for end-point fluorescence readings.

QE-LATE-PCR Genotyping can be further refined by constructing ratios of signals detected at more than two temperatures. A three-temperature method for normalizing end point data is given by the following formula: Normalized Fluorescence Value=(Fs−Ft)/(Fb−Ft), where (Ft=fluorescence at top temperature), (Fb=fluorescence at bottom temperature), (Fs=fluorescence at any given third temperature). The three-temperature method applied to homozygous and heterozygous genotypes of a SNP site within the human p53 gene is described in Example 6 and illustrated in FIG. 13.

Pyrosequencing is a real-time, isothermal, sequencing-by-synthesis method known in the art. It is catalyzed by four kinetically balanced enzymes: DNA polymerase, ATP sulfurylase, luciferase, and apyrase. The method includes a sequencing primer annealed to single-stranded DNA. Each nucleotide is dispensed and tested individually for its incorporation into the 3' end of the sequencing primer according to the sequence of the template DNA. A successful incorporation event is accompanied by release of pyrophosphate (PPi) in a quantity equimolar to the amount of nucleotide incorporated. ATP sulfurylase quantitatively converts the released PPi into ATP in the presence of adenosine 5' phosphosulfate. ATP then drives the luciferase-mediated conversion of luciferin to oxyluciferin that generates visible light in amounts that are proportional to the amount of ATP. The light is detected by a charge coupled device (CCD) camera and displayed as a peak in a pyrogram. Unincorporated dNTP and excess ATP are continuously degraded by Apyrase. Nucleotide sequence is determined from the order of nucleotide dispensation and peak heights in the pyrogram, which are proportional to the amounts of nucleotides incorporated.

LATE-PCR efficiently generates single-stranded DNA and thus eliminates the need for conventional pyrosequencing sample preparation methods required to generate single-stranded templates from traditional double-stranded PCR products. Use of LATE-PCR products for pyrosequencing, however, requires efficient removal of reagents left over from the amplification reaction (dNTP, pyrophosphate, and Excess Primers that will interfere with the pyrosequencing chemistry. Removal of leftover reagents can be accomplished by column purification, ethanol precipitation or any known approach of PCR product purification for removal of dNTP, pyrophosphate and excess primers from the amplification reaction. After cleanup, the single-stranded DNA from LATE-PCR is directly annealed to the sequencing primer and processed for pyrosequencing according to the manufacturer's instructions. It is important that LATE-PCR samples should not be heated to a temperature that denatures the double-stranded product generated in the reaction to guarantee that the only templates available to the sequencing primer are the single-stranded DNA products. In fact, it may not be necessary to heat up the LATE-PCR samples for primer annealing at all since the template DNA is already single-stranded.

We have combined LATE-PCR amplification with simplified clean-up methods to prepare samples for sequencing operations. See Example 7 and FIG. 14. We have devised two methods of LATE-PCR sample preparation for Pyrosequencing that do not involve physical PCR product purification and can be performed in a single tube. In the first method, the problem of leftover dNTPs from a LATE-PCR amplification is addressed by using limiting amounts of all dNTPs during the amplification such that dNTPs are depleted in the course of the reaction (but not prematurely so as to cause insufficient production of single-stranded DNA, namely the Excess Primer strand), which can be determined by routine experiment. The problem of leftover pyrophosphate from LATE-PCR is addressed by treating the LATE-PCR sample with an enzyme bearing a pyrophosphatase activity, for example a pyrophosphatase such as yeast pyrophosphatase, followed by heat inactivation. The Excess Primer left over from a LATE-PCR amplification should not interfere with Pyrosequencing since the matching target sequence for these primers on the 3' end of the extension product of the Limiting Primer (the Limiting Primer strand) is: A) bound-up in a double-stranded form and therefore not easily available and B) 5-20 fold less abundant than the Excess Primer strand, depending on LATE-PCR primer ratios. However, to rule out any possibility of mispriming by the Excess Primers on PCR products at the temperature used for Pyrosequencing, one may optionally add an oligonucleotide complementary to the Excess Primer at the start of LATE-PCR amplification. This complementary oligonucleotide must have a $T_m$ is at least 5-10° C. below the Excess Primer $T_m$, for instance, by being a few nucleotides shorter than the Excess Primer at its 3' end, and must be blocked at the 3' end by any method known by those skilled in the art to prevent extension of the oligonucleotide by DNA polymerases (for example, by inclusion of phosphate group). When designed in this fashion, the complementary oligonucleotide does not interfere with LATE-PCR amplification but forms a stable double-stranded hybrid with the Excess Primer at the temperature used for Pyrosequencing, thereby preventing the Excess Primer from mispriming other complementary sites on amplified material. Alternatively, the complementary oligonucleotide can have the same length or a $T_m$ that is less than 5-10° C. below that of the Excess Primer, or both, if added after the LATE-PCR reaction. Additionally, a 3' blocked oligonucleotide containing the same sequence as the Excess Primer, with or without other modifications to increase its $T_m$ (for example extra bases at the 3' end or use of LNA analogs etc.), can be added after the LATE-PCR reaction in a concentration sufficient to out-compete Excess Primers for the complementary site on the 3' end of the Limiting Primer strand.

The second method includes pretreatment of LATE-PCR samples with the same enzyme and substrate mixtures used for Pyrosequencing followed by primer annealing and addition of individual dNTPs for Pyrosequencing. In this method the order of the manufacturer's recommended protocol is reversed (i.e., the normal protocol calls for primer annealing followed by addition of Pyrosequencing reaction mix). In this method, the apyrase present in the Pyrosequencing mix degrades dNTPs while ATP sulfurylase and luciferase converts pyrophosphate into ATP and light. The luciferase and luciferin contained in these solutions provide a useful system for monitoring the breakdown of PPi as well as dNTPs. Both ATP and dATP serve as substrates for luciferase, so cessation of sample light output, as detected by the CCD camera in the Pyrosequencing machine, serves as a good approximation for cleanup. If necessary for a particular preparation, particularly if amplicons are longer than about 100 base pairs or more than about twenty base-pairs are to be sequenced, the substrates depleted by these reactions (adenosine 5' phosphosulfate and luciferin) are then replenished prior to the start of DNA sequencing. In some cases, initial treatment will require more substrate mixture than the manufacturer's protocol. In cases where heating and cooling is required for subsequent primer annealing, these reagents will be destroyed and need to be replaced prior to Pyrosequencing.

A variation of the second method is to add a purified enzyme with a dNTPase activity, for example an apyrase such as potato apyrase, and a purified enzyme with pyrophosphatase activity, for example a pyrophosphatase such as yeast pyrophosphatase, followed by heat inactivation of these enzymes, primer annealing and then conventional Pyrosequencing. Once again, leftover excess primers from LATE-PCR generally will not interfere with Pyrosequencing but in the case that they do, these primers can be dealt with using the complementary oligonucleotide strategy described above. This second method does not require adjustments of dNTP concentration for different LATE-PCR amplifications, and thus saves appreciable time.

Direct Pyrosequencing of LATE-PCR products requires 0.5-4 pmoles, sometimes 2-4 pmoles, of prepared single-stranded products annealed to 3-15 pmoles, sometimes 10-15 pmoles, of sequencing primer depending on the Pyrosequencing instrument used. In the second and third sample preparation methods, it is important that the volume of added LATE-PCR sample be less than one half, sometimes less than one third, of the total Pyrosequencing reaction to preserve the optimal pH of the Pyrosequencing mix (pH 7.5 compared to pH 8.0 or above, for example 8.3, for PCR). Alternatively, LATE-PCR products may comprise more than half the reaction volume if buffer concentration and pH are adjusted accordingly. Reagents used for monitoring the various phases of a LATE-PCR amplification, such as fluorescent DNA dyes and hybridization probes, are compatible with Pyrosequencing and do not need to be removed except when a hybridization probe is designed to bind to a region to be sequenced or where the Pyrosequencing primer binds. In this case, one of the strategies described above for blocking the Excess Primer may be employed to block the hybridization probe. We have determined that reagents to inhibit mispriming during amplification, disclosed in our concurrently filed United States Provisional patent application, titled "Reagents and Methods for Improving Reproducibility and Reducing Mispriming in PCR Amplification", are compatible with Pyrosequencing when the final concentration of these compounds in the Pyrosequencing reaction is 300 nM or below, preferably 200 nM or below, and the standard DNA polymerase for Pyrosequencing is used (exonuclease-deficient Klenow DNA polymerase fragment). By utilizing a PCR sample preparation technique that permits preparation and amplification in the same chamber or container (see, for example United States patent publication US-2003-022231-A1), in combination with a LATE-PCR amplification carried out in small volumes, preferably less than or equal to 10 μl, for example 2-10 μl, it is possible to obtain Pyrosequencing information from small groups of cells (from one to 10,000 cells) in a single-tube format. According to this "Cell-to-Sequence" assay, small groups of cells (from one to 10,000 cells) are prepared for amplification according to the PCR sample preparation technique such as those described in Pierce et al. (2002) Biotechniques 32(5): 1106-1111 (see United States patent publication US-2003-022231-A1), subjected to LATE-PCR amplification, and processed directly for Pyrosequencing in a single container, well, tube or reaction chamber as described above. As demonstrated in Example 8 below and shown in FIG. 15, the single-tube method allows for precise and accurate genotyping, even at the single cell, single molecule level.

A general concern of enzyme-based PCR cleanup approaches for Pyrosequencing is the overproduction of breakdown byproducts that may lead to feedback inhibition of enzymes during later sequencing and shorten read lengths. These include $SO_4^{2-}$, oxyluciferin, inorganic phosphate (Pi), dNMPs and AMP. One way to limit the pool of Pi and dNMPs is to reduce the concentration of dNTPs used in during PCR (though, not necessarily to the point where they are wholly consumed during the reaction as discussed above in method one). Through quantitative PCR observations on LATE-PCR amplicons up to six hundred bases long, we have found that dNTP concentrations can routinely be lowered to 100 nM without affecting amplification efficiency. Under such conditions, Pyrosequencing on enzymatically prepared LATE-PCR reactions can be accomplished for more than fifty consecutive bases as demonstrated in Example 9, FIG. 16.

In the case of dideoxy sequencing we have developed a protocol that includes dilution as the only necessary treatment of LATE-PCR amplified product. Conventional dideoxy sequencing of single-stranded amplicon from a LATE-PCR amplification by cycle sequencing requires 50 fmoles of that product and a known amount of product, as capillary electrophoresis is sensitive to the amount of product. Utilizing SYBR Green I fluorescent DNA binding dye to monitor synthesis of double-stranded DNA and a linear probe labeled with Cy5 to monitor synthesis of single-stranded amplicon, one can monitor a LATE-PCR amplification, which preferably includes a mispriming-inhibiting reagent disclosed in our United States Provisional patent titled "Reagents and Methods for Improving Reproducibility and Reducing Mispriming in PCR Amplification." None of these three additives interferes with subsequent sequencing reactions. In a LATE-PCR reaction the extent of exponential amplification and synthesis of double-stranded product is defined by the amount of Limiting Primer and is independent of the amount of starting template. The extent of single-strand production can be limited by restricting the amount of at least one dNTP or by restricting the number of amplification cycles, if desired.

We have determined that, for sequencing of the Excess Primer strand (i.e., the strand made from the Excess Primer in LATE-PCR) diluting the LATE-PCR amplification with water a total of at least 20-fold or more renders the Excess Primer strand product suitable as starting material for dideoxy sequencing. To ensure that the amount utilized with our capillary sequencer contains the required minimum amount of 50 fmoles of material to be sequenced after dilution, the linear phase of the LATE-PCR reaction must yield at least 200 femtomoles (fmoles) single-stranded DNA/microliter (µl) when the concentration of limiting primer is 25 nanomolar (nM) (25 fmoles/µl) and so about an 8-fold excess of single-stranded DNA is needed. To estimate the concentration of single-stranded DNA generated by a LATE-PCR amplification, we add to the concentration of strands present in double-stranded DNA at the end of the reaction (which participate in cycle sequencing, and whose concentration is defined by the concentration of Limiting Primer), plus the concentration of single-stranded DNA made per cycle (we estimate that in general each cycle of linear synthesis yields approximately 50% of theoretical product, the theoretical product being equal to the amount of double-stranded DNA in the reaction, times the number of cycles while the reaction remains linear. If the product accumulation stops being linear in the course of the reaction as shown by flattening of the real-time fluorescence curve for the fluorophore, the amount of single-stranded DNA made during the non-linear phase is inferred from the fold-increase in fluorescent signals between the last cycle when the reaction was linear to the final cycle of the amplification reaction. Typically, if the concentration of single-stranded product produced in a LATE-PCR amplification is 200 fmoles/ul, we dilute the Excess Primer strand 1:8 to 25 fmoles/ul and use 2 ul of diluted products (50 fmoles) directly into a 20 ul dideoxy sequencing reaction. Under these conditions the total dilution factor of LATE-PCR products into the sequencing reaction is 80-fold. One can use as much as 8 µl of diluted LATE-PCR products (200 fmoles) into the sequencing reaction for a total dilution of 20 fold and still obtain interpretable sequence chromatograms.

Sample purification is necessary because leftover reagents from PCR amplification, such as dNTP and primers, will interfere with dideoxy sequencing. LATE-PCR replaces sample preparation by ethanol precipitation or affinity columns with a simple dilution step in water. Preparation of LATE-PCR for dideoxy sequencing only requires dilution of excess single-stranded DNA products in water at least 8-10 fold to a concentration of 25 fmoles/µl, followed by addition of 50-200 fmoles single-stranded DNA product to a dideoxy-cycle sequencing reaction containing 10 pmoles sequencing primer. The total dilution factor in the final dideoxy sequencing mix is at least 20-fold. Under these conditions, leftover dNTPs from LATE PCR are too diluted to interfere with dideoxy sequencing. Carryover Excess Primer from LATE-PCR is also not a problem, because the template to which these primers bind, the Limiting Primer strand, is present at a very low concentration after the dilution step and is fully hybridized to the Excess Primer strand. For these two reasons the Excess Primer does not serve as a sequencing primer. Example 10 and FIG. 17 demonstrate the effectiveness of our "dilute and go" method. FIG. 17 presents sequence chromatographs obtained using symmetric PCR and the traditional sample preparation method (purification of DNA products using Qiagen columns, followed by quantification by gel electrophoresis; total preparation time: 1 hr), and sequence chromatographs obtained using LATE-PCR and dilution in water (total preparation time: 30 seconds). The sequence chromatographs are nearly identical.

Figure 18:
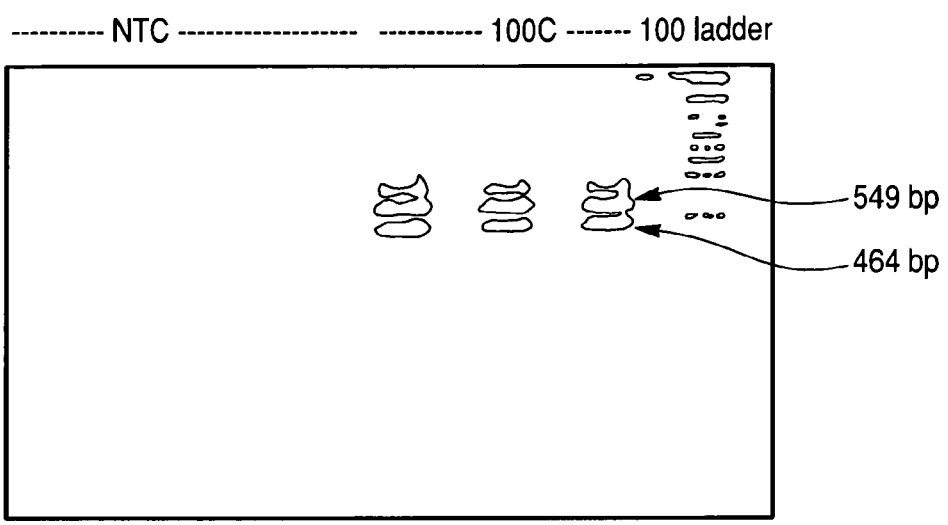
FIG. 18 is an electrophoresis gel from a LATE-PCR amplification of more than one product from the same DNA template in the same reaction.
Figure 19:
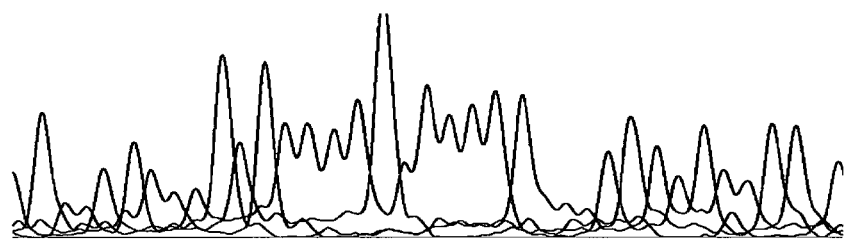
FIG. 19 is chromatographs ((A) SEQ ID NO: 47, (B) SEQ ID NO: 48, (C) SEQ ID NO: 49, and (D) SEQ ID NO: 50) from dilute-and-go dideoxy sequencing of the product of the LATE-PCR amplification of FIG. 18.
Figure 19:
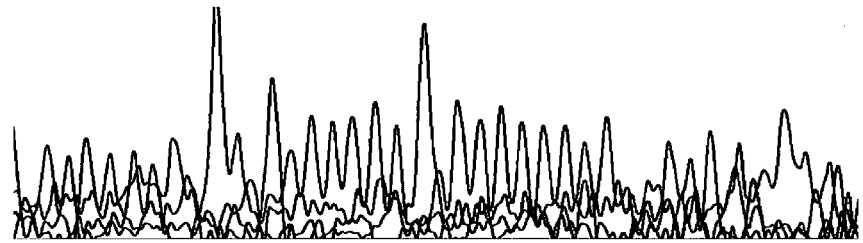
Figure 19:
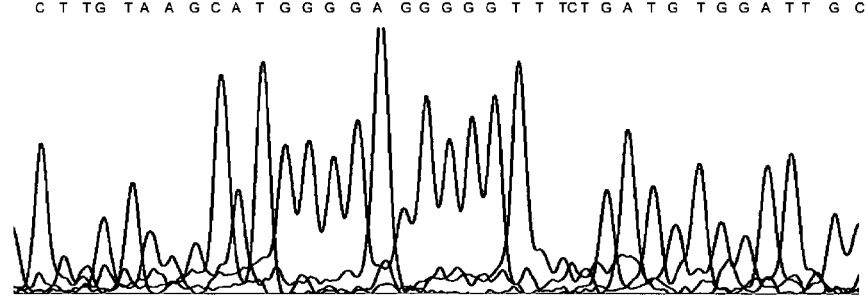
Figure 19:
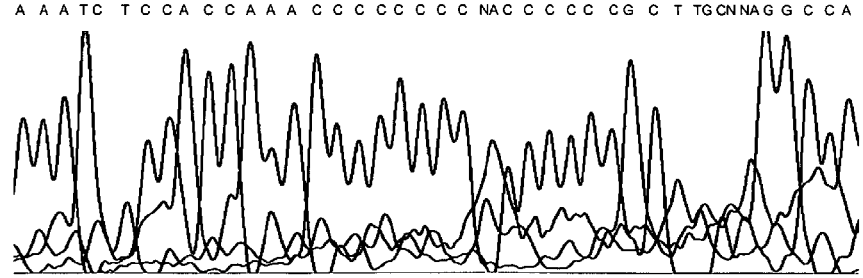

Example 11 and FIGS. 18-19 illustrate strategies for LATE-PCR amplification of more than one product from the same DNA template in the same reaction. Thus, these reactions contain two pairs of primers (each comprised of an Excess Primer and a Limiting Primer) that amplify two separate sequences within a contiguous template. The two pairs of primers can be arranged such that both Excess Primers and both Limiting Primers hybridize to the same strand of the template, or to opposite strands of the template. As one versed in the art will appreciate, when like primers hybridize to opposite strands of the template the two Excess Primers can extend either "inwardly" or "outwardly" on their respective template stands. FIG. 19 also shows that sequences of both Excess Primer strands can be obtained from the same reaction mixture via the "dilute-and-go" method.

Figure 20:
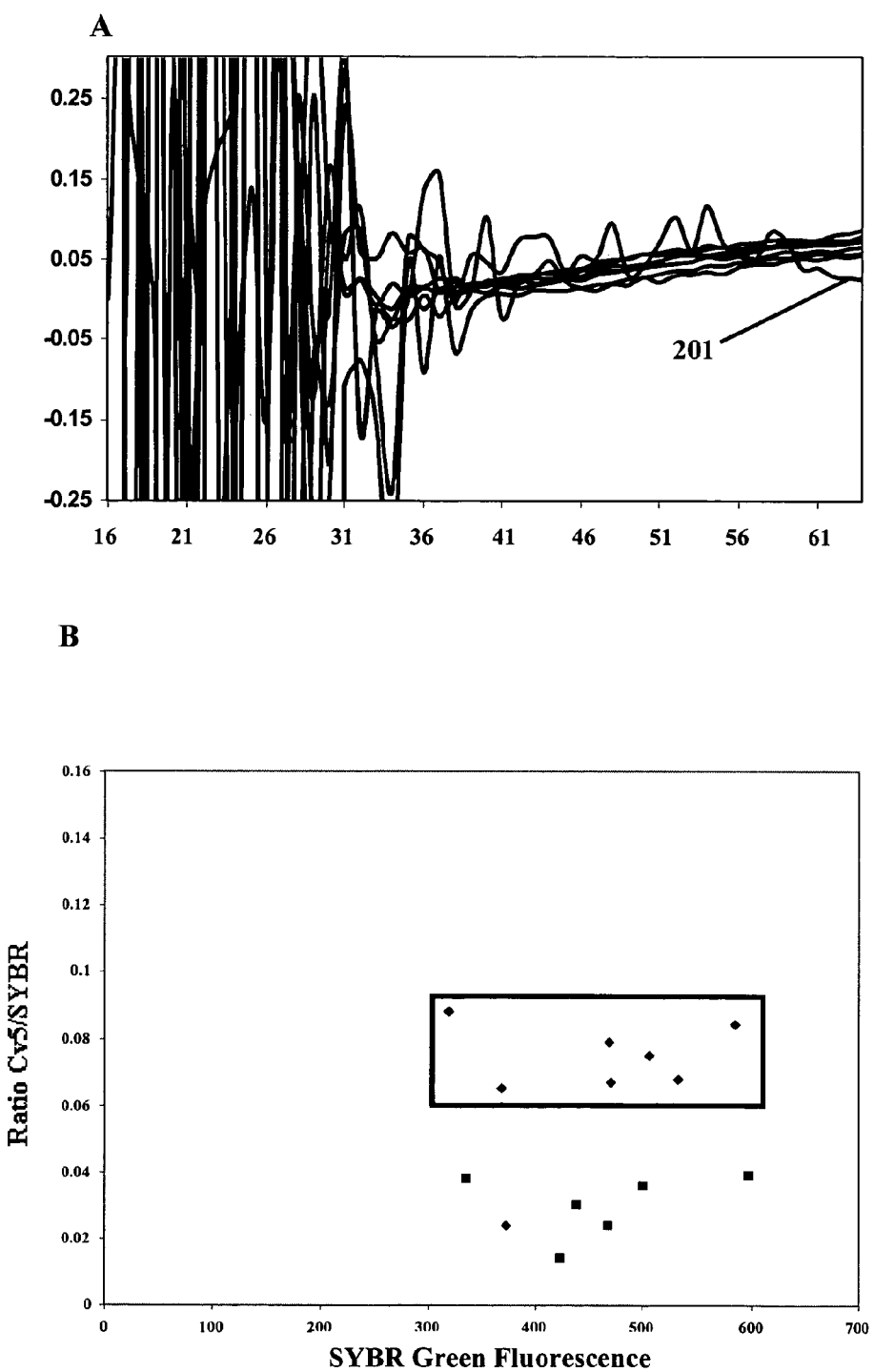
FIG. 20 shows that (A) the amount of ssDNA and dsDNA generated by a LATE-PCR amplification can be measured independently and (B) can be used to calculate the ratio ssDNA/dsDNA which, in turn, can be used to determine whether the amount of ssDNA thus far accumulated is sufficient for subsequent sequencing via the "dilute-and-go" method.

Example 12 and FIG. 20 show that the amount of ssDNA and dsDNA generated by a LATE-PCR amplification can be measured independently and can be used to calculate the ratio ssDNA/dsDNA which, in turn, can be used to determine whether the amount of ssDNA thus far accumulated is sufficient for subsequent sequencing via the "dilute-and-go" method.

Figure 21:
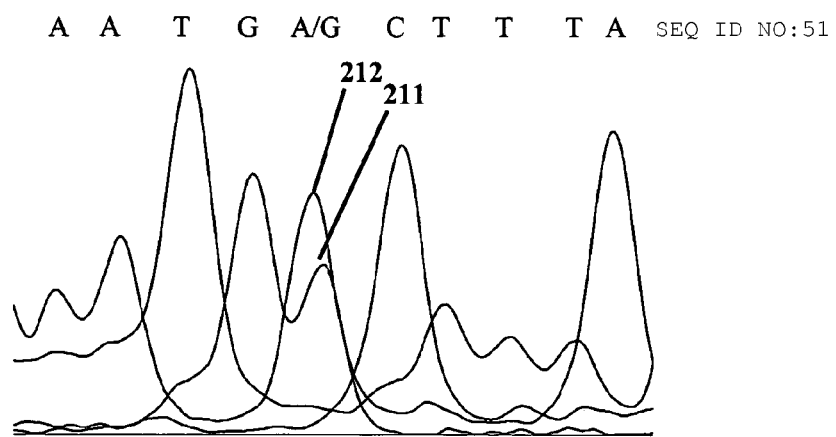
FIG. 21 is dideoxy sequencing chromatographs resulting from the "dilute-and-go" method employed on a 50:50 mixture of LATE-PCR amplicons having two closely related, but different sequences.
Figure 22:
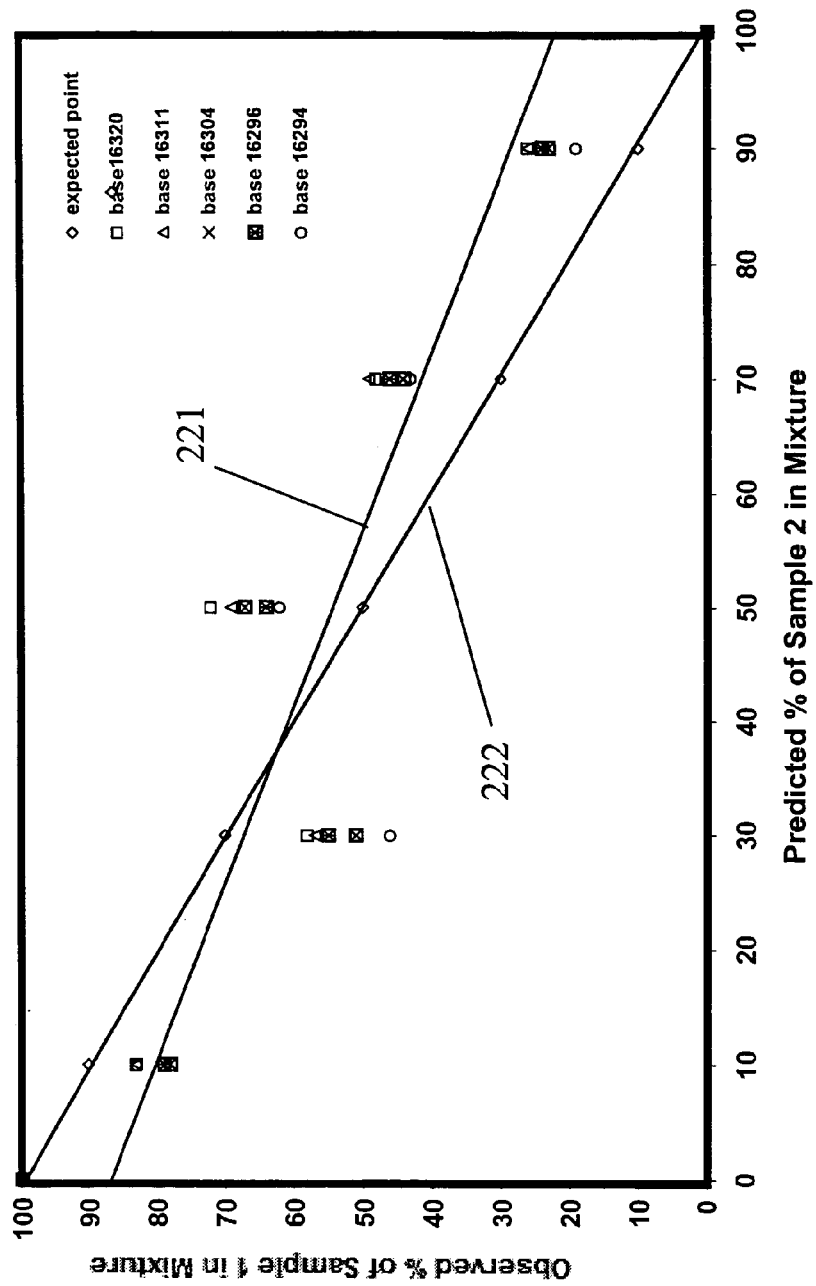
FIG. 22 shows the sensitivity range of mixed LATE-PCR amplicons having closely related, but different sequences that can be distinguished via the "dilute-and-go" method.

Example 13 and FIG. 21 show the "dilute-and-go" method employed on a 50:50 mixture of LATE-PCR amplicons having two closely related, but different sequences. FIG. 22 shows that mixtures comprised of 90:10 and 10:90 ratios of two LATE-PCR amplicons having closely related, but different sequences can be distinguished from pure 100:0 and 0:100 mixtures as well as 30:70 and 70:30 mixtures via the "dilute-and-go" method. In order to accomplish this type of analysis it is necessary to correct the observed amplitudes of each nucleotide peak at each heterplasmic position in terms of the expected amplitude of the equivalent "pure" nucleotide at that position. Once this is done, relative amounts of each sequence can be calculated as the ratio of amplitudes (corrected nucleotide 1)÷(corrected nucleotide 1+corrected nucleotide 2). Thus, as in the case of mitochondrial DNA sequences that differ, LATE-PCR and dideoxy "dilute-and-go" methods described herein can be used to detect heteroplasmy. The dideoxy method for measuring heteroplasmy is particularly advantageous because it can be used to survey many hundreds of nucleotides in a single analysis. Although not wishing to be bound by any theory, we believe that the methods described herein work, in contrast to previous attempts based on symmetric PCR and dideoxy-sequencing, because LATE-PCR generates highly homogeneous populations of single-stranded amplicons. Symmetric PCR in contrast tends to generate populations of full length molecules together with some partial amplicons and some mispriming amplicons.

Figure 23:
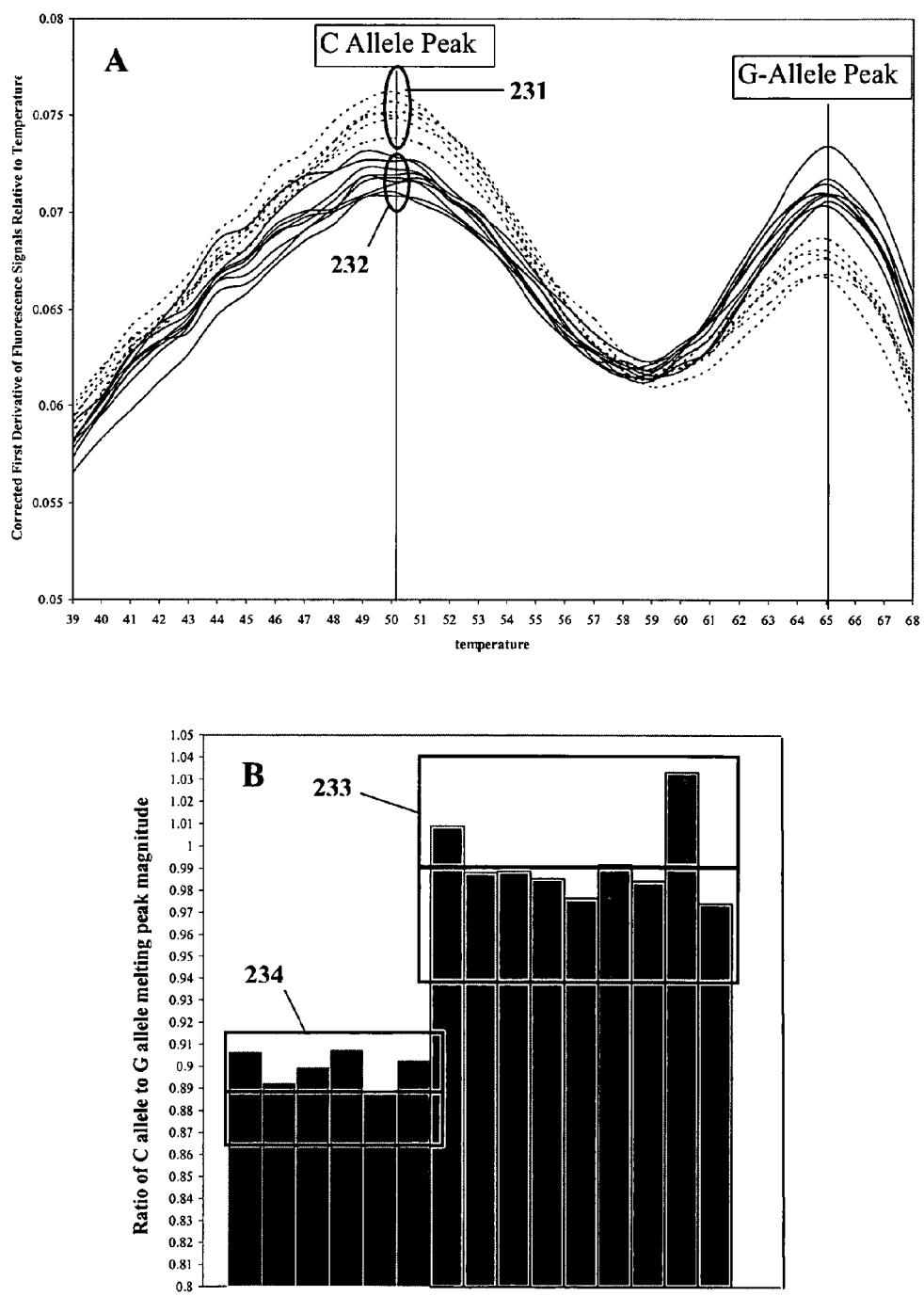
FIG. 23 shows that a LATE-PCR together with at least one single mismatch-tolerant probe can be used to (A) generate end-point melting curves which, in turn, can be used to (B) quantify the relative amounts of two or more mixed LATE-PCR amplicons having closely related, but different sequences.

Example 14 and FIG. 23 show that a LATE-PCR together with at least one single mismatch-tolerant probe can be used to generate end-point melting curves which in turn can be used to quantify the relative amounts of two or more mixed LATE-PCR amplicons having closely related, but different, sequences. Quantitative end-point melting analysis (QE) LATE-PCR of mixtures of related amplicons is made possible by virtue of the fact that LATE-PCR generates single-stranded products. Thus, when one or more labeled mismatch-tolerant probes are present in the reaction, the probe(s) hybridize first to the most complementary target sequence and then, if the temperature is lowered sufficiently, to all related target sequences. Thus each probe/target hybrid in the set has its own melting temperature and the magnitude of the melting peak derived from each probe/target hybrid accurately reflects the amount of each accumulated target sequence. Quantitative measurements of either the amplitude, or two dimensional area of each melting curve can then be used to calculate the relative abundance of each target sequence. The data shown in FIG. 23 demonstrate that this method can be used with 99.7% confidence to distinguish between 0:100-10:90-50:50-90:10-100:0 mixtures of two sequences that differ by a single nucleotide.

Figure 24:
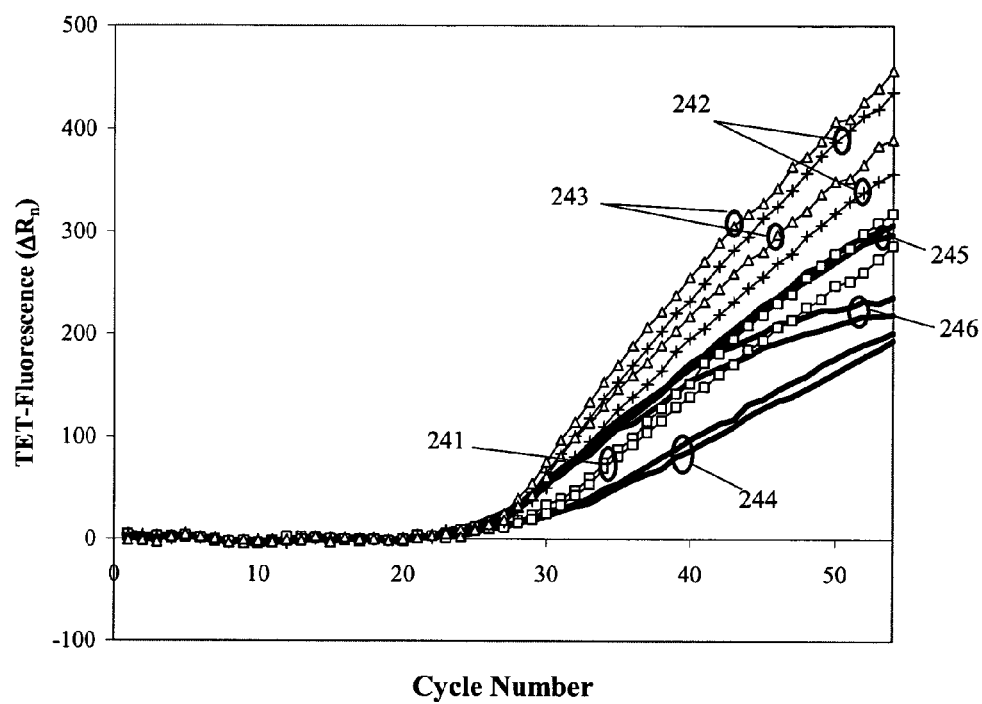
FIG. 24 shows the kinetics of several LATE-PCR assays carried out using two different concentrations of Taq polymerase with each of three different amounts of genomic DNA.

Assays according to this invention, whether carried out in the presence or absence of the reagent described in our U.S. Provisional patent application 60/619,620 can be independently optimized to avoid or minimize mispriming by adjusting the concentration of the DNA polymerase, for example Taq polymerase, added to the reaction. Decreasing mispriming by adjusting polymerase can be observed in terms of the kinetics of the LATE-PCR reaction using a probe of the ssDNA, as well as by the composition of the final product revealed by various means known in the art. We have found that it is experimentally convenient to start with a typical excess concentration of Taq polymerase and then to decrease this concentration in steps. While too little polymerase can cause the reaction to become inefficient (manifest as a significant decrease in the rate or extent of product amplification), optimal levels of polymerase results in a LATE-PCR amplification assay with efficient dsDNA amplification and sustained ssDNA synthesis over many cycles. Example 15 demonstrates that the optimal level of polymerase can be judged by the dsDNA signal observed using a double-strand dye such as SYBR Green plus the melting curve of the dsDNA product, also observed using SYBR Green. Example 16 and FIG. 24 show that when such assays are probed for a specific ssDNA product generated from different amounts of starting material, the resulting plots are linear and parallel over many cycles of ssDNA production.

EXAMPLES

Example 1. Binding Dye Versus Binding Dye Plus Labeled Primers

To compare the performance of an intercalating dye to the performance of the dye used in combination with a primer that includes an interacting fluorophore, an extension assay was performed. The dye utilized was SYBR Green I at a dilution of 1:40,000.

Three nucleotide strands were included. A DNA template, an extendable DNA primer (5' labeled with Cy5, complementary to the template, and having a $T_m$ of 60° C.), and a non-extendable DNA oligonucleotide (3' end blocked with a phosphate group) also complementary to the target, at a location 3' to the primer, also labeled with Cy5 fluorophore, and having a higher $T_m$ of 79° C. The spacing between the primer and the non-extendable nucleotide was chosen such that primer extension products up to the non-extendable oligonucleotide would all have $T_m$'s below 79° C.

The reaction mixture for the primer extension assay included 0.5 micromolar (μM) template DNA, 1.5 μM primer and 1.5 μM of the non-extendable oligonucleotide. The mixture also included 1×PCR buffer, 3 millimolar (mM) $MgCl_2$, 250 nanomolar (nM) of each dNTP, 1:40,000× SYBR Green I, and Taq DNA polymerase. The reaction mixture was heated to 50° C. for 2 minutes so as to bind the primer and the non-extendable oligonucleotide, and to generate primer extension products short of reaching the non-extendible oligonucleotide. Duplicate samples were run.

Following the primer-extension reaction, the product was subjected to melt analysis in which the SYBR Green dye was excited as the temperature was changed. Fluorescence readings were taken at the wavelength of the dye's emission and at the wavelength of the fluorophore's emission as the temperature was increased through the range of melting temperatures encompassing the unextended primer and the non-extendable oligonucleotide. Melt curves, the first derivative of fluorescence with respect to temperature plotted against temperature, are presented in FIG. 1, wherein Panel A presents the curves 1 for the two samples, data from dye emissions and Panel B presents curves 2 for the two samples, data from Cy5 emissions.

Example 2. Quenched Mismatch-Tolerant Probes

Figure 3:
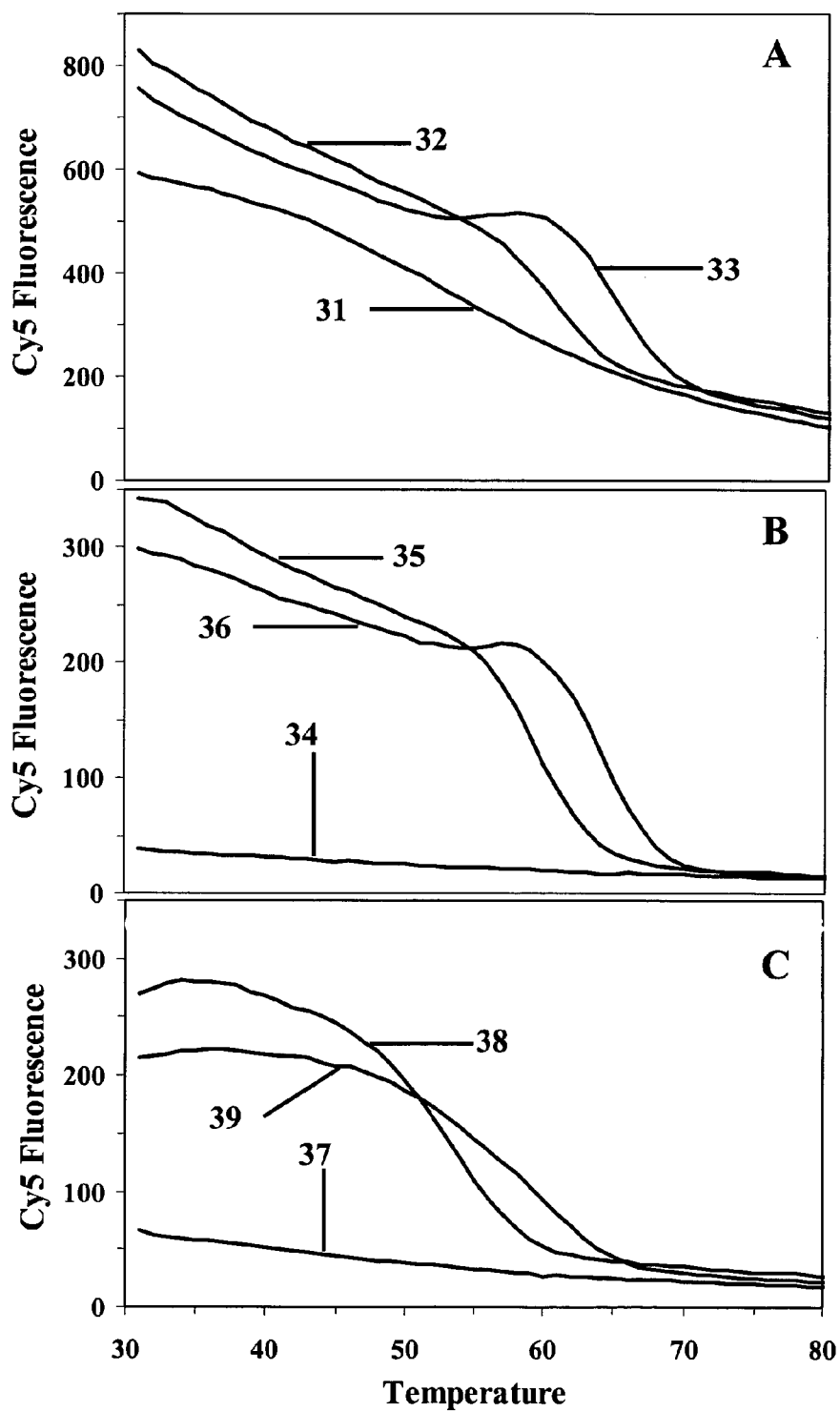
FIGS. 3A, 3B, and 3C show comparison of identification of five species of Mycobacteria via melting curve analysis obtained with either conventional mismatch-tolerant probes against the 16S ribosomal RNA gene or two different versions of quenched mismatch-tolerant probes against the same target designed according to the methods of the invention.

A labeled probe was designed to have a consensus sequence complementary to the 16S ribosomal RNA gene of Mycobacterium. Secondary structure was predicted according to the Mfold programs (Zucker, M (2003), "Mfold web server for nucleic acid folding and hybridization prediction," Nucleic Acids Res 31: 3406-3415) with sodium concentration set at 70 millimolar (mM) and magnesium concentration set at 3 mM. The sequence of the probe was Cy5-AATACTGGATAGGACC ACG AGG (SEQ. ID No. 1), with predicted secondary structure formed by hybridization of the underlined regions. The predicted $T_m$ of the probe's secondary structure was 37° C. This probe was tested in samples containing no target, *M. gordonae*, or *M. asiaticum* in mixtures containing SYBR Green I dye, wherein the dye was excited directly and the fluorophore was in turn excited indirectly. Results of Cy5 fluorescence versus temperature are presented in FIG. 3, Panel A. Line 31 (no target) shows high background fluorescence but line 32 (*M. gordonae*) and line 33 (*M. asiaticum*) show discernable signals above background. To quench the background fluorescence, a non-fluorescent quencher (a Black Hole™ II quencher) was added to the 3' terminal nucleotide of the probe. The modified probe was similarly tested, and the results are shown in Panel B of FIG. 3. As can be seen, background fluorescence (line 34, no target) dropped markedly, and the signals from *M. gordonae* (line 35) and *M. asiaticum* (line 36) were much higher above background.

Another technique for quenching a probe is to construct the probe to have a hairpin structure terminally labeled with an appropriate fluorophore on one end and a quencher on the other. We constructed a probe having the sequence Cy5-CTGGATAGGACCACGAGGCCAG-BHQII (SEQ. ID. No. 2), wherein the underlined sequences are complementary and form a hairpin stem. We added the three 3'-terminal nucleotides for the purpose of achieving the stem. The predicted melting temperature of this probe with a perfectly matched target is 60° C. The predicted $T_m$ of the stem is about 48° C. (based on the predicted unmodified nucleotide stem $T_m$ of 40° C. not accounting for the increased affinity of the fluorophore-quencher interaction). This probe was also tested as described above, and the results are presented in Panel C of FIG. 3. Background fluorescence (line 37, no target) was quite low, and the signals from *M. gordonae* (line 38) and *M. asiaticum* (line 39) were high above background.

Example 3. Real-Time and End-Point Genotyping Using Mismatch-Tolerant Probes

This example illustrates identification of homozygous samples and heterozygous samples for the G269 allele of the human Hexosaminidase A (Hex A) gene responsible for Tay-Sachs disease using real-time LATE-PCR amplification and a Cy5-labeled, low-$T_m$, mismatch-tolerant linear probe excited indirectly by emission from a SYBR dye. Probe hybridization was monitored twice during each amplification cycle within the detection temperature space of LATE-PCR, first at 55° C., a temperature at which the probe is allele-discriminating in this assay and binds exclusively to its perfectly matched target, and then at 40° C., a temperature at which the probe is mismatch-tolerant and binds to the totality of alleles of its target sequence in the amplification reaction. Detection of specific alleles and total alleles with the mismatch tolerant probe permits correction of stochastic tube-to-tube variations in amplicon yield among replicate samples. The ratio of allele-specific-to-total alleles in the reaction (Cy5 at 55° C./Cy 5 at 40° C.) allows normalization of replicate sample for end-point genotyping. Genotypic information is derived from the ratio values. In the case of homozygous samples, probe signals detected under allele-discriminating conditions are the same as probe signals detected under mismatch-tolerant conditions, since in both cases the probe is binding to 100% of the target sequence alleles. In contrast, in the case of heterozygous samples, probes signals detected under allele-discriminating conditions are half as intense as probe signals detected under mismatch tolerant conditions, since the probe is binding to only 50% of the target sequence alleles under allele-discriminating conditions but to 100% of the alleles under mismatch tolerant conditions. Hence, homozygous samples have higher Cy5 at 55° C./Cy 5 at 40° C. ratios than heterozygous samples. This method of genotyping only relies on detection of a single allele.

The sequences and the concentration adjusted melting temperature, $T_{m[0]}$, of the LATE-PCR primers and the probe are as follows. The Limiting Primer has the sequence 5'CGAGGTCATTGAATACGCACGGCTCC 3' (SEQ. ID No. 17). It has a concentration adjusted $T_{m[0]}$ of 63.2° C. at 25 nM. The Excess Primer has the sequence 5' TAACAAGCAGAGTCCCTCTGGT 3' (SEQ. ID No. 4). It has a concentration-adjusted $T_{m[0]}$ of 61.8° C. at 1 µM. The probe has the sequence 5' Cy5-GGGACCAGGTAAGAA 3' (SEQ. ID No. 5). It has a $T_m$ of 56.3° C. It is a Low-$T_m$ probe and when used with a 65° C. annealing temperature, also a Super-Low-$T_m$ probe.

Figure 7:
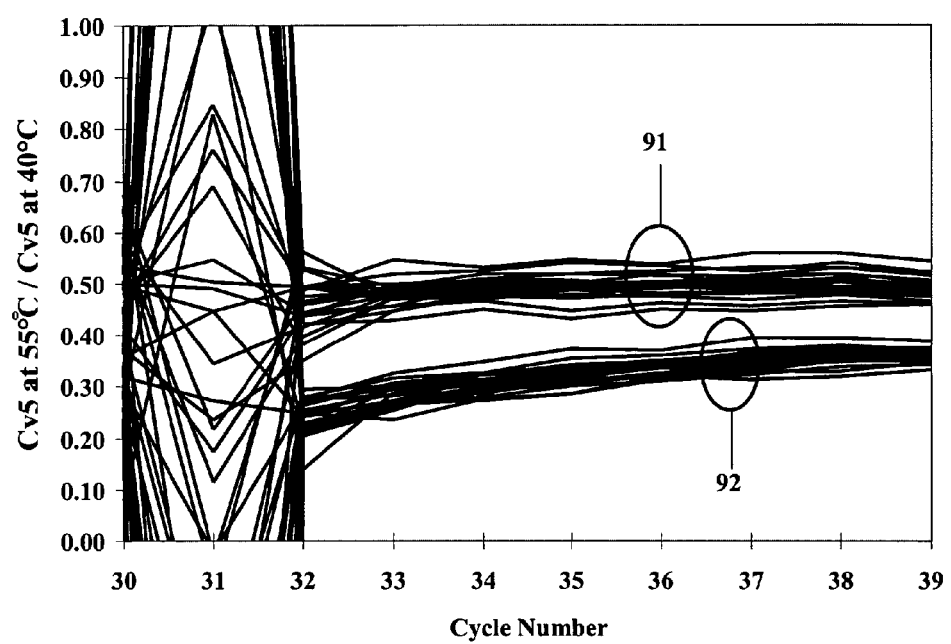
FIG. 7 shows end-point genotyping of homozygous and heterozygous samples for the G269 mutation of the human HexA gene using LATE-PCR and a single Low-$T_m$ mismatch-tolerant probe against the wild-type allele according to the methods of the invention.

Replicate LATE-PCR assays (n=15) were set up for each different genotype (homozygous G269 and heterozygous G269) in 1×PCR buffer, 3 mM MgCl$_2$, 250 micromolar (µM) dNTP, 25 nM limiting primer, 1000 nM excess primer, 1.25 units Taq DNA polymerase, 0.6 µM Cy5-labeled probe, and a 1:40,000 dilution SYBR Gold I. PCR cycles parameters were 95° C. for 3 minutes, then 25 cycles at 95° C. for 10 sec, 65° C. for 20 sec, and 72° C. for 20 sec, followed by 30 cycles at 95° C. for 10 sec, 65° C. for 20 sec, 72° C. for 20 sec, 55° C. for 20 sec, and 40° C. for 20 sec with fluorescence acquisition at 55° C. and 40° C. in the Cy5 channel. FIG. 7 shows analysis of the ratios of Cy5 signals at 55° C. to the Cy5 signals at 40° C. and demonstrates that these ratios are suitable for end-point genotyping for any amplification cycle past the probe detection threshold. In this figure, homozygous samples (circle 91) have ratios approximately twice the ratio of heterozygous samples (circle 92).

Example 4. Analysis of Multiple Targets Using Target-Specific Probes with Different Melting Temperatures Multiple probes, each labeled with the same fluorophore, can be used in combination to detect and quantify different sequences along a single, longer oligonucleotide (for example, a product of asymmetric PCR, LATE-PCR, or rolling circle amplification,) or on different oligonucleotides. The use of Low-$T_m$ probes increases the specificity for such targets, greatly reducing or eliminating signals generated from mismatched targets. One possible application of this technology is genotyping human DNA to identify known alleles that cause genetic disease. This example describes temperature analyses for probe design and for detection of products.

As a starting point we chose the following targets that potentially could be present in an amplification product: the normal sequence of the cystic fibrosis transmembrane regulator (CFTR) gene in the region that encodes amino acid 542 of the protein; the sequence of the Delta F508 mutation, the most common CFTR mutation; and the normal sequence corresponding to the Delta F508 mutation.

Figure 8:
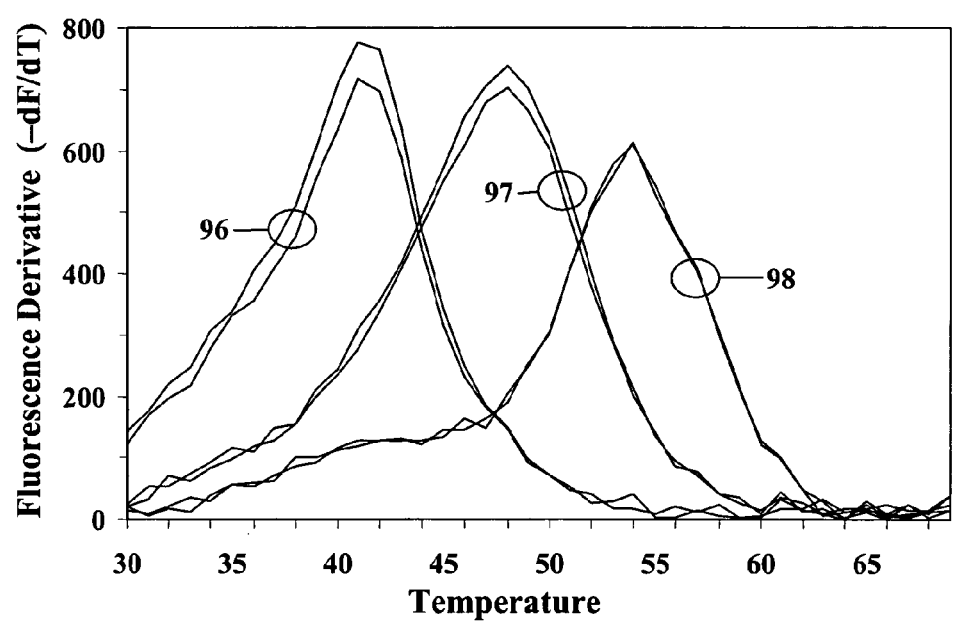
FIG. 8 shows separate identification of three different alleles of the human cystic fibrosis transmembrane regulator (CFTR) gene using LATE-PCR, allele discriminating Low-$T_m$ probes labeled with the same color, and first-derivative analysis of melting curves.

We designed Low-$T_m$ allele-discriminating probes for each of the three target sequences. The probes were low-temperature molecular beacon probes, each labeled with the fluorophore FAM and a quencher. The three probes were designed to have different $T_m$'s versus their targets in mixtures containing 70 mM Tris-HCl and 3 mM MgCl$_2$. The "542 probe" had a $T_m$ of 40° C. (predicted value 41° C. by nearest neighbor calculation); the "508 normal probe" had a $T_m$ of 47° C. (predicted value 46° C. by nearest neighbor calculation); and the "Delta F508 probe" had a $T_m$ of 54° C. (predicted value 53° C. by nearest neighbor calculation). FIG. 8 presents the melting curves from which the $T_m$ values were obtained. FIG. 8 shows the negative first derivative of fluorescence readings as a function of temperature for the 542 probe (line 96), the DF508 probe (line 97) and the 508 normal probe (lines 98) for duplicate samples. Roughly equal peak heights were obtained by using target concentrations of 1 µM, and 542 probe concentration of 2 µM. We tested each probe against mismatched target to check allele discrimination, and we found that fluorescence against perfect was 5-10 times the fluorescence against mismatched target.

It can be seen from FIG. 8 that even small $T_m$ differences would have been easily resolvable. From a plot such as FIG. 8, differences of 4-5° C. would be resolvable. Deconvolution utilizing software supplied with real-time PCR thermal cyclers might permit resolution of $T_m$'s differing by half that amount.

Figure 9:
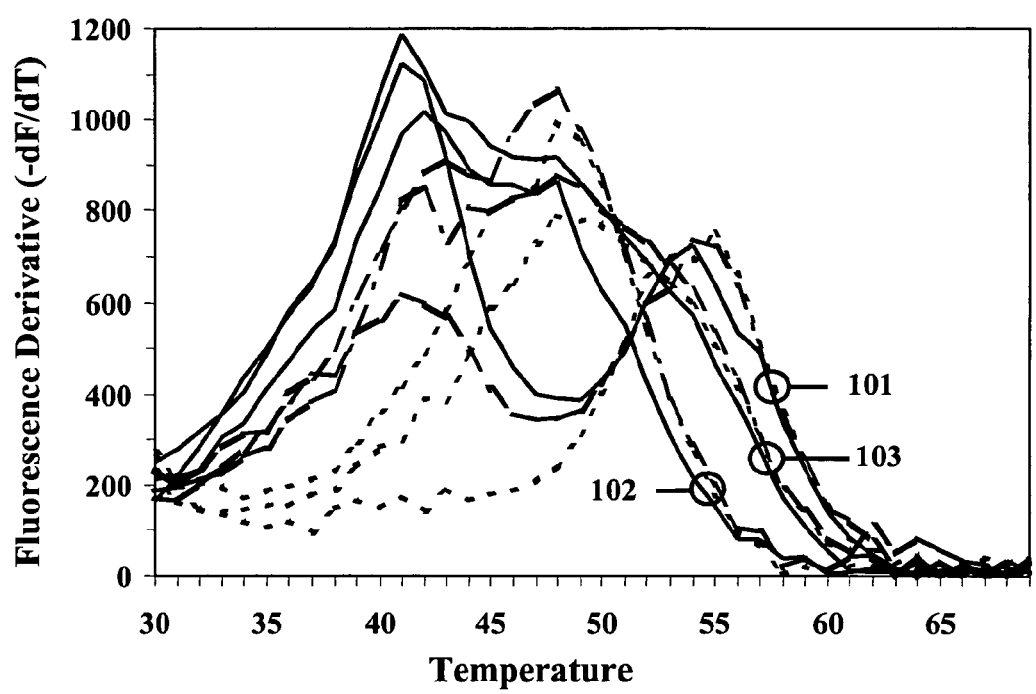
FIG. 9 shows simultaneous identification of different combinations of various alleles of the human cystic fibrosis transmembrane regulator (CFTR) gene using allele discriminating Low-$T_m$ probes labeled with the same color, and first-derivative analysis of melting curves.

Examining the negative first derivative of the fluorescence is one method to determine which oligonucleotide targets are present in a given sample. FIG. 9 shows such an analysis, utilizing fluorescence above background. Samples containing the normal 508 target, but no Delta F508 target (circle 101) have a melting peak at 54° C., indicative of that molecular beacon-target hybrid. Samples containing the Delta F508 target, but no normal target (circle 102) have a melting peak at about 47° C., indicative of hybridization to the beacon with the mutant sequence. Samples containing both of those targets (circle 103) have a broad peak over that range of temperatures, indicating fluorescence from both molecular beacon-target hybrids. The presence and relative concentration of the normal sequence at the 542 amino acid is indicated by the presence and relative height of the melting peak at about 40° C. Samples with 542 normal target (solid line for each numbered group) have a large peak at that temperature, samples with 542 mutant target containing a single nucleotide change in this region identical to the second most common CFTR mutation (stippled line for each numbered group) have no peak at that temperature, and samples with both 542 targets (dashed line for each numbered group) have peaks of intermediate height. The height of the peak in samples with both 542 targets is affected by the presence of the neighboring Delta F508 melting peak.

Figure 10:
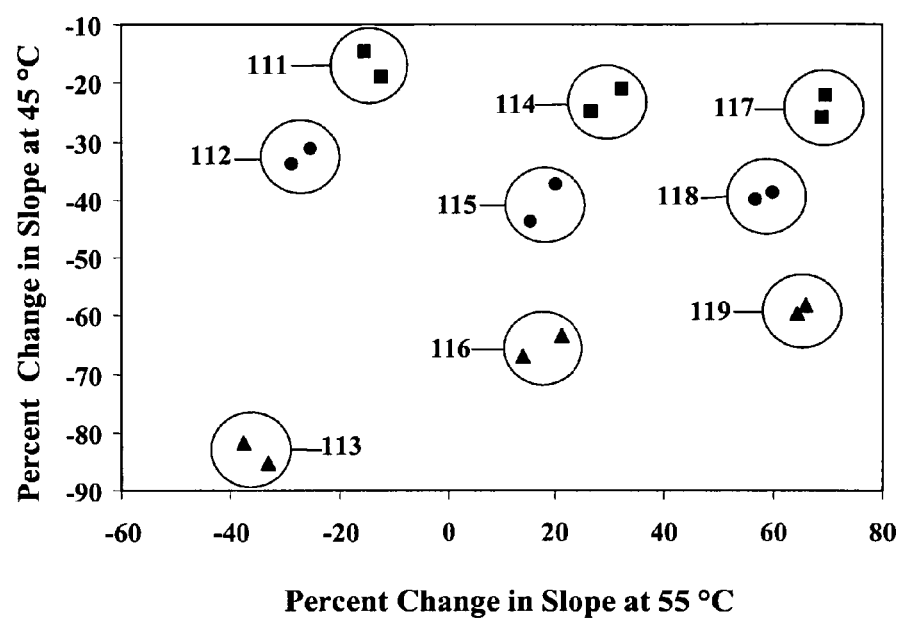
FIG. 10 shows identification of different allele combinations of the human cystic fibrosis transmembrane regulator (CFTR) gene by plotting the changes in fluorescence at two temperatures collected according to the methods of the invention.

It may not always be possible or desirable to obtain a complete melting profile during the course of an amplification reaction. Further analysis of the samples described above shows that a limited number of detection steps could provide the information required to identify the specific oligonucleotides in a mixture. Decreasing, rather than increasing temperature can be used. Samples were heated to 70° C., and then lowered in 5° C. decrements to 30° C. with a 30 second detection at each step. Samples containing the normal 508 target but no Delta F508 target, or containing the Delta F508 target but no normal target could be distinguished based on changes in fluorescence between 60° C. and 50° C. Each combination of target oligonucleotides produced a unique pattern of fluorescence change. A scatter plot of the percent change in fluorescence increase at 55° C. vs. the percent change in fluorescence increase at 45° C. is shown in FIG. 10. This analysis distinguishes the combination of targets that are present in each sample. By using the changes in fluorescence rather than the fluorescence intensity itself, an accurate evaluation can be made even when samples differ considerably in the total concentration of targets, as might occur in replicate amplification samples. FIG. 10 includes duplicate samples for each combination of normal 508 plus normal 542 targets (marks circled 111), normal 508 plus both 542 targets (112), normal 508 plus mutant 542 targets (113), both 508 plus normal 542 targets (114), both 508 plus both 542 targets (115), both 508 plus mutant 542 targets (116), Delta 508 plus normal 542 targets (117), Delta 508 plus both 542 targets (118), and Delta 508 plus mutant 542 targets (119). A similar analysis could be done using this temperature profile during each cycle or selected cycles of an amplification reaction. Several samples with DNA of known genotypes could be amplified and the detection data used to establish an expected range of values. This would provide a method for rapid determination of genotypes from unknown samples.

Although only 3 probes were used in this example, the combined use of much higher number of probes is possible. The main limitations on the total number of probes are the temperature range for detection and the minimum $T_m$ difference between the probe-target hybrid. These are in turn dependent on the nature of the amplification reaction and the capabilities of the equipment and deconvolution software. For example, 10 different probe-target combinations could be distinguished over a 30 degree temperature range if the minimum $T_m$ difference for deconvolution is 3 degrees. This number can be increased several fold by using multiple fluorophores.

Example 5. Two Temperature Normalization with and without Background Correction

QE LATE-PCR genotyping of the rs858521 SNP was performed with unknown DNA samples and homozygous control rs858521 (CC alleles) and heterozygous control (CG alleles) using a single Cy5-labeled mismatch-tolerant probe. Amplification and detection were performed using an ABI Prism Sequence Detector 7700 (Applied Biosystems, Foster City, Calif., U.S.A.), which normally generates baseline-corrected fluorescent signals. For our analysis utilizing ratios, however, fluorescent signal ratios were obtained both from baseline-corrected fluorescence signals (FIG. 11) and from raw fluorescent signals (FIG. 12). FIG. 11 presents the ratio of the probe's fluorescence at 50° C. to its fluorescence at 25° C. as a function of the amplification reaction's cycle number utilizing the instrument's baseline-corrected fluorescent signals. In FIG. 11, circle 113 is replicates of the homozygous control, circle 114 is replicates of the heterozygous control, while circles 111 and 112 are the unknowns. FIG. 12 presents the same results utilizing raw fluorescence signals. In FIG. 12, circle 116 is replicates of the homozygous control, circle 117 is replicates of the heterozygous control, and circle 115 is the unknowns. The use of baseline-corrected fluorescence signals for normalization resulted in ambiguous genotyping for one sample FIG. 11, circle 112. In contrast, use of raw fluorescence signals for normalization provided the correct genotyping for all samples. This result demonstrates that baseline-correction in the ABI Prism 7700 Sequence Detector software can introduce artifacts that affect signal normalization and preferably should not be used.

Example 6. Three Temperature Normalization

Figure 13:
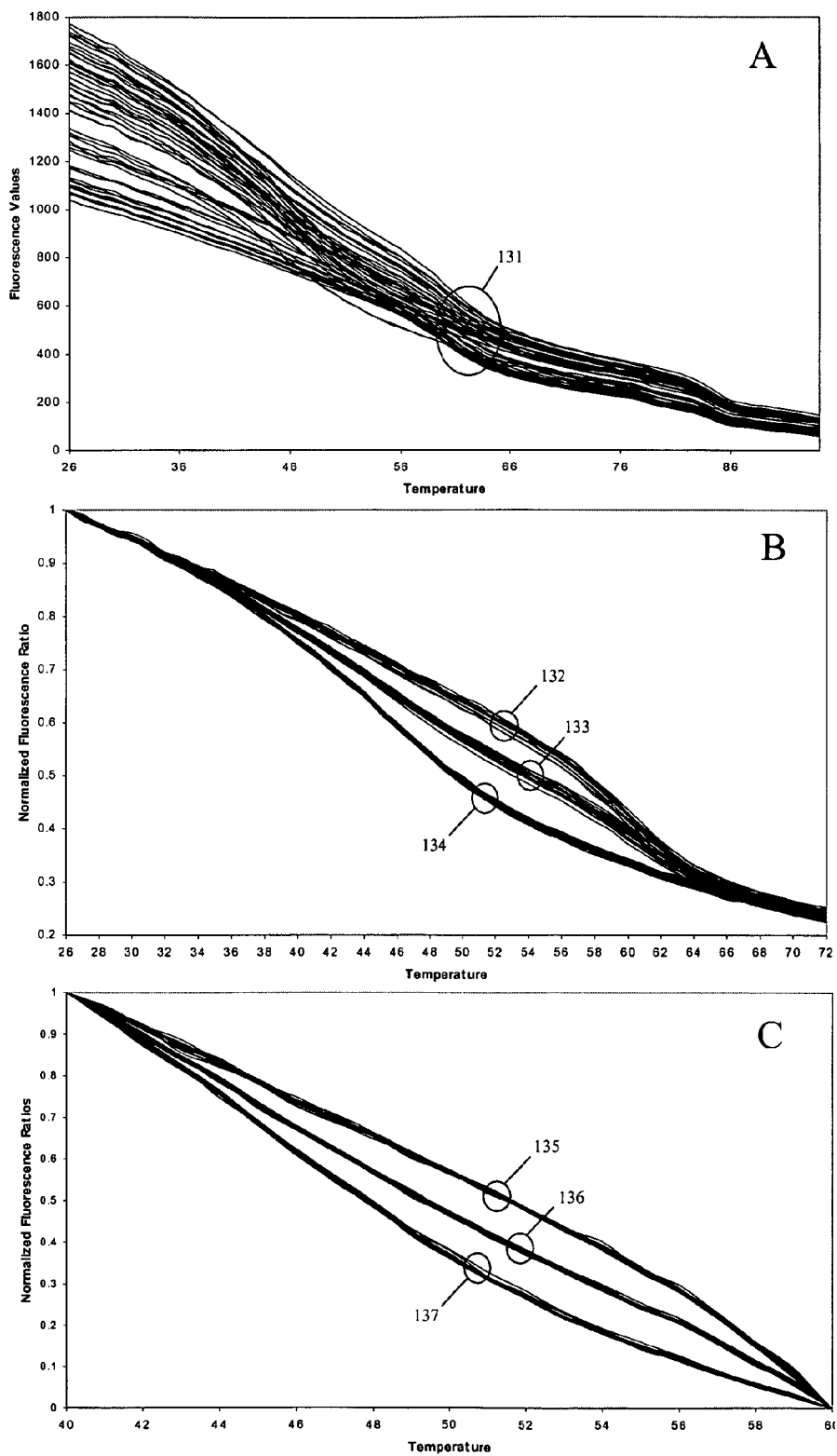
FIGS. 13A, 13B, and 13C show Three Temperature Normalization assays

Replicate LATE-PCR amplification reactions containing the rs858521 SNP primers and a single mismatch-tolerant resonsense probe were performed with purified genomic DNA for each genotype of the rs858521 gene SNP (1800 genomes equivalent, 18 replicate reactions of each homozygous CC, heterozygous CG, and homozygous GG genotypes). The amplified products were analyzed by melting curves, shown in FIG. 13, panel A and by normalizing the data, as shown in Panel B and panel C. FIG. 13A shows a plot of the raw fluorescence signals collected during melting curve analysis following LATE-PCR amplification. The probe that was utilized was allele-discriminating at higher temperatures but became progressively more mismatch tolerant as temperature was reduced. The intrinsic variability in product yield among replicate samples precludes discrimination of these genotypes by raw fluorescence signals (circle 131) within the temperature window of allele discrimination for this probe (40° C.-60° C., previously determined with synthetic oligonucleotide targets, data not shown). FIG. 13B shows the signals from each sample normalized at every temperature against the signal collected at a fully mismatch-tolerant temperature (25° C.) for that sample. In FIG. 13B the normalized signals for the homozygous CC alleles are circle 132, the normalized signals for the heterozygous CG alleles are circle 133, and the normalized signals for the homozygous GG alleles are circle 134. As the figure shows, normalization reduces signal scatter and allows identification of each genotype within the window of allele discrimination. Maximum separation was observed at 52° C., which corresponds to the Tm of the resonsense probe that was used. Although signal scatter was significantly reduced in FIG. 13B compared to FIG. 13A, there was still some variability in signal intensity among replicate samples judging from the spread in the kinetic plots. FIG. 13C shows that the best method to eliminate this residual signal scattering was by normalizing the fluorescent signals at each temperature to the fluorescent signals collected at top and bottom temperatures of the window of allele discrimination observed in FIG. 13B where melting curves start to diverge (that is, 40° C. and 60° C. respectively). In FIG. 13C the normalized signals for the homozygous CC alleles are circle 135, the normalized signals for the heterozygous CG alleles are circle 136, and the normalized signals for the homozygous GG alleles are circle 137. If Fb and Ft are the fluorescence readings towards the bottom and the top of the temperature window of allele discrimination, respectively, and Fs is the fluorescent reading at any given temperature during melt analysis, then the normalized fluorescent ratios are calculated as:

Three-Temperature Normalized Fluorescence Ratio= $(Fs-Ft)/(Fb-Ft)$

Simultaneous normalization of the fluorescent signals at each temperature to the fluorescent signals at 40° C. and 60° C. within any given sample further reduced fluorescent signal scatter and caused the replicate melting curves from each genotype to become very tight (see FIG. 13C). Fluorescent ratios calculated at a single temperature, namely, the $T_m$ of the probe (52° C.) normalized using the fluorescent signals towards the top and bottom temperatures of window of allele discrimination (i.e., at 60° C., 40° C.) uniquely define each genotype with greater than 99.7% certainty (i.e., error boxes consisting of three-standard deviations encompassing 99.7% of all possible fluorescent ratios for each genotype are well separated from each other, data not shown). Similarly improved results were obtained for the rs2270517 SNP site when fluorescent signals were calculated at the $T_m$ of the probe (57° C.) normalized to the corresponding top and bottom temperatures of window of allele discrimination (i.e., at 71° C., 45° C.).

Example 7. Direct Pyrosequencing of LATE-PCR Product

Figure 14A:
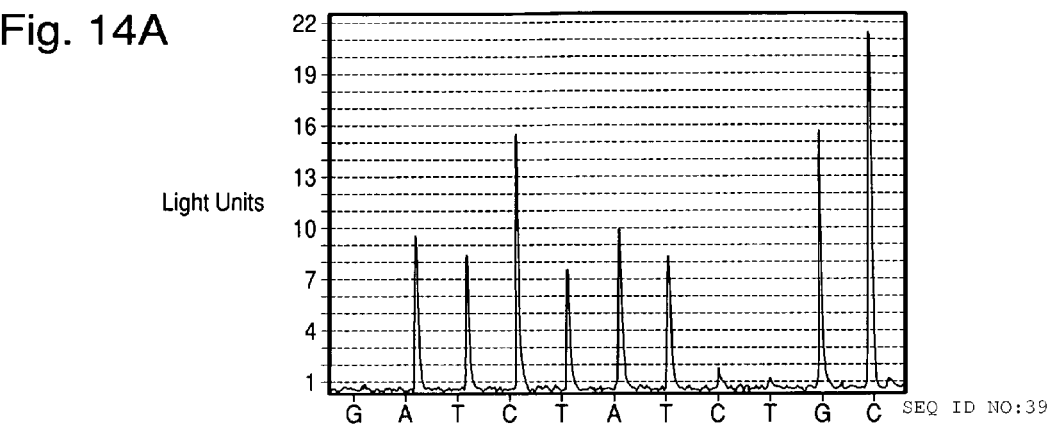
FIG. 14 shows pyrograms of the "dilute-and-go" method of preparation of LATE-PCR samples for pyrosequencing according the methods of the invention (A) relative to the conventional method of preparation of LATE-PCR samples (B) for the same assay, and (C) a comparison thereof.
Figure 14B:
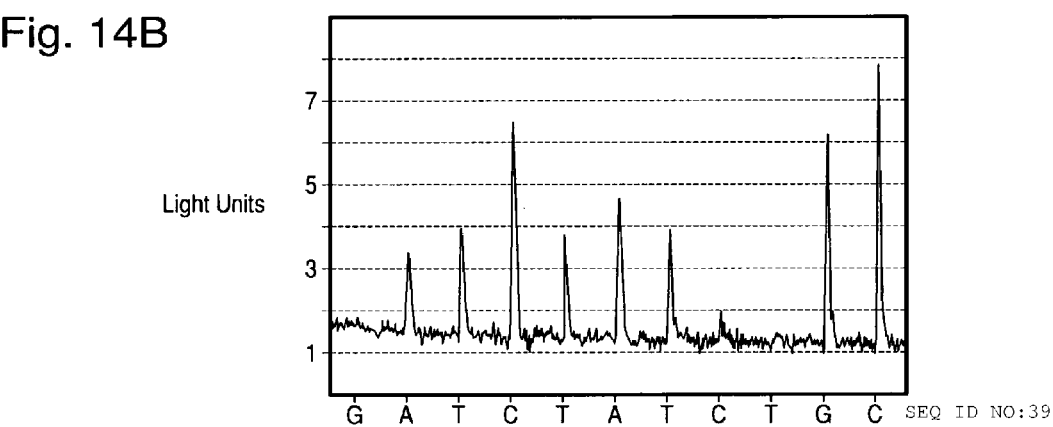
Figure 14C:
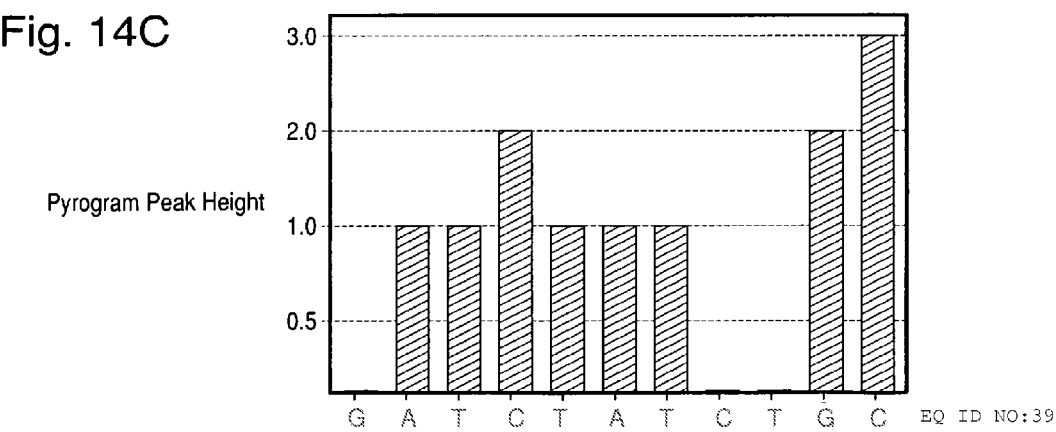

Replicate LATE-PCR amplifications were carried out in 25 Tl volume consisting of 1×PCR buffer, 3 mM $MgCl_2$, 20 nanomolar (nM) dNTP, 25 nM Limiting Primer, 1000 nM Excess Primer, 1.25 units Platinum Taq DNA polymerase, and 100 genomes human DNA. The sequence of the Limiting Primer was 5' CCGCCCTTCTCTCTGCCCCCTGGT 3' (SEQ. ID No. 6) and the sequence of the Excess Primer was 5' GCCAGGGGTTCCACTACGTAGA 3' (SEQ. ID No. 7). These sequences amplify a 94 base-pair segment from exon 11 of the human Hexosaminidase A gene. For LATE-PCR amplification, the thermal cycle profile was 95° C. for 3 min followed by 10 cycles of 95° C. for 10 sec, and 72° C. for 20 sec, followed by 55 cycles of 95° C. for 10 sec, 67° C. for 20 sec, and 72° C. for 20 sec. After the reaction 16.6 µl (the equivalent of 3 pmoles of single-stranded DNA (ssDNA) as estimated empirically from previous pyrosequencing experiments) were mixed with 20 microliter (µl) 10 mM Tris-Cl pH 8.5 and placed in a well of a microtiter plate used for pyrosequencing. For removal of carried-over dNTP and pyrophosphate from the LATE-PCR-amplified product, standard pyrosequencing enzyme mixture consisting of exonuclease-deficient Klenow DNA polymerase, apyrase, luciferase, ATP sulfurylase and standard pyrosequencing Substrate Mixture consisting of luciferin and adenosine 5' phosphosulfate as provided in the PSQ 96 SNP Reagent Kit (Pyrosequencing, Inc, Westboro, Mass.) were dispensed sequentially into the well containing the LATE-PCR sample using a PSQ 96 instrument (Pyrosequencing, Inc., Westboro, Mass.) according to the manufacturer's instructions and incubated for 60 sec at 37° C. The subsequent dNTP additions normally carried out automatically by the PSQ 96 instrument were replaced by a single addition of 10 mM Tris-Cl pH 7.5 using the default volume programmed in the instrument. Following this step, the well containing the LATE-PCR sample received 2.5 µl 10 µM sequencing primer (5' CTGGTACCTGAACCGTAT 3') (SEQ. ID No. 8). Taking into account the volume of pyrosequencing enzyme and substrate mixtures added to the LATE-PCR sample, the final concentration of sequencing primer was estimated to be 0.5 ™ and the final volume 50 µl. The sample with the sequencing primer was returned to the PSQ 96 instrument again and processed according to the manufacturer's instructions except that the pyrosequencing enzyme and substrate additions normally carried out by the instrument were replaced by addition of similar volumes of 10 mM Tris-Cl pH 7.5 followed by addition of dNTP. The resulting pyrogram is shown in FIG. 14, Panel A, which shows light signal resulting from incorporation of particular nucleotides. The height of the peaks corresponds to the number of nucleotides incorporated during each addition. Referring to Panel C of FIG. 14, one sees that one of each of the first two nucleotides (A, T) was incorporated into the template, followed by two of the next nucleotide (C, C), and so on. Based on the height of the peaks and the order of nucleotide additions a sequence was derived: 5' ATC-CTATGGCCC3' (SEQ. ID No. 9) and subsequently confirmed using the GenBank sequence for the human Hexosaminidase A gene (GenBank accession number: S62068). These results demonstrate pretreatment of LATE-PCR samples with the enzyme and substrates mixtures used for pyrosequencing permits direct pyrosequencing of LATE-PCR-amplified product following primer annealing and iterative dNTP addition. Altering the above protocol to follow the manufacturer's instructions (i.e., performing primer annealing followed by addition of the pyrosequencing enzyme and substrate mixtures) resulted in 80% false positive peaks upon addition of dNTP that were not supposed to be incorporated on the template. These false positive peaks were due to partial extension the sequencing primer from the leftover dNTP from LATE-PCR amplification prior to pyrosequencing.

In a separate experiment, the same LATE-PCR sample described above was subjected to purification using a QIAquick PCR purification kit (Qiagen, Valencia, Calif.) according to the manufacturer's instructions and recovered at 0.375 pmoles/µl in 10 mM Tris-Cl pH. 7.5. Eight microliters (µl)

of this solution (3 pmoles total) were mixed with the sequencing primer described above to a final concentration of sequencing primer of 0.5 µM in a final volume of 50 µl in 10 mM Tris-Cl pH. 7.5. The sample was subjected to pyrosequencing using the PSQ 96 instrument according to the manufacturer's instructions. The resulting pyrogram is shown in FIG. 14, panel B. Traditional preparation, while more time-consuming and expensive, did not give superior data as compared to our method that produced Panel A.

Example 8. Direct Pyrosequencing of LATE-PCR Products

Figure 15A:
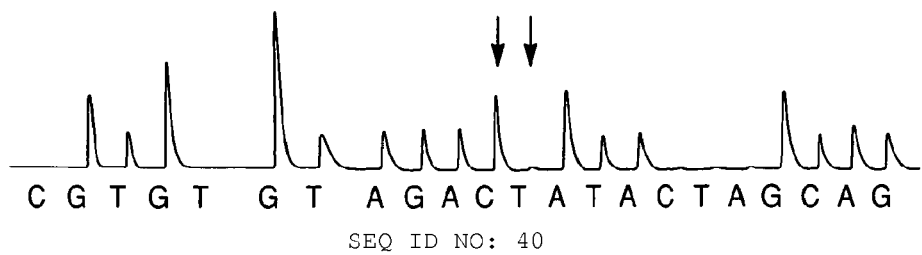
FIG. 15 is Pyrograms obtained from single cells prepared by the single-tube LATE-PCR method. Arrows indicate the β-globin IVS 110 site of: (A) homozygous wild-type, (B) heterozygous and (C) homozygous mutant cells.
Figure 15B:
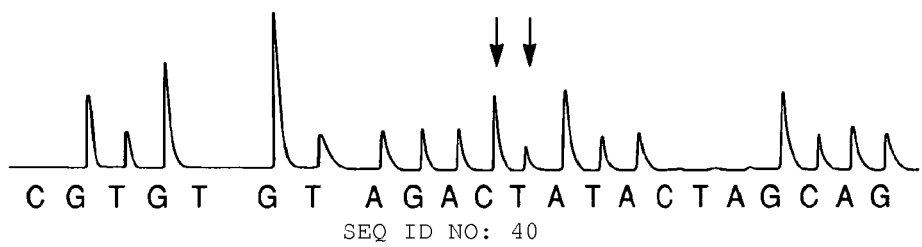
Figure 15C:
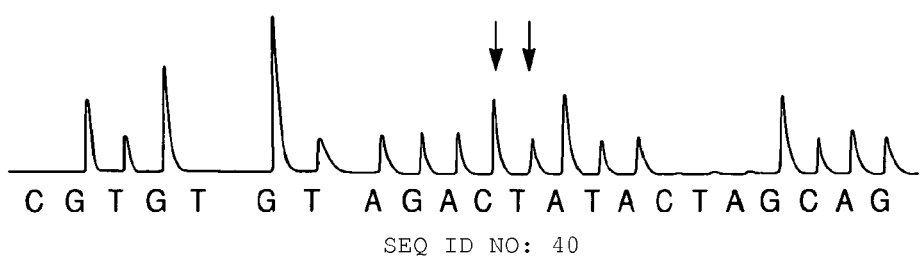

To genotype single cells, replicate LATE-PCR amplifications were carried out in a 25 µL, volume consisting of 1×PCR buffer, 3 mM $MgCl_2$, 100 µM dNTP, 100 nM Limiting Primer, 1000 nM Excess Primer, 1.25 units Ampli-Taq Gold DNA polymerase (Applied Biosystems, USA). Each reaction was initiated with a single human lymphoblast prepared as described in Pierce et al. (2002) Biotechniques 32(5): 1106-1111 (see United States patent publication US-2003-022231-A1) with one of the three possible genotypes for the IVS-110 mutation. The sequence of the Limiting Primer was 5' GGCCATCACTAAAGGCACCGAG-CACT 3' (SEQ. ID NO. 10) and the sequence of the Excess Primer was 5' GGGTTTCTGATACGCACTGACTCTCTC 3' (SEQ. ID NO. 11). These sequences amplify a 191 base-pair segment from the β-Globin gene on human chromosome 11p. For LATE-PCR amplification, the thermal cycle profile was 95° C. for 10 min followed by 65 cycles of 95° C. for 10 sec, 66° C. for 15 sec and 72° C. for 20 sec. After amplification, 5 µl were mixed with 6.64 µl 20 mM Tris-Acetate pH 7.6 and placed in a well of an optical plate used for Pyrosequencing. For removal of carried-over dNTPs and PPi from the product of LATE-PCR amplification a standard volume of Pyrosequencing enzyme mixture (consisting of exonuclease-deficient Klenow DNA polymerase, apyrase, luciferase, ATP sulfurylase) and approximately twice the standard volume of substrate mixture (consisting of luciferin and adenosine 5' phosphosulfate) as provided in the Pyro Gold Reagent Kit (Biotage AB, Uppsala, Sweden) were dispensed sequentially into the wells containing the LATE-PCR samples using a PSQ HS 96A instrument (Biotage AB, Uppsala, Sweden) using the following instrument settings: enzyme mix pulse time: 23.5 ms; substrate mix pulse time: 44.0 ms; reagent dispensation pressure: 400 mbar. Samples were incubated for 60 sec at 28° C. until light output dropped below background. Following this, 0.36 µL of a 10 µM sequencing primer: 5' GACCACCAGCAGCCTAAG 3' (SEQ. ID NO. 12) was added to each sample for a total reaction volume of 120 and then annealed at 80° C. for 2 min followed by cooling to room temperature for 10 min. In addition, a 900 µM concentration of a 3' phosphorylated version of the LATE-PCR Limiting Primer (SEQ. ID NO. 7) was also added here to prevent the 3' end of the template strand from folding over on itself and extending. Samples with the sequencing primer were then returned to the PSQ HS 96A instrument again and processed according to the manufacturer's instructions, including normal enzyme and substrate mix additions. The resulting Pyrograms from cells with a homozygous wild-type, heterozygous and homozygous mutant genotypes are shown in FIG. 15, Panels A-C, respectively. Light units and peak heights are as explained in Example 7. The relative height of the peaks corresponds to the number of nucleotides incorporated at each position. Referring to panel A of FIG. 15, one sees that the second peak (T) is half as tall as the first peak (G), one third as tall as the third peak (G), one forth as tall as the fourth peak (A) and the same height as peaks 5-8 (TAGA). The sequence for the first eight peaks is thus read as: GGTGGGAAAATAGA (SEQ. ID No. 13). Based on the height of the peaks and the order of nucleotide additions, the wild-type β-Globin sequence in FIG. 15, panel A was derived and subsequently confirmed using the GenBank sequence for the human β-Globin Gene. A heterozygous (Panel B) or homozygous (Panel C) mutation was confirmed at the IVS-110 site, indicated by arrows. It is of note in Panel B that the 1.5 unit "C" peak followed by a 0.5 unit "T" peak indicates a "C" base in both alleles followed by a "C" in one allele and a "T" in the other allele. These results demonstrate that pretreatment of LATE-PCR samples with the enzyme and substrates mixtures used for Pyrosequencing permits direct Pyrosequencing of LATE-PCR following primer annealing and iterative dNTP additions. Altering the above protocol to follow the manufacturer's instructions (i.e., performing primer annealing followed by addition of the Pyrosequencing enzyme and substrate mixtures) resulted in 80% false positive peaks upon addition of dNTP that were not supposed to be incorporated on the template. These false positive peaks were due to partial extension of the sequencing primer with leftover dNTPs.

Example 9. Pyrosequencing of LATE-PCR Products for Long Sequences

Figure 16:
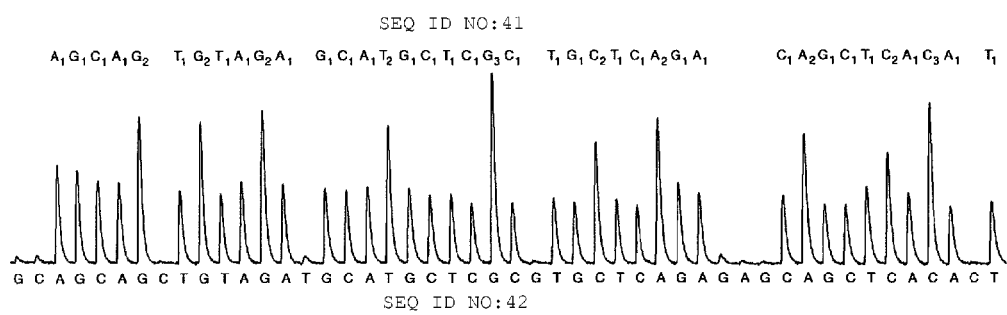
FIG. 16 is the Pyrogram from a Pyrosequencing reaction carried out for more than fifty base pairs. Nucleotide dispensation order is listed below each peak and the expected sequence is noted above.
Figure 17A:
FIG. 17 is dideoxy sequencing chromatographs resulting from the "dilute-and-go" method of preparation of LATE-PCR samples for dideoxy sequencing according the methods of the invention and from the conventional method of preparation of LATE-PCR samples for the same assay for (A) SEQ ID NO: 43, (B) SEQ ID NO: 44, (C) SEQ ID NO: 45, and (D) SEQ ID NO: 46.
Figure 17B:
Figure 17C:
Figure 17D:

A LATE-PCR amplification was carried out in a 25 µl volume consisting of 1×PCR buffer, 3 mM $MgCl_2$, 100 µM dNTP, 100 nM Limiting Primer, 1000 nM Excess Primer, 1.25 units AmpliTaq Gold DNA polymerase (Applied Biosystems, USA) and 50 nM of mispriming-reducing reagent 9-22DD as disclosed in our filed United States Provisional patent application, titled "Reagents and Methods for Improving Reproducibility and Reducing Mispriming in PCR Amplification". Reagent 9-22DD is a hairpin oligonucleotide having a stem nine nucleotides long and a single-stranded loop 22 nucleotides long. The oligonucleotide is modified by the addition of 5' terminal and 3' terminal Dabcyl moieties. Its nucleotide sequence is 5' CGCG-GCGTCAGGCATATAGGATACCGGGACAGACGC-CGCG 3' (SEQ. ID. No 14). The reaction was initiated with 20 genome equivalents of human DNA. The sequence of the Limiting Primer was 5' GGTCAGCGCCGGGCTGCAAGT-GTAGA 3' (SEQ. ID NO. 15) and the sequence of the Excess Primer was 5' GATGGGTGGAGCTTGTCTTGAGG 3' (SEQ. ID NO. 16). These sequences amplify a 78 base-pair segment near the p53 gene on human chromosome 17p. For LATE-PCR amplification, the thermal cycle profile was 95° C. for 10 min followed by 60 cycles of 95° C. for 10 sec, 66° C. for 10 sec and 72° C. for 20 sec. After amplification, 7.5 µl of product was mixed with 9.96 µl 20 mM Tris-Acetate pH 7.6 and placed in a well of an optical plate used for Pyrosequencing. For removal of carried-over dNTPs and PPi from LATE-PCR a standard volume of Pyrosequencing enzyme mixture (consisting of exonuclease-deficient Klenow DNA polymerase, apyrase, luciferase, ATP sulfurylase) and approximately twice the standard volume of substrate mixture (consisting of luciferin and adenosine 5' phosphosulfate) as provided in the Pyro Gold Reagent Kit (Biotage AB, Uppsala, Sweden) was dispensed sequentially into the well containing the LATE-PCR samples using a PSQ HS 96A instrument (Biotage AB, Uppsala, Sweden) using the following instrument settings: enzyme mix pulse time: 23.5 ms; substrate mix pulse time: 44.0 ms; reagent dispensation pressure: 400 mbar. The sample was then incubated for 60 sec at 28° C. until light output dropped below background. In this amplicon, the Limiting LATE-PCR primer (SEQ. ID NO. 10) was used as the Pyrosequencing primer and 0.54 μl of 10 μM solution of this was added to each sample for a total reaction volume of 18 μl and then annealed at 80° C. for 2 min followed by cooling to room temperature for 10 min. Samples with the sequencing primer were then returned to the PSQ HS 96A instrument again and processed according to the manufacturer's instructions, including normal enzyme and substrate mix additions. The resulting Pyrogram is shown in FIG. 16. The relative height of the peaks corresponds to the number of nucleotides incorporated at each position as described in Example 8. The correctly matching expected sequence, as determined from the GenBank database, is noted above the peaks with subscripts indicating the number a given base in a row (i.e. $G_1C_1A_1G_2$=GCAGG). These results demonstrate that pretreatment of LATE-PCR samples with the enzyme and substrates mixtures used for Pyrosequencing allows for reads more than fifty base pairs long.

Example 10. Direct Dideoxy Sequencing of LATE-PCR Product

PCR amplifications were performed utilizing an ABI Prism Sequence Detector 7700 (Applied Biosystems, Foster City, Calif., U.S.A.) to amplify a segment of exon 7 of the human Hexosaminidase A gene containing the G269 mutation, which is responsible for Tay-Sachs Disease. The sequence corresponds to GenBank accession number M16417. One amplification was a LATE-PCR amplification, and the product was subjected directly to dideoxy sequencing. As a control the primer concentrations were changed to equimolar, a conventional symmetric PCR amplification was performed, and amplified product was subjected to conventional purification prior to dideoxy sequencing.
Amplification Reaction Mixtures (Final Concentrations)
    Volume: 25 μl
    1×PCR buffer (Invitrogen, Carlsbad, Calif., U.S.A.)
    3 mM $MgCl_2$
    10 μM dNTPs
    0.6 μM Probe (LATE-PCR only)
    1:41,666 dilution SYBR Gold Dye (Molecular Probes, Eugene, Oreg., U.S.A)
    1.25 Units Platinum Taq DNA polymerase (Invitrogen)
    6 ng human genomic DNA (equivalent to 1000 genomes)
    Primers: for LATE-PCR, 25 nM Limiting Primer and 1000 nM Excess Primer; (for the control, 300 nM of each of the same primers).
Oligonucleotide Sequences

```
Limiting Primer:
                                      (SEQ. ID. No. 17)
5' CGAGGTCATTGAATACGCACGGCTCC 3'

Excess Primer:
                                      (SEQ. ID. No. 18)
5' TAACAAGCAGAGTCCCTCTGGT 3'

Probe:
                                      (SEQ. ID No. 19)
5' Cy5 GGGACCAGGTAAGAA- Phosphate 3'
```

Cycle Sequencing Reaction Mixture
    Volume: 20 μl
    100 femtomoles (fmoles) product being sequenced
    5 picomoles (pmoles) Sequencing Primer (either the Limiting Primer or the Excess Primer)
    1×DTC5 Quick Start Master Mix (Beckman Coulter, Inc., Fullerton, Calif., U.S.A.)
    [includes dNTPs, ddNTP, buffer, $MgCl_2$].
Dideoxy Sequencing
    Sequencing reaction mixtures were subjected to cycle sequencing and capillary electrophoresis in a CEQ 2000XL DNA Sequence (Beckman Coulter, Inc., Fullerton, Calif., U.S.A.) using the CEQ 2000 Due Termination Cycle Sequencing Kit (Beckman Coulter) according to the manufacturer's instructions.
LATE-PCR Amplification and Sequencing Preparation
    The LATE-PCR amplification reaction mixture was subjected to thermal cycling as follows: 95° C. for 3 min; 20 cycles of 95° C. for 10 sec, 65° C. for 20 sec and 72° C. for 20 sec, and 70 cycles of 95° C. for 10 sec, 65° C. for 20 sec, 72° C. for 20 sec, 55° C. for 20 sec and 40° C. for 20 sec. Synthesis of double-stranded amplicon was monitored by exciting the SYBR dye and reading its fluorescence during the 72° C. primer-extension step. Synthesis of single-stranded product following exhaustion of the Limiting Primer was monitored by exciting the SYBR dye and reading fluorescence from the low-$T_m$ Probe's Cy5 fluorophore during the 40° C. low-temperature detection step.
    To obtain 100 fmoles of the extension product of the Excess Primer, dilution of the amplification product was necessary. We estimated the amount of product in the 25 ul of reaction product in the following manner. First, the amount of that product in double-stranded product made during the initial amplification cycles is dictated by the amount of Limiting Primer. In this example that was 25 nM, which translates to 25 fmoles/μl. The concentration of single-stranded extension product made during the linear phase of LATE-PCR amplification, that is, after exhaustion of the Limiting Primer, was estimated by dividing that phase into two parts determined by inspection of the Cy5 fluorescence curve: a first part in which amplification proceeds arithmetically, and a second part in which product accumulation has slowed. For the first part, which in this example was six cycles, we assumed an amplification efficiency of 50%, based on Gyllensten, U. B. H. and Erlich, A. (1988), "Generation of Single-Stranded DNA by the Polymerase Chain Reaction and its Application to Direct Sequencing of the HLA-DQA LOCUS," Proc. Natl. Acad. Sci. USA 85: 7652-7656. Production of single strands during the six cycles was calculated as the starting concentration (25 fmoles/μl) times the number of cycles (6) times the efficiency (0.5). Further production was estimated as the percentage increase in Cy5 signal during the remainder of the reaction, which in this case was 233.3%. Total production during the linear phase was thus 175 fmoles/μl (25×6×0.5× 2.333), and the total concentration of that product, including 25 fmoles/μl in double-stranded amplicon, was estimated to be 200 fmoles/μl. To obtain 100 fmoles in the cycle-sequencing reaction mixture, we diluted the amplification product 1:8 with water and used 4 μl of the diluted product in the 20 μl reaction mixture. As will be appreciated, this meant that the amplification product was ultimately diluted 1:40.
    To obtain 100 fmoles of the extension product of the Limiting Primer, our starting point was that the product of the amplification reaction contained 25 nM of that product, or 25 fmoles/μl. We simply used 4 μl of the amplification product in the 20 μl cycle-sequencing reaction mixture to obtain the desired starting amount of 100 fmoles.
Control Amplification and Sequencing Preparation.
    The amplification reaction mixture was subjected to the same thermal cycling profile, except that only 18 (rather than 70) of the five-temperature cycles were carried out, because a real-time plot of the intercalating dye signal indicated that the amplification plateaued at this point and only desired amplification product was made to that point. The amplification products in the amplification mixture at the end of amplification were purified in conventional manner using QUIA quick PCR purification kit (Qiagen, Valencia, Calif., U.S.A.) according to the manufacturer's instructions. Purified amplicons were quantified by gel electrophoresis in a 3% agarose gel in 0.5×TBE against different known amounts of ΦX174 Hind III DNA markers following visualization by ethidium bromide staining (0.5 Tg/ml). A volume containing 100 fmoles was used in the cycle-sequencing reaction mixture with each sequencing primer.

Results

The LATE-PCR and control methods both produced sequences corresponding to Genbank sequence information (accession number M 16417). FIG. 17 includes four chromatographs obtained from dideoxy sequencing. Panel A is from the LATE-PCR method with cycle sequencing utilizing the Limiting Primer as the sequencing primer. Panel B is from the LATE-PCR method with cycle sequencing utilizing the Excess Primer as the sequencing primer. Panel C is the control method utilizing the Excess Primer as the sequencing primer. Panel D is the control method utilizing the Limiting Primer as the sequencing primer. Each chromatograph includes the fluorescence curves obtained from the labeled dideoxy nucleotides and the nucleotide sequence determined.

Example 11. Strategies for LATE-PCR Amplification of More than One Product from the Same DNA Template in the Same Reaction PCR amplifications were performed utilizing an ABI Prism Sequence Detector 7700 (Applied Biosystems, Foster City, Calif., U.S.A.) to amplify two amplicons of 549 and 464 bases designated as HV1 and HV2 H and L strands in the same duplex reaction within the d-loop region of Human mitochondrial DNA based on which sequences were amplified using an Excess Primer.

Amplification Reaction Mixtures (Final Concentrations)
Volume: 25 Tl
1×PCR buffer (Invitrogen, Carlsbad, Calif., U.S.A.)
3 mM MgCl2 (Invitrogen)
250 µM dNTPs (Promega)
1.0 µM Probe (LATE-PCR only)
10× dilution SYBR Green Dye (FMC Bioproducts, Rockland Me., U.S.A)
1.25 Units Platinum Taq DNA polymerase (Invitrogen)
Human blood lymphocyte genomic DNA (equivalent to 100 mtDNA genomes)
Primers: for LATE-PCR, 50 nM Limiting Primer and 1000 nM Excess Primer.

Oligonucleotide Sequences

Probe:
(SEQ. ID No. 20)
5' Cy5- TGCTAATGGTGGAG -Phosphate 3'

HV1-H
Limiting Primer:
(SEQ. ID. No. 21)
5' GCCCGGAGCGAGGAGAGTAGCACTCTTG 3'

Excess Primer:
(SEQ. ID. No. 22)
5' CACCAGTCTTGTAAACCGGAGATGAA 3'

HV2-H
Limiting Primer:
(SEQ. ID. No. 23)
5' GTATGGGAGTGGGAGGGGAAAATAATGTGTTAG 3'

Excess Primer:
(SEQ. ID. No. 24)
5' AGGTCTATCACCCTATTAACCACTCA3'

HV1-L
Limiting Primer:
(SEQ. ID. No. 25)
5' CACCAGTCTTGTAAACCGGAGATGAAAACC 3'

Excess Primer:
(SEQ. ID. No. 26)
5' CGAGGAGAGTAGCACTCTT3'

HV2-L
Limiting Primer:
(SEQ. ID. No. 27)
5' AGGTCTATCACCCTATTAACCACTCACGGG 3'

Excess Primer:
(SEQ. ID. No. 28)
5' GGAGGGGAAAATAATGTGTTAGT 3'

Cycle Sequencing Reaction Mixture
Volume: 25 µl
100 fmoles product being sequenced
5 pmoles Sequencing Primer (either the Limiting Primer or the Excess Primer)
1×DTC5 Quick Start Master Mix (Beckman Coulter, Inc., Fullerton, Calif., U.S.A.) [includes dNTPs, ddNTP, buffer, MgCl2].

Dideoxy Sequencing

Sequencing reaction mixtures were subjected to cycle sequencing and capillary electrophoresis in a CEQ 2000XL DNA Sequence (Beckman Coulter, Inc., Fullerton, Calif., U.S.A.) using the CEQ 2000 Dye Termination Cycle Sequencing Kit (Beckman Coulter) according to the manufacturer's instructions.

LATE-PCR Amplification and Sequencing Preparation

The LATE-PCR amplification reaction mixture was subjected to thermal cycling as follows: 95° C. for 3 min; 15 cycles of 95° C. for 15 sec, 64° C. for 10 sec and 72° C. for 45 sec, and 50 cycles of 95° C. for 15 sec, 64° C. for 10 sec, 72° C. for 45 sec, and for HV1-H only 50° C. for 20 sec. Synthesis of double-stranded amplicon was monitored by exciting the SYBR Green dye and reading its fluorescence during the 72° C. primer-extension step. Synthesis of single-stranded product following exhaustion of the Limiting Primer was monitored by exciting the SYBR dye and reading fluorescence from the low-Tm Probe's Cy5 fluorophore during the 50° C. low-temperature detection step for HV1-H region only.

To obtain 100 fmoles of the extension product of the Excess Primer, dilution of the amplification product was necessary. We estimated the amount of product in the 25 µl of reaction product in the following manner. First, the amount of that product in double-stranded product made during the initial amplification cycles is dictated by the amount of Limiting Primer. In this example that was 50 nM, which translates to 50 fmoles/µl. The concentration of single-stranded extension product made during the linear phase of LATE-PCR amplification, that is, after exhaustion of the Limiting Primer, was estimated by dividing that phase into two parts determined by inspection of the Cy5 fluorescence curve: a first part in which amplification proceeds arithmetically, and a second part in which product accumulation has slowed. For the first part, which in this example was eleven cycles, we assumed an amplification efficiency of 50%, based on Gyllensten, U. B. H. and Erlich, A. (1988), "Generation of Single-Stranded DNA by the Polymerase Chain Reaction and its Application to Direct Sequencing of the HLA-DQA LOCUS," Proc. Natl. Acad. Sci. USA 85: 7652-7656. Production of single strands during the eleven cycles was calculated as the starting concentration (50 fmoles/µl) times the number of cycles 11) times the efficiency (0.5). Further production was estimated as the percentage increase in Cy5 signal during the remainder of the reaction, which in this case was 100%. Total production during the linear phase was thus 275 fmoles/µl (50×11×0.5×1.0), and the total concentration of that product, including 50 fmoles/µl in double-stranded amplicon, was estimated to be 325 fmoles/µl. To obtain 100 fmoles in the cycle-sequencing reaction mixture, we diluted the amplification product 1:13 with water and used 4 µl of the diluted product in the 25 µl reaction mixture.

Results

There are four possible combinations are: 1) HV1-H with HV2-H, 2) HV1-L with HV2-L, 3) HV1-H with HV2-L, 4) HV1-L with HV2-H. FIG. 18 shows a 4% agarose gel from electrophoresis of no-template controls (NTC), left three lanes; amplicons from reactions begun with 100 copies of genomic DNA, next three lanes; and in the far right lane a 100 base-pair ladder. FIG. 18 shows the formation of the HV1-H and HV2-H dsDNA amplicons of 549 and 464 base pairs using 100 copies of genomic DNA at the start of the reaction. No template controls, NTC, did not amplify.

As one versed in the art will understand, in amplifying two single-stranded amplicons in the same reaction from a single template, the two excess primer strands can be generated from the same strand of DNA or from complementary strands of DNA. We have successfully employed both approaches. In the combinations HV1-H with HV2-H and HV1-L with HV2-L both amplicons are generated from the same DNA template strand. In the combinations HV1-H with HV2-L and HV1-L with HV2-H the two amplicons are generated from complementary strands of DNA. FIG. 19 A displays sequence information for amplicon HV1-H in the duplex HV1-H with HV2-H in the region of bases 16209-16169. FIG. 19 B displays sequence information for the amplicon HV2-H in the duplex HV1-H with HV2-H in the region bases 289-326. FIG. 19 C displays sequence information for the HV1-H amplicon in the duplex HV1-H with HV2-L in the region bases 16209-16169. FIG. 19 D displays sequence information for the HV2-L amplicon in the duplex HV1-H with HV2-L in the region bases 289-326. The LATE-PCR produced sequences corresponding to GenBank sequence information.

Example 12. Determining ssDNA Need

The amount of single stranded DNA and double stranded DNA generated by a LATE-PCR amplification can be used to determine amount of ssDNA needed for "dilute-and-go" Dideoxy Sequencing. PCR amplifications were performed utilizing an ABI Prism Sequence Detector 7700 (Applied Biosystems, Foster City, Calif., U.S.A.) to amplify the 549 base amplicon designated as HV1 H within the d-loop region of human mitochondrial DNA. MtDNA was extracted under lysis conditions (as described in Peirce et al. (2002) Biotechniques 32(5); 1106-1111 with the inclusion of 4 ul DTT in 100 ul of the lysis reaction mixture) from a human hair shaft. All amplifications were LATE-PCR amplifications, and the product was subjected directly to dideoxy sequencing.

Amplification Reaction Mixtures (Final Concentrations)
 Volume: 25 µl
 1×PCR buffer (Invitrogen, Carlsbad, Calif., U.S.A.)
 3 mM MgCl2 (Invitrogen)
 250 µM dNTPs (Promega)
 1.0 µM Probe (LATE-PCR only)
 10× dilution SYBR Green Dye (FMC Bioproducts, Rockland Me., U.S.A)
 1.25 Units Platinum Taq DNA polymerase (Invitrogen)
 1 µl DNA Lysis solution (equivalent to ~10 mtDNA genomes)
 Primers: for LATE-PCR, 50 nM Limiting Primer and 1000 nM Excess Primer.

Oligonucleotide Sequences
 HV1H: Limiting Primer, Excess Primer and Probe as in Example 11.

Cycle Sequencing Reaction Mixture
 As in Example 11.

Dideoxy Sequencing
 As in Example 11.

LATE-PCR Amplification and Sequencing Preparation
 As in Example 11. The raw fluorescent data of the both CY5 and SYBR Green were used to determine the amount of product available for a sequencing reaction. The CY5/SYBR Green ratio was used to normalize all fluctuations in the raw data.

Results

Fluorescence data from the LATE-PCR amplifications is presented in FIG. 20, panels A and B. FIG. 20A, e.g., line 201 shows all of the hair shaft data plotted against amplification cycle numbers as the ratio ss-DNA/ds-DNA (probe signal to dye signal). This method of analysis minimizes the variation due to when exponential amplification begins, or at what level it plateaus, and demonstrates that the efficiency of ss-DNA amplification is virtually the same in all samples except the one that began very late. FIG. 20B shows a method for monitoring a set of LATE-PCR assay in order to establish their readiness for dilute-and-go sequencing. The plot shows the calculated ratios ssDNA/dsDNA (probe signal to dye signal versus dye signal) for all amplified samples at cycle 45 (squares) and cycle 65 (diamonds). Only the samples that have ratios of between 0.06 and 0.10 and SYBR values between 300 and 600 (those in the box) are ready for sequencing. FIG. 20B extends the use of Quantitative Endpoint analysis (QE LATE-PCR) to demonstrate that after 65 cycles all but one sample had accumulated sufficient ss-DNA for use in "dilute-and-go" sequencing.

Example 13. Amplicons Having Multiple SNPs

The sensitivity of the LATE-PCR and "dilute-and-go" sequencing method can distinguish a mixture of amplicons having multiple SNPs to the 10% resolution level. PCR amplifications were from a 2 mm human hair shaft or a single human thumbprint adhered to a glass slide. All amplifications were LATE-PCR amplifications, and the product was subjected directly to dideoxy sequencing. Final amplification reaction mixtures, Oligonucleotide Sequences (HV1-H), Cycle Sequencing Reaction Mixture, and Dideoxy Sequencing, and LATE-PCR Amplification and Sequencing Preparation were all as in Example 11.

Mixtures from 10:90 to 90:10 of the single-stranded LATE-PCR products of each of the three reactions were sequenced using the 'dilute-and-go" dideoxy protocol described previously. The results are shown in FIG. 21 and FIG. 22.

FIG. 21 show a 10 base segment surrounding bases 16320 and 16311 of the 50:50 mixture of Human blood lymphocyte and the Human thumbprint. The peak heights reflect the actual 100% heights in the dideoxy sequence and not the expected equal heights of a 50:50 mixture. Line 211 shows the peak for the G base at this sequence and line 202 shows the peak for the A base at the same position in the sequence. Peak 212 is higher than peak 211 in a 50:50 mixture of human blood lymphocyte and human hair shaft having different genetic sequences, because of the fluormetric characteristics of dideoxy sequencing as is demonstrable by analysis of pure sequences for the same region.

FIG. 22 shows the reciprocal percentages (90:10, 70:30, 50:50, 30:70 and 10:90) of two samples at each of five SNPs locations. Sample 1 came from a Human Hair Shaft and Sample 2 came from a Human Thumbprint from another individual. The heights of each peak at each position were measured from the printouts of the dideoxy sequences and were then scaled based on the same base of a 100% Sample 1 or 100% Sample 2 control. In FIG. 22, line 222 is the intended percentage of Sample 1 in the mixture plotted against the intended percentage of Sample 2 in the mixture. Line 221 is a line fitted to the actual results, that is, the observed percentage of Sample 1 in the mixture plotted against the intended percentage of Sample 2. The observed percentage for each intended percentage of Sample 2 is five points, one for each base. The data demonstrate that there is very little scatter among the different bases at each percentage, but the data also show that line 221 of the observed values does not fall on top of the line of the predicted values (line 222), probably because amount of Sample 1 and Sample 2 in the mixture were not exactly equal.

Example 14. Distinction of Mixtures

To distinguish samples consisting of 100% heterozygous genomic DNA from samples consisting of 90% heterozygous DNA and 10% homozygous genomic DNA for a single nucleotide change, we first created a DNA mixture consisting of 90% heterozygous DNA for the SNP site rs858521 located in human chromosome 17 (C/G alleles) plus 10% homozygous DNA for the same SNP site (C/C alleles). The SNP site is listed in the NCBI dbSNP database accessible through ncbi.nlm.nih.gov/entrez/query.fcgi?DB=SNP. This DNA mixture was prepared by mixing matched concentrations of the corresponding heterozygous and homozygous DNAs provided by the Reid Laboratory at the University of Washington in Seattle. DNA concentrations for each genomic DNA for mixing purposes were estimated based on the Ct values of SYBR fluorescence derived from real-time analysis of LATE-PCR samples similar to the one described below. Once the DNA mixture was prepared, we set up replicate LATE-PCR reactions containing either 100% heterozygous DNA or 90% heterozygous+10% homozygous DNA. Each LATE-PCR sample consisted of 1× Platinum Taq Buffer (Invitrogen, Carlsbad, Calif.), 3 mM $MgCl_2$, 250 μM dNTP mix, 0.24× SyberGold I (Invitrogen, Carlsbad, Calif.), 200 nM mispriming prevention reagent that we call Elixir compound 9-3iDD, 1.25 units Platinum Taq polymerase (Invitrogen, Carlsbad, Calif.), 1 μM rs858521 Excess Primer, 50 nM rs858521 Limiting primer, and 2.4 TM resonsense probe against the rs858521 SNP G allele, and 1800 genome equivalent of the appropriate genomic DNA in a final volume of 25 μl. The sequence of the rs858521 Excess Primer is (SEQ. ID. No. 29)
5' CAATCCCTTGACCTGTTGTGGAGAGAA 3'

The sequence of the rs858521 limiting primer is (SEQ. ID. No. 30)
5' TCCCCAGAGCCCAGCCGGTGTCATTTTC 3'

The sequence of the resonsense probe against the rs858521 SNP G allele is (SEQ. ID. No. 31)
5' [Cy5] CTTCAGCTCAAA<u>C</u>AATA [Phos]

The sequence of the mispriming prevention reagent is 5' Dabcyl (SEQ. ID. No. 32)
5' Dabcyl-CGCTATAATGAAATTATAGCG-Dabcyl These samples were subjected to amplification in an ABI 7700 using a thermal cycle profile consisting of one cycle of 95° C. for 3 min, followed by 45 cycles of 95° C. for 10 sec., 66° C. for 10 sec. and 72° C. for 20 sec. At the end of the reaction the reaction was melted from 95° C. to 25° C. at 1° C. intervals for 1 min. at each temperature with fluorescence acquisition in the Cy5 channel. The clipped Cy5 fluorescence signals with no baseline correction were exported into the Excel computer program. Calculation of the first derivative of the fluorescence signals was performed by subtracting the fluorescence signals from one temperature from the fluorescence signals of the next temperature during the melt. Results are shown in FIG. 23, panels A and B. FIG. 23A shows the plot of the first derivative of fluorescence signals versus temperature, that is, melting curves. The melting curves in FIG. 23A were smoothed using the moving average function of Excel to eliminate the noise due to thermal fluctuations in the ABI 7700. FIG. 23A revealed the melting peaks corresponding to the binding of the probe to its matched G allele target at higher temperatures and to the mismatched C allele target at lower temperatures. FIG. 23A shows that the 90% heterozygous+10% homozygous samples, circle 231, exhibit a lower G allele peak and a higher C allele melting peak relative to the heights of the C allele and the G allele melting peaks in the 100% heterozygous samples, circle 232. These differences are in accord with the expected higher proportion of the C allele in the 90% heterozygous+10% homozygous sample (55% C allele: 45% G allele) compared to the 100% heterozygous sample (50% G allele: 50% C allele). The ratio of the height of the C allele peak to the height of the G allele peak is shown as a bar graph in FIG. 23B. The set of bars on the right are for the 90% heterozygous+10% homozygous samples, corresponding to circle 231. The darker bars on the left are for the 100% heterozygous samples. Conventional error boxes 233 and 234 are shown for bar sets, respectively. This ratio distinguishes 100% heterozygous samples from 90% heterozygous+10% homozygous samples with 99.7% certainty based on the lack of overlap of the error boxes reflecting three standard deviations of the error of the mean.

Example 15. Sensitivity of LATE-PCR Reactions to the Initial Polymerase Concentration PCR amplifications were performed utilizing an ABI 7700 to amplify the 549 base amplicon designated as HVI-H within the d-loop region of human mitochondrial DNA. Reaction Mixtures for genomic human DNA, Oligonucleotide Sequences (HV1-H), and LATE-PCR amplifications were as described in Example 11, except the Units of Platinum Taq DNA polymerase varied among samples, as follows: 0.125, 0.250, 0.375, 0.50, 0.625, and 1.25 Units.

Melt curve analysis (SYBR green fluorescence versus temperature) were performed. Melt curves showed how the concentration of Taq influenced the specificity of dsDNA product for this LATE-PCR reaction. As Platinum Taq, concentration decreased from 1.25 units to 0.375 units the specificity of the reaction increased, as reflected in the melting peaks of replicates. Lowering the concentration further, to 0.250 units, decreased specificity. At 0.125 units the reaction did not occur. The greatest specificity occurred with a Taq concentration of 0.375 units.

Example 16. Slope Variation as a Function of Taq Concentration in a Real-Time LATE-PCR and in a Real-Time Duplex LATE-PCR We designed a duplex real-time LATE-PCR assay for simultaneous amplification of sequences within exons of the murine Oct4 and Xist genes (GenBank Accession Number NM 013633 and L04961, respectively). Each reaction was run in a final volume of 50 µl and contained the following reagents: 1×PCR buffer (Invitrogen, Carlsbad, Calif.) comprised by 20 mM Tris-HCl, pH 8.4, and 50 mM KCl, 3 mM $MgCl_2$, 0.4 mM of each dNTP, 50 nM Oct4 Limiting Primer having the sequence 5' TGGCTGGACACCTGGCTTCA-GACT 3' (SEQ ID NO: 33), 2 µM Oct4 Excess Primer having the sequence 5' CAACTTGGGGGACTAGGC 3' (SEQ ID NO: 34), 100 nM Xist Limiting Primer having the sequence 5' GGTCGTACAGGAAAAGATGGCGGCT-CAA 3' (SEQ ID NO: 35), 2 µM Xist Excess Primer having the sequence 5' TGAAAGAAACCACTAGAGGGCA 3' (SEQ ID NO:36), 1 µµM of a low melting-point Oct4 molecular beacon probe having the sequence 5' TET-CCG CCT GGG ATG GCA TAC TGT GGA AGG CGG-Dabcyl 3' (SEQ ID NO: 37) and 300 nM of a mispriming prevention reagent (that we refer to as compound 9-3bDD) having the sequence 5'Dabcyl-CGTTATAATGAAATTATAACG-Dabcyl 3' (SEQ. ID. No. 38). Antibody-complexed Platinum® Taq DNA polymerase (Invitrogen, Carlsbad, Calif.) was also included in the PCR mixture at concentrations of 1, 2, or 3 Units per assay). A molecular beacon probe for the detection of Xist amplicons was not added in this example.

In parallel with these duplex LATE-PCRs, we also ran a series of assays for LATE-PCR amplification of the Oct4 amplicon only. These assays had identical composition as the aforementioned duplexes, except for the omission of the Xist Limiting Primer and the Xist Excess Primer.

Mouse genomic DNA (Sigma, St Louis, Mo.) was added to all the assays and provided the templates for PCR amplification. The number of genomes added to each tube was calculated as 1000, based on a 6 pg/genome size (see Vendrely and Vendrely (1949) Experientia 5: 327-329).

All assays were run in duplicates. Amplification was carried out in an ABI Prism 7700 Sequence Detector (Applied Biosystems, CA) with a thermal cycling profile comprised of 1 cycle at 95° C. for 5 minutes; 6 cycles at 95° C. for 10 sec, 63° C. for 20 sec, and 72° C. for 30 sec; and 54 cycles at 95° C. for 15 sec, 55° C. for 25 sec, 72° C. for 35 sec, and 45° C. for 30 sec, with fluorescence acquisition at 45° C. in the TET channel.

The results of this experiment are shown in FIG. 24, which plots the fluorescent signals generated by accumulating Oct4 amplicons through hybridization with the TET-Oct4 molecular beacon probe. When only one pair of primers was present, increasing Taq polymerase concentration from 1 Unit/assay (circle 241) to 2 Units/assay (circles 242) or 3 Units/assay (circles 243) had the effect of making the slope of the signals steeper, due to increased amplification efficiency. Signals identified by Circles 242 and 243 (2 and 3 Units/assay, respectively) were interspersed, suggesting that maximal efficiency had been reached at approximately these levels. As expected, the slopes of the lines generated by the duplex reactions (circles 244, 245 and 246) were in all cases lower than those generated by amplification of a single amplicon, because the Taq polymerase was used at twice that rate. As in the case of the single-amplicon LATE-PCR, augmenting Taq concentration in the duplex reaction from 1 Unit/assay (circle 244) to 2 Units/assay (circle 245) or 3 Units/assay (circle 246) resulted in an increase in signal slope. There was no further increase in the initial slope of the 3 Units/assay (circle 246) when compared to the initial slope of the 2 Units/assay (circle 245), again suggesting that maximal efficiency had been reached. However, the 3 Units/assay samples (circle 246) quickly reached a plateau and the slope started declining, unlike that one of the 2 Units/assay samples (circle 245), indicating the probable occurrence of mispriming in the presence of the highest Taq concentration tested, which was not the case for samples 243, also containing 3 Taq Units/assay but only one pair of primers. In spite of the higher amount of available Taq in the single-amplicon assays when compared to the duplexes (3 units being used to generate one amplicon rather than two amplicons at the same time), more mispriming occurred in the duplexes due to the addition of the Xist primers. In order to obtain maximal efficiency without mispriming, Taq polymerase concentration needs, thus, to be optimized in consideration of the number and sequences of the primers added to the reaction.

What is claimed is:

1. A sequential DNA amplification-sequencing method comprising:
   a) amplifying at least two DNA targets by LATE-PCR to generate an amplification product containing copies of at least two excess primer strands and at least two limiting primer strands;
   b) processing the amplification product with a clean-up procedure consisting of diluting the amplification product by a factor of at least eighty to produce a cleaned-up amplification product; and
   c) sequencing the copies of at least one of said excess primer strands in the cleaned-up amplification product.

2. The method of claim 1, wherein sequencing is dideoxy cycle sequencing.

3. The method of claim 1, wherein the act of diluting is performed in two steps.

4. The method of claim 1, wherein the LATE-PCR comprises monitoring the adequacy of production of single-stranded product, wherein the monitoring comprises determining the ratio of single-stranded product to double-stranded product.

5. The method of claim 1, wherein the excess primer strand is sequenced using a primer having a sequence identical to a limiting primer used in the LATE-PCR.

* * * * *